(12) United States Patent
Walia et al.

(10) Patent No.: US 10,036,034 B2
(45) Date of Patent: Jul. 31, 2018

(54) SEQUENCES INVOLVED IN PLANT YIELD AND METHODS OF USING

(71) Applicant: NUtech Ventures, Lincoln, NE (US)

(72) Inventors: Harkamal Walia, Lincoln, NE (US); Dante Placido, Oakland, NE (US); Thomas E. Clemente, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 577 days.

(21) Appl. No.: 14/562,182

(22) Filed: Dec. 5, 2014

(65) Prior Publication Data

US 2015/0225736 A1    Aug. 13, 2015

Related U.S. Application Data

(60) Provisional application No. 61/939,329, filed on Feb. 13, 2014.

(51) Int. Cl.
| | |
|---|---|
| *C12N 15/82* | (2006.01) |
| *A01H 5/10* | (2018.01) |
| *C12N 15/01* | (2006.01) |
| *A01H 1/04* | (2006.01) |
| *A23D 9/00* | (2006.01) |
| *A23K 10/00* | (2016.01) |
| *A23L 7/10* | (2016.01) |
| *C07K 14/415* | (2006.01) |

(52) U.S. Cl.
CPC ........... *C12N 15/8273* (2013.01); *A01H 1/04* (2013.01); *A23D 9/00* (2013.01); *A23K 10/00* (2016.05); *A23L 7/10* (2016.08); *A23L 7/198* (2016.08); *C07K 14/415* (2013.01); *C12N 15/01* (2013.01); *C12N 15/8261* (2013.01); *A23V 2002/00* (2013.01); *C12Q 2600/13* (2013.01); *C12Q 2600/156* (2013.01); *Y02A 40/146* (2018.01)

(58) Field of Classification Search
CPC ........................ C12N 15/8261; C12N 15/8273
See application file for complete search history.

(56) References Cited

U.S. PATENT DOCUMENTS

| | | | |
|---|---|---|---|
| 2006/0162006 A9 | 7/2006 | Sherman et al. | |
| 2011/0191916 A1 | 8/2011 | Erickson et al. | |
| 2012/0199148 A1 | 8/2012 | Xu et al. | |
| 2012/0219959 A1 | 8/2012 | Carroll et al. | |

OTHER PUBLICATIONS

GenBank Accession AK333711, available online on Jun. 25, 2009.*
Kawaura et al (BMC Genomics. 2009; 10: 271).*
A. Sayaslan / Lebensm.—Wiss. u.—Technol. 37 (2004) 499-515.*
Kawaura et al (BMC Genomics. 2009; 10: 271) (Year: 2009).*

International Preliminary Report on Patentability in International Application No. PCT/US2015/015388, dated Aug. 16, 2016, 10 pages.
Bao et al., "Brassinosteroids interact with auxin to promote lateral root development in Arabidopsis," *Plant Physiol.* Apr. 2004;134(4):1624-31. Epub Mar. 26, 2004.
Bolduc et al., "Dual functions of the KNOTTED1 homeodomain: sequence-specific DNA binding and regulation of cell-to-cell transport," *Sci Signal.* Jun. 10, 2008;1(23):pe28. doi: 10.1126/scisignal.123pe28.
Close et al., "HarvEST," *Methods Mol Biol.* 2007;406:161-77.
Cui et al., "Detecting single-feature polymorphisms using oligonucleotide arrays and robustified projection pursuit," *Bioinformatics.* Oct. 15, 2005;21(20):3852-8. Epub Aug. 23, 2005.
Del Pozo et al., "Arabidopsis E2Fc functions in cell division and is degraded by the ubiquitin-SCR(AtSKP2) pathway in response to light," *Plant Cell.* Dec. 2002;14(12):3057-71.
Del Pozo et al., "The balance between cell division and endoreplication depends on E2FC-DPB, transcription factors regulated by the ubiquitin-SCFSKP2A pathway in Arabidopsis," *Plant Cell.* Sep. 2006;18(9):2224-35. Epub Aug. 18, 2006.
Devos et al., "Chromosome aberrations in wheat nullisomic-tetrasomic and ditelosomic lines," *Cereal Research Communications*, 1999, 27(3):231-239.
Dubois et al., "Optimizing the statistical estimation of the parameters of the Farquhar-von Caemmerer-Berry model of photosynthesis," *New Phytol.* 2007;176(2):402-14.
Farquhar et al., "A biochemical model of photosynthetic CO2 assimilation in leaves of C3 species," *Planta.* Jun. 1980;149(1):78-90. doi: 10.1007/BF00386231.
GenBank Accession No. AAQ11887.1, Dec. 1, 2003, pp. 1.
GenBank Accession No. BAJ85164.1, May 20, 2011, pp. 1.
GenBank Accession No. BAJ89425.1, May 20, 2011, pp. 1.
GenBank Accession No. XP_003563314.1, Nov. 14, 2014, pp. 1.
Gill et al., "Alien introgressions represent a rich source of genes for crop improvement," *Proc Natl Acad Sci U S A.* May 10, 2011;108(19):7657-8. doi: 10.1073/pnas.1104845108. Epub Apr. 28, 2011.
Kim et al., "Detection and validation of single feature polymorphisms using RNA expression data from a rice genome array," *BMC Plant Biol.* May 29, 2009;9:65. doi: 10.1186/1471-2229-9-65.
Lavenus et al, "Lateral root development in Arabidopsis: fifty shades of auxin," *Trends Plant Sci.* Aug. 2013;18(8):450-8. doi: 10.1016/j.tplants.2013.04.006. Epub May 20, 2013.
Lee et al., "Genetic Dissection of the biotic stress response using a genome-scale gene network for rice," PNAS USA, 2011, 108(45):18548-18553.
Loriaux et al., 2006, Am. Soc. Plant Biol. Ann. Meet, Poster Presentation.
Mussig et al., "Brassinosteroids promote root growth in Arabidopsis," *Plant Physiol.* Nov. 2013;133(3):1261-71. Epub Oct. 2, 2003.
Orman-Ligeza et al., "Post-embryonic root organogenesis in cereals: branching out from model plants," *Trends Plant Sci.* Aug. 2013;18(8):459-67. doi: 10.1016/j.tplants.2013.04.010. Epub May 31, 2013.
Placido et al., "Introgression of novel traits from a wild wheat relative improves drought adaptation in wheat" *Plant Physiol.* Apr. 2013;161(4):1806-19. doi: 10.1104/pp.113.214262. Epub Feb. 20, 2013.

(Continued)

*Primary Examiner* — Lee A Visone
(74) *Attorney, Agent, or Firm* — Fish & Richardson P.C.

(57) ABSTRACT

Nucleic acid sequences involved in plant yield are provided, as are methods of using such nucleic acid sequences.

13 Claims, 21 Drawing Sheets

(56) References Cited

OTHER PUBLICATIONS

Ramirez-Parra et al., "Role of an Atypical E2F Transcription Factor in the Control of Arabidopsis Cell Growth and Differentiation," *Plant Cell*, Sep. 2004;16(9):2350-63. Epub Aug. 12, 2004.
Schuster et al. "Correcting for sequence biases in present/absent calls," *Genome Biol*. 2007;8(6):R125.
Sears, "Wheat Cytogenetics," *Annual Review of Genetics*, 1969, 3:451-468.
Sorrells et al., "Comparative DNA sequence analysis of wheat and rice genomes," *Genome Res*. Aug. 2003;13(8):1818-27.
Truernit and Haseloff, "A Role for KNAT Class II Genes in Root Development," *Plant Signal Behav*. Jan. 2007;2(1):10-12.
Truernit et al., "A map of KNAT gene expression in the Arabidopsis root," *Plant Mol Biol*. Jan. 2006;60(1):1-20.
Walia et al., "Array-based genotyping and expression analysis of barley cv. Maythorpe and Golden Promise," *BMC Genomics*. Mar. 30, 2007;8:87.
Zhang et al., "Molecular characterization of durum and common wheat recombinant lines carrying leaf rust resistance (Lr19) and yellow pigment (Y) genes from Lophopyrum ponticum," *Theor Appl Genet*. 2005, 111(3):573-82. Epub May 24, 2005.
Zhu et al., "Detection of quantitative trait loci for seminal root traits in maize (*Zea mays* L.) seedlings grown under differential phosphorus levels," *Theor Appl Genet*. Jun. 2006;113(1):1-10. Epub May 3, 2006.
International Search Report and Written Opinion in International Application No. PCT/US2015/015388 dated Jun. 3, 2015, 12 pages.

\* cited by examiner

Part A

```
Ta.28144
Pavon           GAACGCTGCTCCTTCTGATCCTTCT░░░░░░CC░T░░░░░░CACAAGA
Pavon-TL        TAACGGCAAGCGGCCCG-TCCTTCT░░░CC░T░░░G░░CTACAGA
Pavon-Null      GAACGCTGCTCCTTCTGATCCTTCT░░░░░░CC░T░░░░░░CACAAGA
Ta.28144.1.S1_at GAACGCTGCTCCTTCTGATCCTTCT░░░░░░CC░T░░░░░░CACAAGA
Probe 7                                  TTCT░░░░░░CC░T░░░░░░C Ta.7772
Pavon           TCGG░GAGCTTTAGG░░GCTG░CA░TTCCTCAGATAGG-AATTCCTGTAA
Pavon-TL        TCGG░GAGCTTTAGG░░GCTG░CA░TTCCTCAGCTAGG-AGTTCCTGTAA
Pavon-Null      TCGG░GAGCTTTAGG░░GCTG░CA░TTCCTCAGATAGG-AATTCCTGTAA
Ta.7772.2.S1_a_at TCGG░GAGCTTTAGG░░GCTG░CA░TTCCTCAGATAGG-AATTCCTGTAA
Probe 8             GG░GAGCTTTAGG░░GCTG░CA░TTC Ta.16810
Pavon           TGGTTTGTATGGAGTGTTGTGTTGCAG░T░TTAGGGCTGTTGT-TTTT--
Pavon-TL        TGGTTTGTATGGAGTGTTGTGCTGCAG░T░TTAGGGCTCTTTTTTCT-TT
Pavon-Null      TGGTTTGTATGGAGTGTTGTGCTGCAG░T░TTAGGGCTCTTTTTTCT-TT
Ta.16810.1.S1_at TGGTTTGTATGGAGTGTTGTGCTGCAG░T░TTAGGGCTCTTTTTTCT-TT
Probe 3              TTGTATGGAGTGTTGTGCTGCAG░T░
```

Figure 8

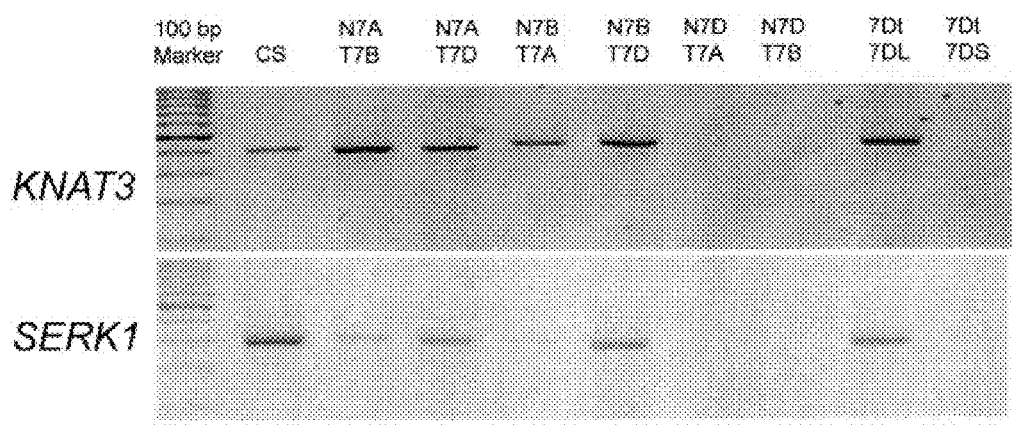

Figure 9

```
LRD7_Ag    MWPDAACSP-HGGRGNSIPSPRNSFRQHVRVHAMEAVMACWELEQTLQSLTGASPGEGTGA  59
LRD7_TL    MWPDVACSP-HGGRGNSIPSRNSSRQHVRVHAMEAVMACWELEQTLQSLTGASPGEGTGA  59
LRD7_P76   MGPDAACSPDDGGRGNSIPSRNSSPQHVRVHAMEAVMACWELEQTLQSLTGASPGEGTGA  60
           * ** ****  **** ****** ** .*********************************

LRD7_Ag    TMSDDEDNPVDSESNMFRRERCVRWHGLRNANRGMTKTIRSTVRATCFDGNDVSDGMGFG  119
LRD7_TL    TMSDDEINPVDSESNMFRRERCVRWHGLRNANRGMIKTIRSTVRATCFDGNDVSDGMGFG  119
LRD7_P76   TMSDDEDNPVDSESNMFR------WK---------MKTIRSTVRATCFGGNDVSDGMGFG  106
           ******  *********         *         * ***********  *********

LRD7_Ag    MLTEGERSLVERVRQELKHELKQGYREKLVDIREEILPKRPAGKLPGDTASTLKAWWQAH  179
LRD7_TL    MLTEGERSLVERVRQELKHELKQGYREKLVDIREEILRKRPAGKLPGDTASTLKAWWQAH  179
LRD7_P76   MLTEGERSLVERVRQELKRELRQGYREKLVDIREEMLRKRPAGKLPGDTASTLKAWWQAH  166
           ****************** ** ************* ***********************

LRD7_Ag    AKWPYPTEEDKARLVQETGLQLKXIRNWFINQRKRNWHSNPTSSSSDKSKRKRNNAGEGN  239
LRD7_TL    AKWPYPTEEDKARLVQETGLQLKXINNWFINQRKRNWHSNPTSSSSDKSKRKRNNAGEGN  239
LRD7_P76   AKWPYPTEEDKARLVQETGLQLKQINNWFINQRKRNWHSNPTSSSSDKSKRKRNNAGDGN  226
           ***********************  ***********************************

LRD7_Ag    AEQSW  244
LRD7_TL    AEQSW  244
LRD7_P76   AEQSW  231
           *****
```

SEQUENCES INVOLVED IN PLANT YIELD AND METHODS OF USING

CROSS REFERENCE TO RELATED APPLICATIONS

This application claims the benefit of priority under 35 U.S.C. 119(e) to U.S. Application No. 61/939,329 filed Feb. 13, 2014.

FEDERALLY SPONSORED RESEARCH OR DEVELOPMENT

This invention was made with government support under 1121648 awarded by the National Science Foundation. The government has certain rights in the invention.

TECHNICAL FIELD

This disclosure generally relates to plants exhibiting increased yield.

BACKGROUND

As agriculture is increasingly shifted to marginal lands and drought events become more frequent and intense, specific root morphological traits that can improve drought tolerance and sustain yields in suboptimal conditions hold immense potential. To effectively incorporate drought-adaptive root traits in crops like wheat and rice, we need to better understand the genetic and physiological basis of adaptive root traits. This disclosure describes several genes that are involved in root development as well as yield.

SUMMARY

This disclosure provides nucleic acid sequences involved in plant yield and methods of using such nucleic acid sequences.

In one aspect, a hybrid, variety, line, or cultivar is provided. Such a hybrid, variety, line, or cultivar includes plants having a mutation in one or more endogenous nucleic acids such as SEQ ID NOs: 1 or 3. In some embodiments, the plants exhibit an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant lacking the mutation under corresponding conditions. Seed produced by such a hybrid, variety, line, or cultivar also is provided, where the seed includes the mutation in one or more endogenous nucleic acids having a sequence such as SEQ ID NOs: 1 or 3.

In another aspect, a method of making a plant is provided. Such a method typically includes the steps of inducing mutagenesis in plant cells to produce mutagenized cells, obtaining one or more plants from the mutagenized cells, and identifying at least one of the plants that contains a mutation in one or more endogenous nucleic acids such as SEQ ID NOs: 1 or 3. Such a method can further include identifying at least one of the plants that exhibits an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant lacking the mutation under corresponding conditions.

Mutagenesis can be induced using a chemical mutagen or ionizing radiation. Representative chemical mutagens include, without limitation, nitrous acid, sodium azide, acridine orange, ethidium bromide, and ethyl methane sulfonate (EMS). Representative ionizing radiation includes, without limitation, x-rays, gamma rays, fast neutron irradiation, and UV irradiation. Mutagenesis can be induced using TALEN or zinc-finger technology.

In another aspect, a method of producing a plant is provided. Such a method can include the steps of crossing at least one plant of a first line with at least one plant of a second line and selecting for progeny plants that have the mutation. Generally, the plant of the first line has a mutation in one or more endogenous nucleic acids having a sequence such as SEQ ID NOs: 1 or 3. Such a method further can include selecting for progeny plants that exhibit an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant lacking the mutation under corresponding conditions.

A mutation as described herein can be, without limitation, a point mutation, an insertion, a deletion, or a substitution.

In still another aspect, a transgenic plant is provided that includes a plant expression vector. Typically, the expression vector includes a nucleic acid molecule that is at least 25 nucleotides in length and has at least 91% sequence identity to a sequence such as SEQ ID NOs: 1 or 3. In some embodiments, expression of the nucleic acid molecule results in plants exhibiting an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant not having or not expressing the nucleic acid molecule under corresponding conditions. Seed produced by such a transgenic plant also is provided, where the seed includes the expression vector.

In one aspect, a transgenic plant is provided that includes a heterologous nucleic acid molecule of at least 25 nucleotides in length, wherein the nucleic acid molecule hybridizes under stringent conditions to a nucleic acid sequence such as SEQ ID NOs: 1 or 3. In some embodiments, expression of the heterologous nucleic acid molecule results in plants exhibiting an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant not having or not expressing the nucleic acid molecule under corresponding conditions. Seed produced by such a transgenic plant also is provided, where the seed includes the heterologous nucleic acid molecule.

In one aspect, a transgenic plant is provided that includes a vector. Generally, the vector includes a nucleic acid molecule having at least 91% sequence identity to 25 or more contiguous nucleotides of a nucleic acid sequence such as SEQ ID NOs: 1 or 3. In some embodiments, expression of the nucleic acid molecule results in the plant exhibiting an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant not having or not expressing the nucleic acid molecule under corresponding conditions.

In another aspect, a method of making a transgenic plant is provided. Such a method typically includes expressing a transgene in the plant. The transgene encodes a double-stranded RNA molecule that inhibits expression from a nucleic acid sequence such as SEQ ID NOs: 1 or 3. The double-stranded RNA molecule includes at least 25 consecutive nucleotides having 91% or greater sequence identity to a sequence such as SEQ ID NOs: 1 or 3. In some embodiments, expression of the transgene results in the plant exhibiting an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant not having or not expressing the nucleic acid molecule under corresponding conditions. In some embodiments, the double-stranded RNA molecule has a sequence such as SEQ ID NOs: 5 or 6.

In another aspect, a method of producing a plant is provided. Such a method generally includes the steps of introducing a heterologous nucleic acid molecule operably linked to a promoter into plant cells to produce transgenic plant cells, and regenerating transgenic plants from the transgenic cells. Typically, the heterologous nucleic acid molecule includes at least 25 nucleotides in length and has at least 91% sequence identity to a nucleic acid sequence such as SEQ ID NOs: 1 or 3. Such transgenic plants exhibit an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant not having or not expressing the heterologous nucleic acid molecule under corresponding conditions. Such a method further can include selecting at least one of the transgenic plants that exhibits an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant not having or not expressing the heterologous nucleic acid molecule under corresponding conditions.

In some embodiments, the nucleic acid is in sense orientation, while, in some embodiments, the nucleic acid is in antisense orientation.

In still another aspect, a transgenic plant is provided that includes a plant expression vector. Generally, the expression vector includes a nucleic acid molecule having at least 95% sequence identity to a sequence such as SEQ ID NOs: 1 or 3, or a fragment of any of those sequences encoding a functional polypeptide. In some embodiments, expression of the nucleic acid molecule or a functional fragment thereof results in plants exhibiting a decrease in the length of the primary root under limiting water conditions, a decrease in the length of the seminal root under limiting water conditions, a decrease in lateral root density under limiting water conditions, a decrease in root biomass under limiting water conditions, a decrease in the number of seeds per plant under water conditions that are not limiting, a decrease in the average size of the seed under water conditions that are not limiting, and/or a decrease in the average weight of the seed under water conditions that are not limiting relative to a corresponding plant not expressing the nucleic acid molecule or functional fragment thereof under corresponding conditions. Seed produced by such a transgenic plant also is provided, where the seed includes the expression vector.

In another aspect, a transgenic plant is provided that includes a heterologous nucleic acid molecule. Generally, the nucleic acid molecule hybridizes under stringent conditions to a nucleic acid sequence such as SEQ ID NOs: 1 or 3, or a fragment thereof encoding a functional polypeptide. In some embodiments, expression of the heterologous nucleic acid molecule or functional fragment thereof results in plants exhibiting a decrease in the length of the primary root under limiting water conditions, a decrease in the length of the seminal root under limiting water conditions, a decrease in lateral root density under limiting water conditions, a decrease in root biomass under limiting water conditions, a decrease in the number of seeds per plant under water conditions that are not limiting, a decrease in the average size of the seed under water conditions that are not limiting, and/or a decrease in the average weight of the seed under water conditions that are not limiting relative to a corresponding plant not expressing the nucleic acid molecule or functional fragment thereof under corresponding conditions. Seed produced by such a transgenic plant also is provided, where the seed includes the heterologous nucleic acid molecule.

In one aspect, seed from a transgenic plant is provided that includes a vector. Typically, such a vector includes a nucleic acid molecule having at least 95% sequence identity to a nucleic acid sequence such as SEQ ID NOs: 1 or 3, or a fragment thereof encoding a functional polypeptide. In some embodiments, expression of the nucleic acid molecule or functional fragment thereof results in the seed exhibiting a decrease in the length of the primary root under limiting water conditions, a decrease in the length of the seminal root under limiting water conditions, a decrease in lateral root density under limiting water conditions, a decrease in root biomass under limiting water conditions, a decrease in the number of seeds per plant under water conditions that are not limiting, a decrease in the average size of the seed under water conditions that are not limiting, and/or a decrease in the average weight of the seed under water conditions that are not limiting relative to a corresponding plant not expressing the nucleic acid molecule or functional fragment thereof under corresponding conditions.

In another aspect, a method of producing a plant is provided. Such a method typically includes the steps of introducing a heterologous nucleic acid molecule operably linked to a promoter into plant cells to produce transgenic cells, and regenerating transgenic plants from the transgenic cells, wherein the transgenic plants exhibit a decrease in the length of the primary root under limiting water conditions, a decrease in the length of the seminal root under limiting water conditions, a decrease in lateral root density under limiting water conditions, a decrease in root biomass under limiting water conditions, a decrease in the number of seeds per plant under water conditions that are not limiting, a decrease in the average size of the seed under water conditions that are not limiting, and/or a decrease in the average weight of the seed under water conditions that are not limiting relative to a corresponding plant not expressing the heterologous nucleic acid molecule or functional fragment thereof under corresponding conditions. The heterologous nucleic acid molecule typically has at least 95% sequence identity to a nucleic acid sequence such as SEQ ID NOs: 1 or 3, or a fragment thereof encoding a functional polypeptide. Such a method further can include selecting at least one of the transgenic plants that exhibits a decrease in the length of the primary root under limiting water conditions, a decrease in the length of the seminal root under limiting water conditions, a decrease in lateral root density under limiting water conditions, a decrease in root biomass under limiting water conditions, a decrease in the number of seeds per plant under water conditions that are not limiting, a decrease in the average size of the seed under water conditions that are not limiting, and/or a decrease in the average weight of the seed under water conditions that are not limiting relative to a corresponding plant not expressing the heterologous nucleic acid molecule or functional fragment thereof under corresponding conditions. In some embodiments, the heterologous nucleic acid molecule is introduced into the plant cells using particle bombardment, Agrobacterium-mediated transformation, microinjection, polyethylene glycol-mediated transformation, liposome-mediated DNA uptake, or electroporation.

In still another aspect, a transgenic plant is provided that includes a plant expression vector. Generally, the expression vector includes a nucleic acid molecule having at least 95% sequence identity to a sequence such as SEQ ID NOs: 9 or 11, or a fragment of any of those sequences encoding a functional polypeptide. In some embodiments, expression of the nucleic acid molecule or a functional fragment thereof results in plants exhibiting an increase in the average size of the seed (i.e., length, width and thickness) relative to a corresponding plant not expressing the nucleic acid molecule or functional fragment thereof. Seed produced by such a transgenic plant also is provided, where the seed includes the expression vector.

In another aspect, a transgenic plant is provided that includes a heterologous nucleic acid molecule. Generally, the nucleic acid molecule hybridizes under stringent conditions to a nucleic acid sequence such as SEQ ID NOs: 9 or 11, or a fragment thereof encoding a functional polypeptide. In some embodiments, expression of the heterologous nucleic acid molecule or functional fragment thereof results in plants exhibiting an increase in the average size of the seed (i.e., length, width and thickness) relative to a corresponding plant not expressing the nucleic acid molecule or functional fragment thereof. Seed produced by such a transgenic plant also is provided, where the seed includes the heterologous nucleic acid molecule.

In one aspect, seed from a transgenic plant is provided that includes a vector. Typically, such a vector includes a nucleic acid molecule having at least 95% sequence identity to a nucleic acid sequence such as SEQ ID NOs: 9 or 11, or a fragment thereof encoding a functional polypeptide. In some embodiments, expression of the nucleic acid molecule or functional fragment thereof results in the seed exhibiting an increase in the average size of the seed (i.e., length, width and thickness) relative to a corresponding plant not expressing the nucleic acid molecule or functional fragment thereof.

In another aspect, a method of producing a plant is provided. Such a method typically includes the steps of introducing a heterologous nucleic acid molecule operably linked to a promoter into plant cells to produce transgenic cells, and regenerating transgenic plants from the transgenic cells, wherein the transgenic plants exhibit an increase in the average size of the seed (i.e., length, width and thickness) relative to a corresponding plant not expressing the nucleic acid molecule or functional fragment thereof. The heterologous nucleic acid molecule typically has at least 95% sequence identity to a nucleic acid sequence such as SEQ ID NOs: 9 or 11, or a fragment thereof encoding a functional polypeptide. Such a method further can include selecting at least one of the transgenic plants that exhibits an increase in the average size of the seed (i.e., length, width and thickness) relative to a corresponding plant not expressing the nucleic acid molecule or functional fragment thereof. In some embodiments, the heterologous nucleic acid molecule is introduced into the plant cells using particle bombardment, Agrobacterium-mediated transformation, microinjection, polyethylene glycol-mediated transformation, liposome-mediated DNA uptake, or electroporation.

In another aspect, a method of screening plants is provided. Such a method typically includes providing a mutant or transgenic plant as described herein, and determining the length of the primary root under limiting water conditions, the length of the seminal root under limiting water conditions, lateral root density under limiting water conditions, root biomass under limiting water conditions, the number of seeds per plant under water conditions that are not limiting, the average size of the seed under water conditions that are not limiting, and/or the average weight of the seed under water conditions that are not limiting relative to a corresponding plant not having a mutation or having or expressing a transgene under corresponding conditions.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part A

FIG. 8 is an alignment to validate polymorphic probes identified via Single Feature Polymorphism (SFP) analysis. Three wheat probes identified from the rice ortholog cluster that emerged from in silico mapping of rice orthologs to the syntenic region between wheat 7DL and rice chromosome 6 were selected (top set: Probe 7, SEQ ID NO:77; middle set: Probe 8, SEQ ID NO:78; bottom set: Probe 3, SEQ ID NO:79). PCR amplicons were cloned and sequenced from Pavon 76 (Pavon; SEQ ID NOs:80-82 (top to bottom)), Pavon 76 with 1-96-1 translocation (Pavon-TL; SEQ ID NOs:83-85 (top to bottom)), TL sister line lacking the 1-96-1 translocation (Pavon-Null; SEQ ID NOs:86-88 (top to bottom)), and the consensus sequence (Ta . . . ; SEQ ID NOs:89-91 (top to bottom)). The alignment shows the sequence obtained from the clones, the consensus probe set sequence and the SFP analysis identified probe sequence match. Mismatches are colored red.

FIG. 9 is photographs of chromosome mapping of five root trait-associated candidate genes using the wheat genetic stocks. Using Chinese Spring, nulli-tetrasomic and di-telosomic lines for Group 7, PCR-based mapping of candidate genes was performed. The representative genes are KNAT3 (Knotted-like homeobox gene 3 in *Arabidopsis*; also known as LRD7=Lateral Root Density 7 in wheat) and SERK1 (Somatic embryogenesis receptor-like kinase 1). These two genes were selected because they were differentially regulated between the TL line and control genotypes, and because their rice orthologs mapped to chromosome 6 with syntenic relation to wheat chromosome 7D long arm. With the exception of AgI, four genes mapped to wheat chromosome 7DL. CS: Chinese Spring; N7AT7B: Nullisomic 7A-Tetrasomic 7B; N7AT7D: Nullisomic 7A-Tetrasomic 7D; N7BT7A: Nullisomic 7B-Tetrasomic 7D; N7BT7D: Nullisomic 7B-Tetrasomic 7A; N7DT7A: Nullisomic 7D-Tetrasomic 7B; N7DT7B: Nullisomic 7D-Tetrasomic 7B; 7Dt7DL: Ditelosomic 7DL; 7Dt7DS: Ditelosomic 7DS.

Part B

Figure 10:
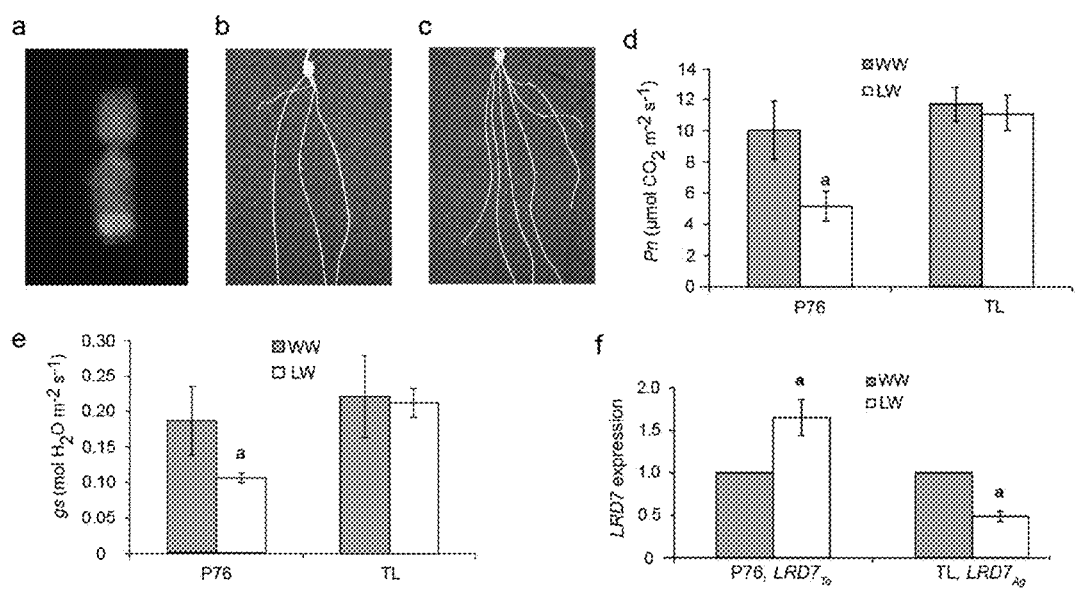

FIG. 10 is data demonstrating that *Agropyron* introgression improves drought response. Panel (a) shows wheat chromosome 7D (in red) with *Agropyron* introgression (in green) visualized using genomic in situ hybridization. Panel (b) is a photograph of a six-day old seedling of Pavon76 (P76) grown under limited water (LW), showing a lower number of roots and lateral root density compared to the photograph shown in Panel (c) of roots of the translocation line (TL) grown under limited water. Panel (d) is a graph showing that LW stress reduced the net photosynthetic rate (Pn) compared to well-watered (WW) conditions in P76 but not in TL (mean±sd, n=9) in 18 d-old plants. Panel (e) is a graph showing that TL maintained stomatal conductance (gs) under LW conditions whereas stomatal conductance was reduced in P76 under LW conditions (mean±sd, n=9). Panel (f) is a graph showing allele-specific expression of LRD7 in seedling roots, demonstrating that the wheat allele, LRD7Ta, increased under LW conditions and the *Agropyron* allele, LRD7Ag, was repressed under LW conditions. Expression of LRD7 under LW conditions is shown relative to the expression under well-watered (WW) conditions for each genotype (mean±sd, from 3 biological and 2 technical replicates). "a" indicates a significant difference between LW and WW at $p<0.05$.

Figure 11:
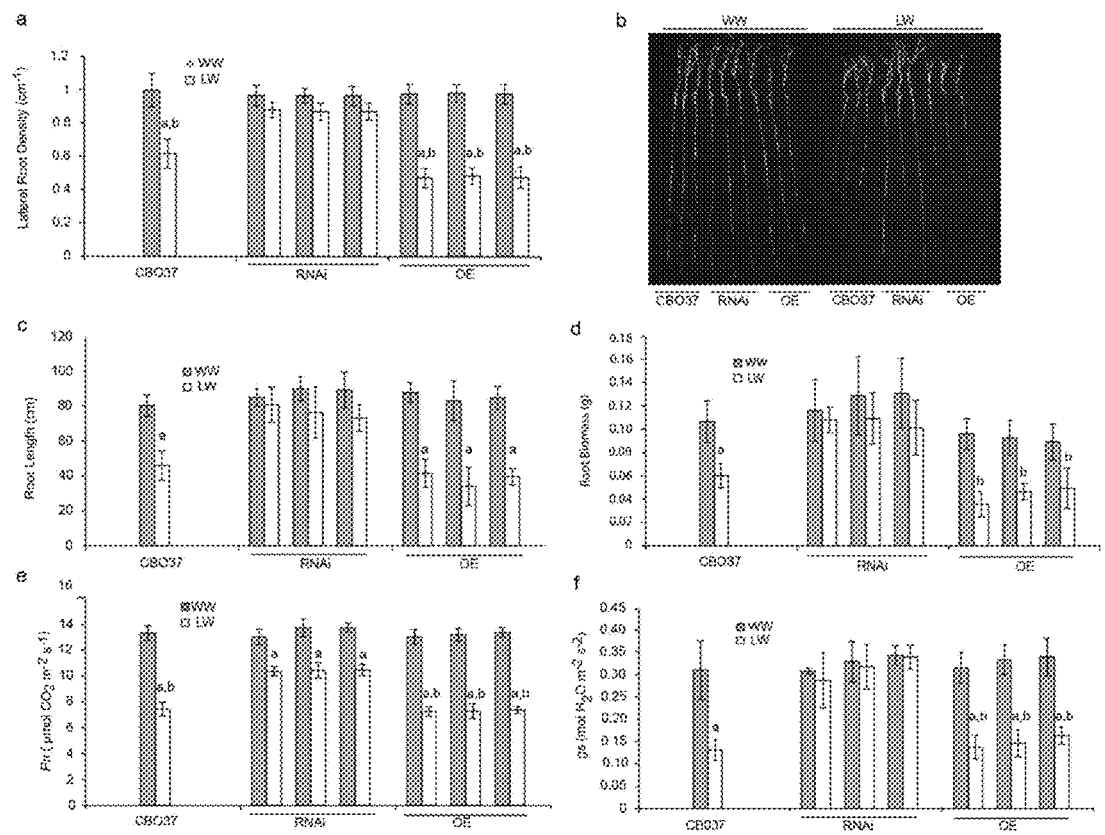

FIG. 11 is data demonstrating that LRD7 negatively regulates root traits. Panel (a) is a graph showing data from experiments in which seedlings of CBO37, RNAi and OE events for LRD7 were grown in WW and LW conditions and assayed for lateral root density on the primary root. Lateral root density decreased in CBO37 and OE events in LW but not in the RNAi events (mean±sd, n=30). Panel (b) is a photograph showing that, in the pre-tillering stage, CBO37, RNAi and OE plants differed in root length under a 20 d LW treatment. The RNAi events maintained root length under LW, unlike CBO37 and the OE events. Panels (c) and (d) are graphs of data demonstrating that root length and root dry weight were higher in the RNAi plants compared to CBO37 and OE plants in LW (mean±sd, n=9). Panel (e) is a graph showing that net photosynthetic rate (Pn) declined in all genotypes in response to LW. However, the decline in Pn in the RNAi events was less than that observed in CBO37 and the OE events (mean±sd, n=9). Panel (f) is a graph showing that the LRD7 RNAi events did not experience a drop in the stomatal conductance (gs) under LW. "a" indicates significant difference between the WW and LW and "b" indicates significant difference between the RNAi or OE and CBO37 in LW at $p<0.05$.

Figure 12:
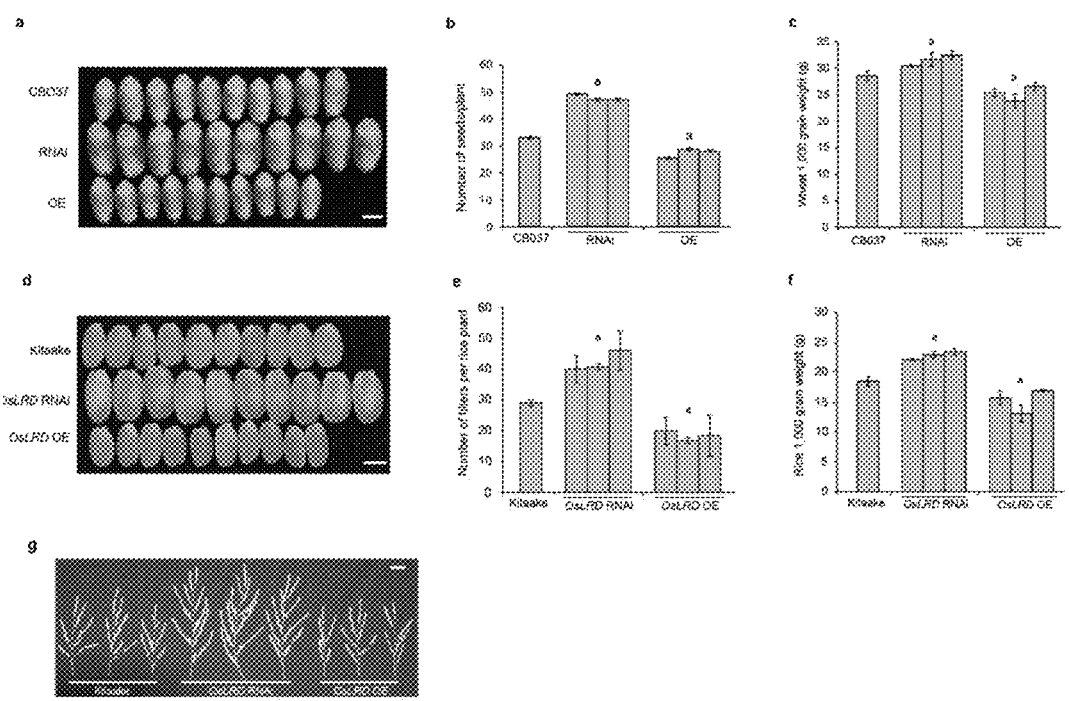

FIG. 12 is data demonstrating that LRD7 negatively regulates yield components. Panel (a) is a photograph showing a comparison of wheat seed size among CBO37, LRD7 RNAi, and OE events demonstrated by aligning 10 seeds from a pool of 10 plants per genotype. Panel (b) is a graph showing the number of seeds per wheat plant. Plants were grown to maturity in well-watered greenhouse conditions (mean±sd, n=10). Panel (c) is a graph showing 1,000-grain weight of CBO, LRD7 RNAi, and OE wheat plants grown in field conditions. Data from 3 independent transgenic events, 10 plants per genotype are shown. Panel (d) is a photograph showing rice seed size comparisons among CBO37, OsLRD7 RNAi, and OE plants demonstrated by aligning 10 seeds from a pool of 10 plants per genotype grown under field conditions. Panel (e) is a graph showing the number of seed bearing tillers per plant for Kitaake, OsLRD7 RNAi, and OE field grown plants at harvest (n=30 plants per genotype). Panel (f) is a graph showing 1,000-grain weight of Kitaake, OsLRD7 RNAi, and OE rice plants grown under field conditions. Data from 3 independent transgenic plants, 5 plants per genotype are shown. Panel (g) is a photograph showing a number of primary branches in the panicles from Kitaake, OsLRD7 RNAi, and OE plants. In Panels b-c and e-f, "a" represents significance at $p<0.05$ between CBO37 and RNAi or OE plants. Scale bar for Panels a and d is 1 mm and for Panel g is 30 mm.

Figure 13:
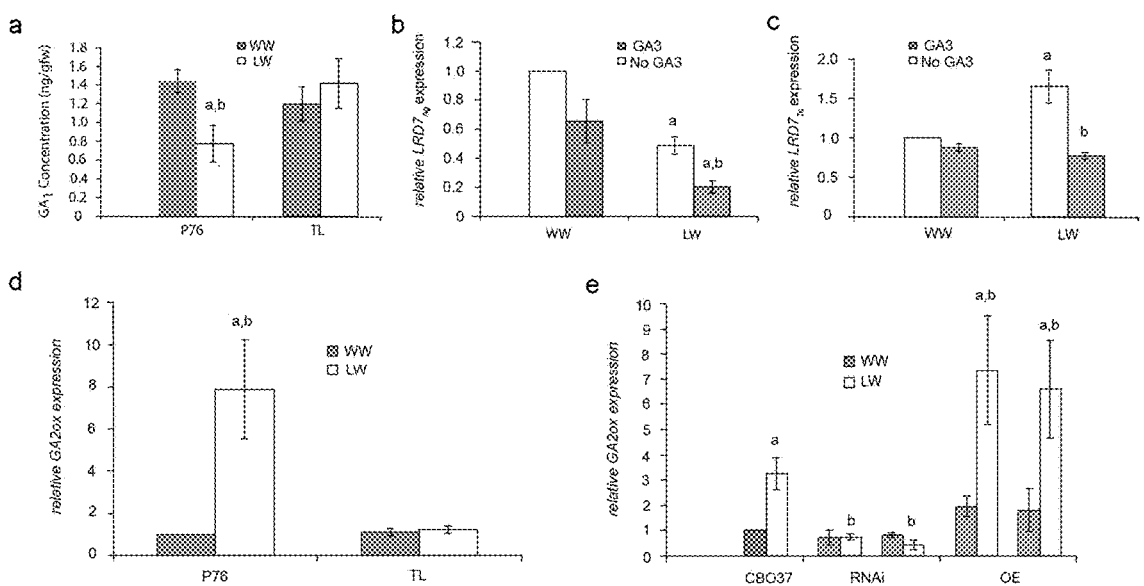

FIG. 13 is data showing that gibberellins (GA) regulate lateral root formation in wheat. Panel (a) is a graph showing GA1 levels in P76 and TL roots in WW and LW conditions (mean±sd, n=30). "a" represents differences between WW and LW for a genotype and "b" represents significant genotypic differences under LW ($p<0.05$). Panel (b) is a graph showing expression of *Agropyron* allele of LRD7 (LRD7Ag) in the TL line in WW and LW conditions, with and without GA3 treatment. Transcript abundance was measured relative to WW, non-GA3 treated sample (mean±sd, n=3). "a" represents significant differences between WW and LW for roots with GA3 and no GA3 treatment, "b" represents a significant difference in response to GA treatment ($p<0.05$). Panel (c) is a graph showing that LRD7Ta is down-regulated by GA3 treatment in LW conditions. Expression values were obtained relative to WW, non-GA3 treated sample as control (mean±sd, n=3). "a" represents significant differences between WW and LW for a genotype and "b" represents significant genotypic differences in LW conditions ($p<0.05$). Panels (d) and (e) are graphs showing that expression of GA2ox, a GA catabolic gene, was up-regulated in the wheat genotypes P76, CBO37 and OE events in LW (mean±sd, n=3). The "a" represents significance between WW and LW and "b" indicates significance between CBO37 and RNAi or OE events or between P76 and TL under LW ($p<0.05$).

Figure 14:
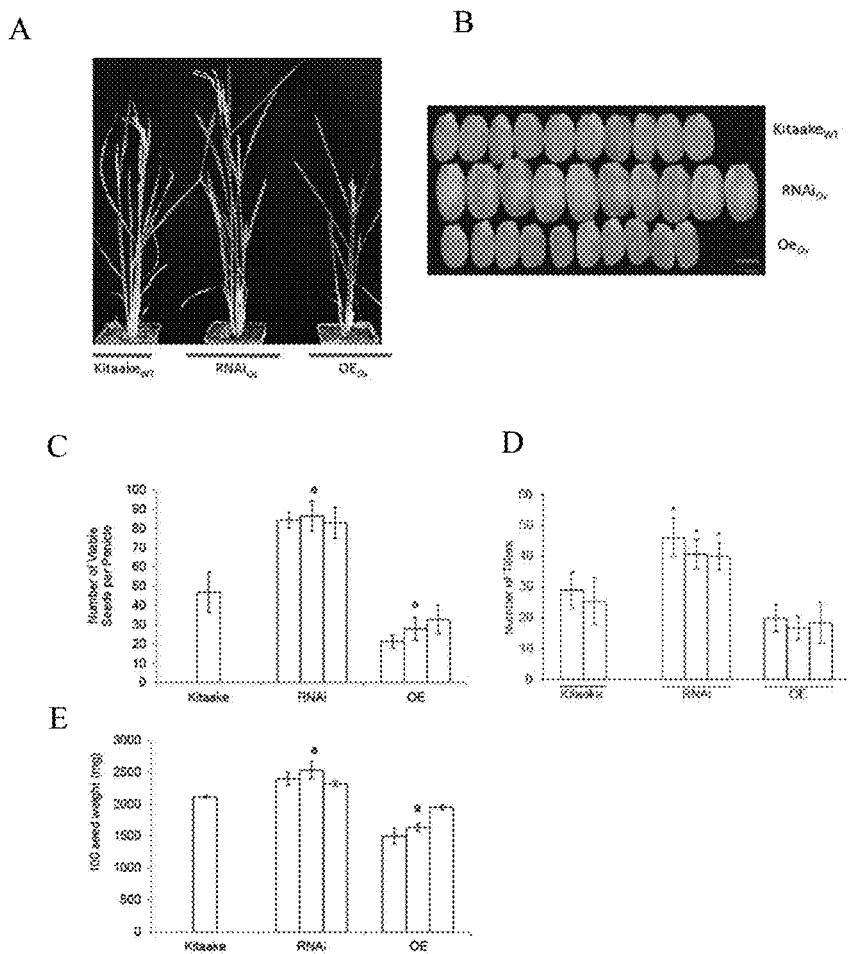

FIG. 14 is data demonstrating rice yield parameters from controlled environment grown plants. Panel A is a photograph showing plantlets of the wild type rice, Kitaake (left), OsLRD7 RNAi line plants (middle), and OsLRD7 overexpression line (right). OsLRD7 is the rice homolog of wheat LRD7. Kitaake plants were used for *Agrobacterium*-mediated transformation to suppress and overexpress OsLRD7 (LOC_Os06g43860). Panel B is a photograph showing ten seeds from Kitaake (top), OsLRD7 RNAi (middle), and OsLRD7 overexpression lines aligned to demonstrate seed size difference. The RNAi lines have larger seeds compared to wild type Kitaake. In addition, OsLRD7 RNAi lines had increased yield due to more viable seeds per panicle than Kitaake (Panel C), increased number of tillers (branches) (Panel D), and an increased 100 seed weight than Kitaake (Panel E). This indicates that suppressing OsLRD7 can increase yield. Data was collected from greenhouse grown plants.

Figure 15B:
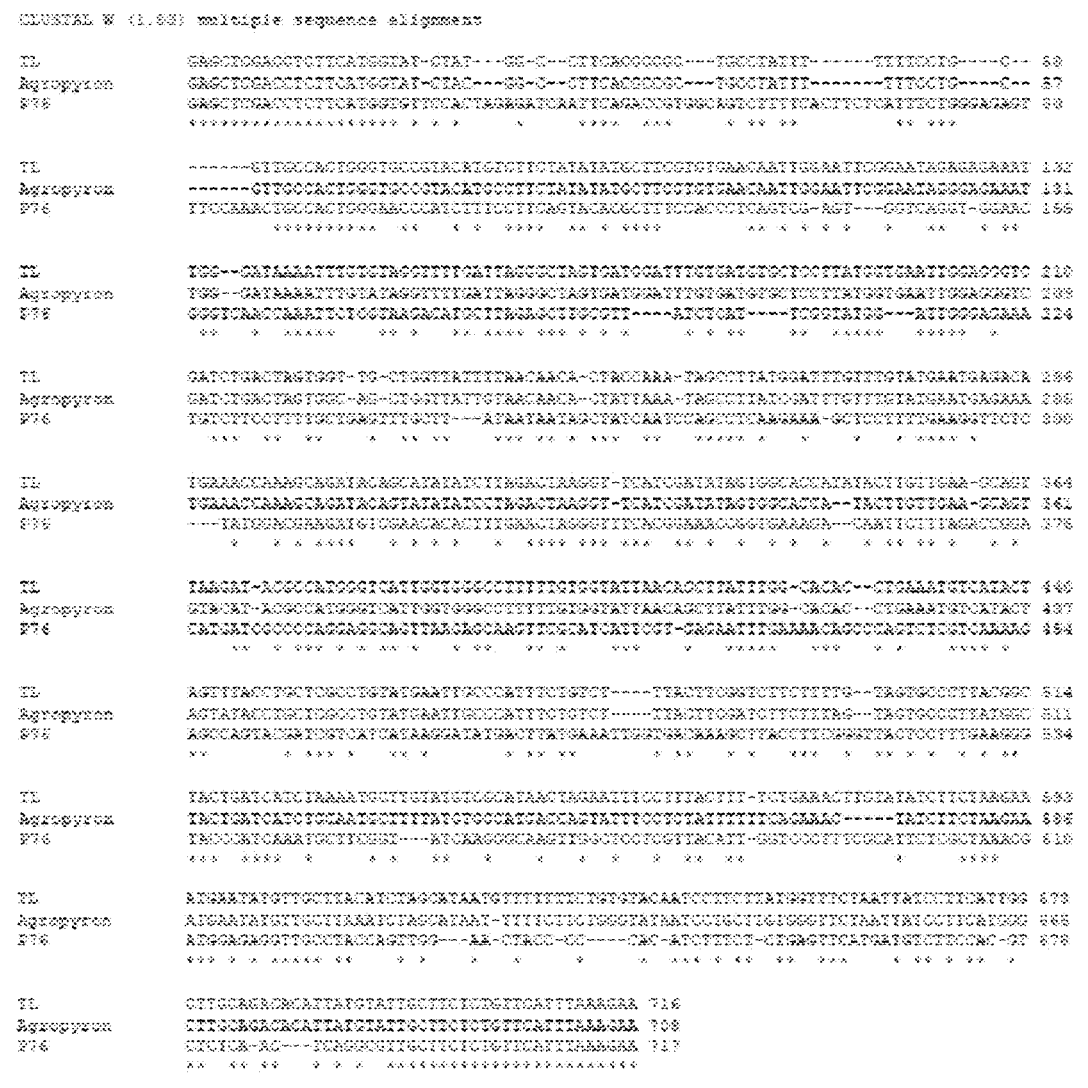

FIG. 15 are sequence alignments. FIG. 15A is an alignment, created using CLUSTALW, between the LRD7 protein from *Agropyron elongatum* (SEQ ID NO:92) and from the P76 (SEQ ID NO:93) and TL (SEQ ID NO:94) lines. The (*) indicates complete homology, while single (.) or double dots (:) indicate lack of homology. The dashes (-) are used to fill-in the missing amino acid residue. The underlined sequences denote conserved domains identified in the coding region (e.g., KNOX2, ELK and homeodomain). 8 non-synonymous single nucleotide polymorphisms (SNPs) and two deletions, both in the P76 sequence, were identified. A single SNP was identified in the homeodomain; ELK and KNOX2 domain sequences were identical among the genotypes. FIG. 15B is an alignment of the promoter region of LRD7 from the translocation line TL (SEQ ID NO:95), the wild relative, *Agropyron elongatum* (SEQ ID NO:96), and P76 (SEQ ID NO:97). The sequence from the *Agropyron elongatum* and the TL line have higher conservation compared to P76, which suggests that the regulatory sequences and LRD7 regulation is conserved between the *Agropyron* line and the TL.

Figure 16:
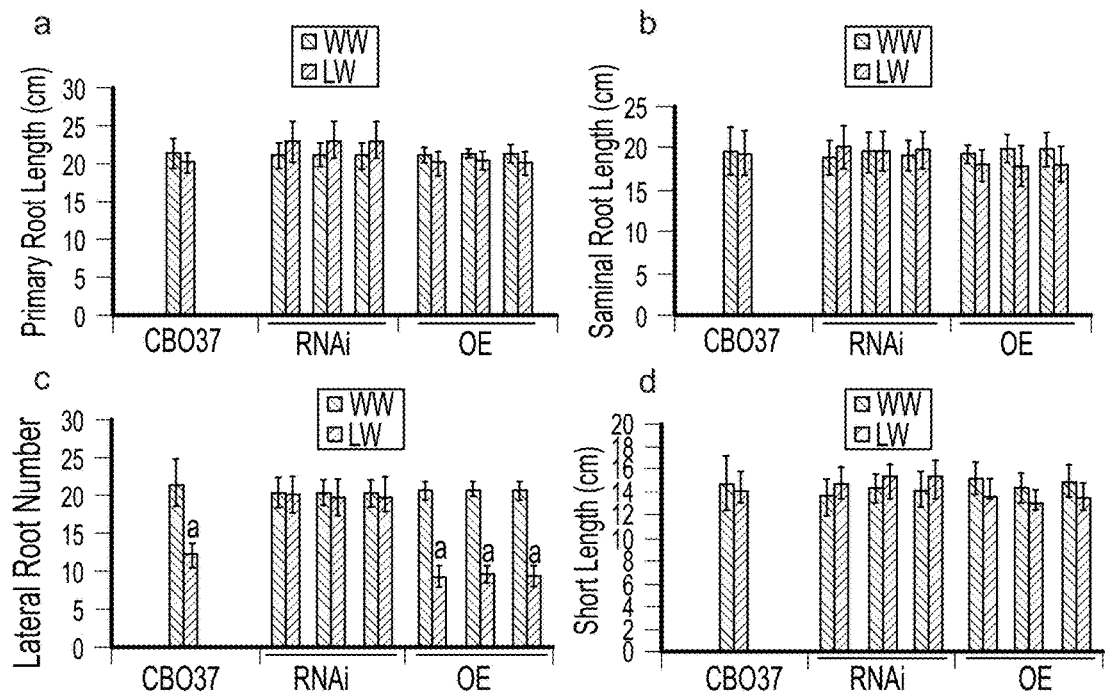

FIG. 16 is data demonstrating that LRD7 negatively regulates lateral root number. Seedlings of wild type (CBO37), 3 RNAi and 3 overexpression events (OE) for LRD7 grown in well watered (WW) and limited water (LW) conditions were assayed for primary root length (Panel a), seminal root length (Panel b), lateral root number on the primary root (Panel c), and shoot length (Panel d) (mean±sd, n=30). A significant decline in lateral root number was observed for CBO37 and OE, but not in the RNAi events in response to LW treatment. "a" indicates significant differences between the WW and LW at $p<0.05$. This data indicates that lateral root number is the major root architecture component affected by LW, and LRD7 maintains lateral root number in LW relative to WW seedlings.

Figure 17:
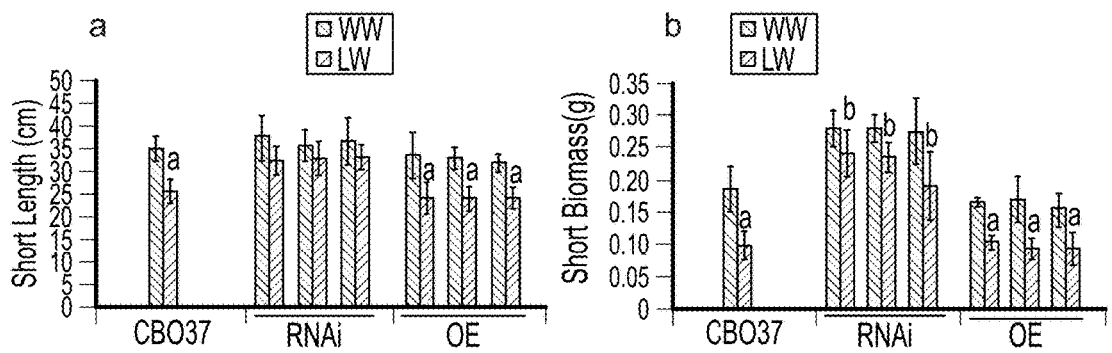

FIG. 17 is data demonstrating that shoot growth is maintained under drought stress in LRD7 RNAi events. Shoot growth was measured in WW and LW condition in pre-tillering stage CBO37, RNAi and OE plants. Shoot length (Panel a) and shoot biomass (dry weight; Panel b) decreased in CBO37 and OE events in LW compared to WW plants (mean±sd, n=30). "a" indicates significant differences between the WW and LW at $p<0.05$ and "b" indicates a significant difference between CBO37 and the RNAi lines in LW at $p<0.05$.

Figure 18:
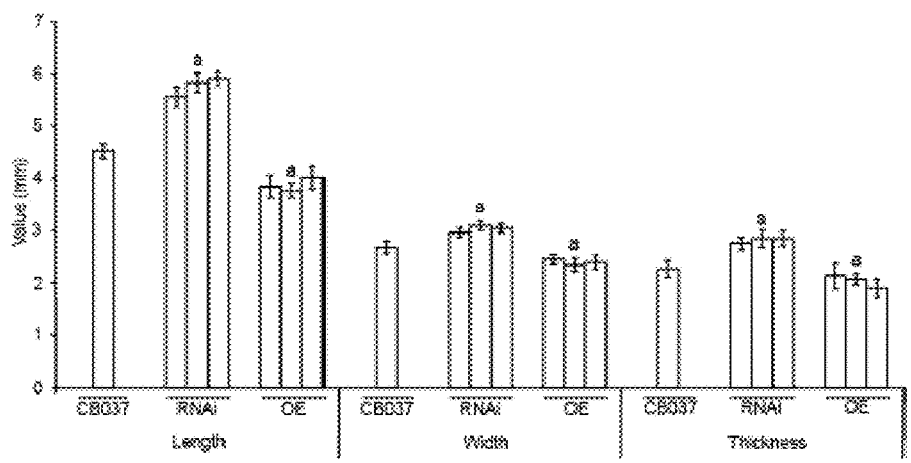

FIG. 18 is data demonstrating that LRD7 negatively regulates seed size in wheat. Seed size (length, width and thickness) from mature plants of CBO37, RNAi and OE events grown in well-watered, optimal greenhouse conditions was measured. The RNAi events had increased seed size compared to CBO37 and the OE events had smaller seed size than CBO37 (n=100, from two independent biological replicates). "a" indicates a significant difference between the CBO37 and the RNAi or OE events at $p<0.05$.

Figure 19:
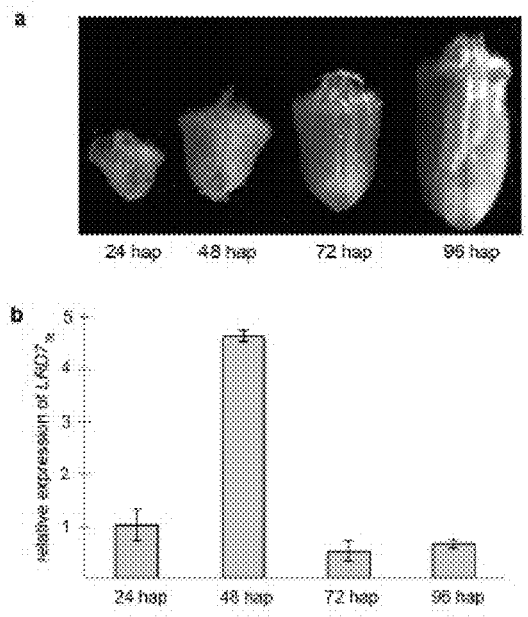

FIG. 19 is data demonstrating that LRD7Ta is expressed during early seed development. The RNAi events for LRD7Ta have larger seed size and the OE events have smaller seeds compared to CBO37. Public wheat gene expression database (PlexDB) indicated that LRD7Ta is expressed in most tissues but its expression is higher during early seed development relative to later stage of developing seed. Panel (a) is a photograph of developing wheat seeds 24, 48, 72 and 96 h after pollination (hap), demonstrating that such seeds exhibit a rapid increase in size after pollination. Panel (b) is a graph showing expression of LRD7Ta, measured during early seed development using qRT-PCR (mean±sd, n=3). It was found that the expression of LRD7Ta peaked at 48 hap, which corresponds to the syncytial stage of wheat endosperm. Syncytial endosperm is characterized by rapidly dividing nuclei and is one of the determinants of seed size. The 24 hap seeds were used as a control to measure relative expression.

Figure 20:
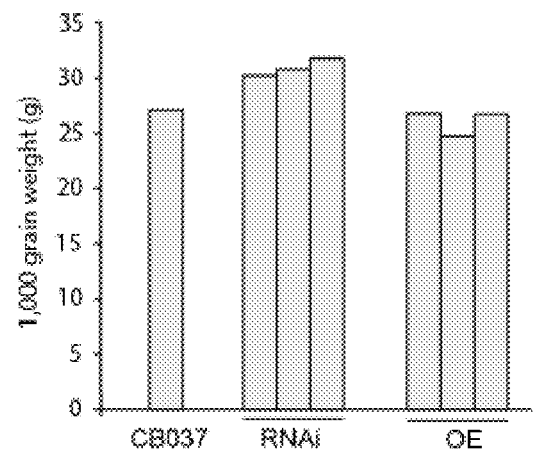

FIG. 20 is a graph showing grain weight improvement in field conditions. The 1,000-grain weight (g) of grains harvested from CBO37, three RNAi and three OE events grown under natural field conditions with no irrigation was measured. The grain weight was obtained from a pool of seeds derived from more than 85 plants for each event and CBO37.

Figure 21:
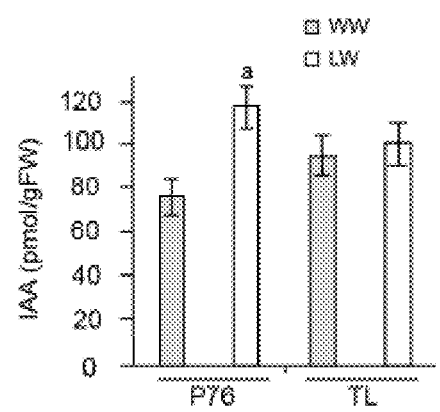

FIG. 21 is a graph showing auxin levels in roots of the P76 and TL lines. IAA levels were measured in the roots from P76 and the TL line under WW and LW conditions. IAA levels increased in P76 under LW but did not change in the TL line. These results indicated that the reduced lateral roots observed in P76 under LW is likely not due to lower IAA in the roots (mean±sd, n=15). "a" indicates a significant difference between the WW and LW treatments at $p<0.05$.

Figure 22:
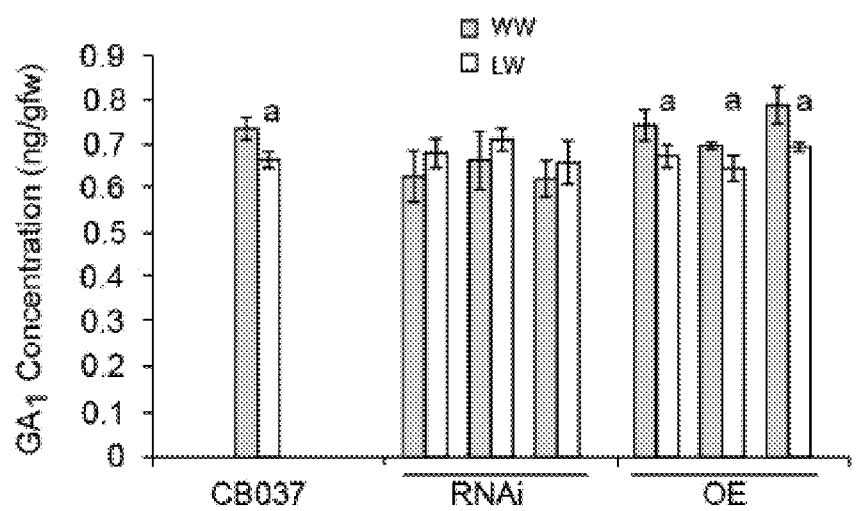

FIG. 22 is a graph showing that root GA1 levels in RNAi events are maintained under low water. GA1 levels were measured in the roots from 6 d seedlings of the CBO37, RNAi and OE events under WW and LW conditions. GA1 decreased in CBO37 and OE roots but did not change in the RNAi roots (mean±sd, n=30). GA1 levels in the RNAi events were similar to the levels in CBO37 and OE events, which suggests that LRD7 could be altering GA sensitivity of the wheat seedlings. "a" indicates a significant difference between the WW and LW treatments at $p<0.05$.

Figure 23:
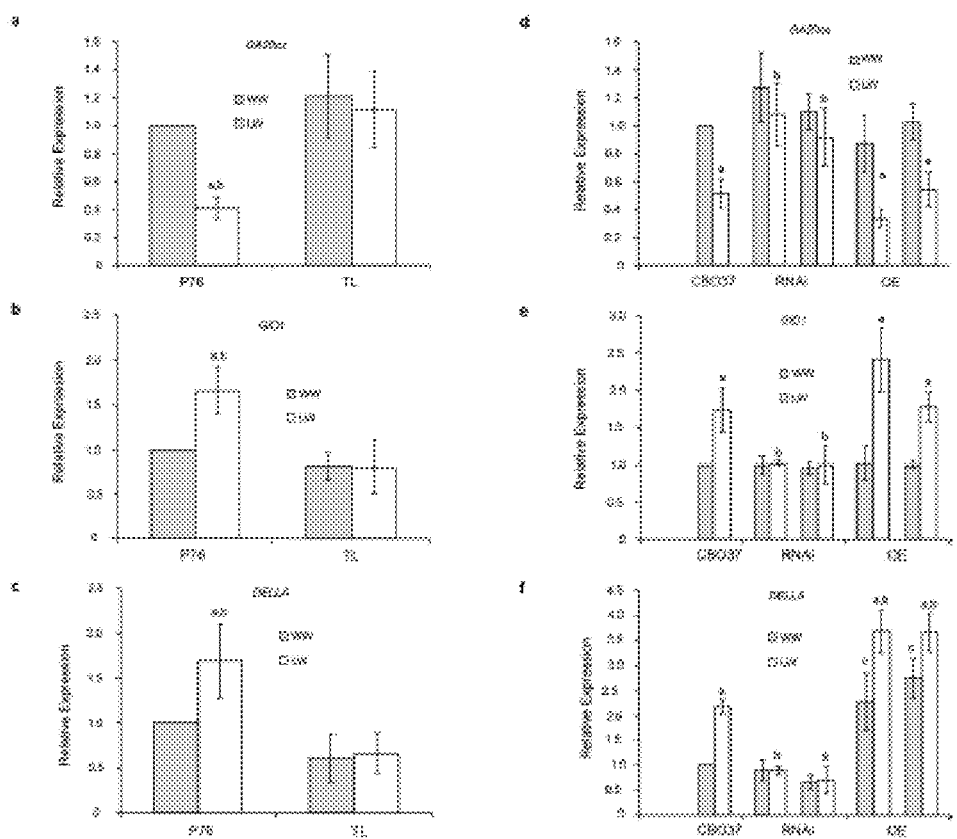

FIG. 23 are graphs showing that expression levels of GA biosynthesis and signaling genes are unaffected in the TL and RNAi roots during water stress. Panels (a)-(c) are graphs showing the relative expression of GA related genes in P76 and TL roots from 6 d old seedlings under WW and LW conditions. Expression values are relative to P76 WW samples used as control (mean±sd, n=3). "a" represents a significant expression difference between WW and LW for a given genotype, and "b" represents a significant difference between P76 and TL in LW at $p<0.05$. Panels (d)-(f) are graphs showing the relative expression of GA-related genes in CBO37, RNAi and OE events in roots from 6 d old seedlings under WW and LW conditions. Expression values are relative to CBO37 WW samples used as control (mean±sd, n=3). "a" represents a significant expression difference between WW and LW for a given genotype, "b" represents a significant difference between CBO37 and RNAi or OE events under LW, and "c" represents a significant expression difference between CBO37 and OE events under WW conditions at $p<0.05$.

Figure 24:
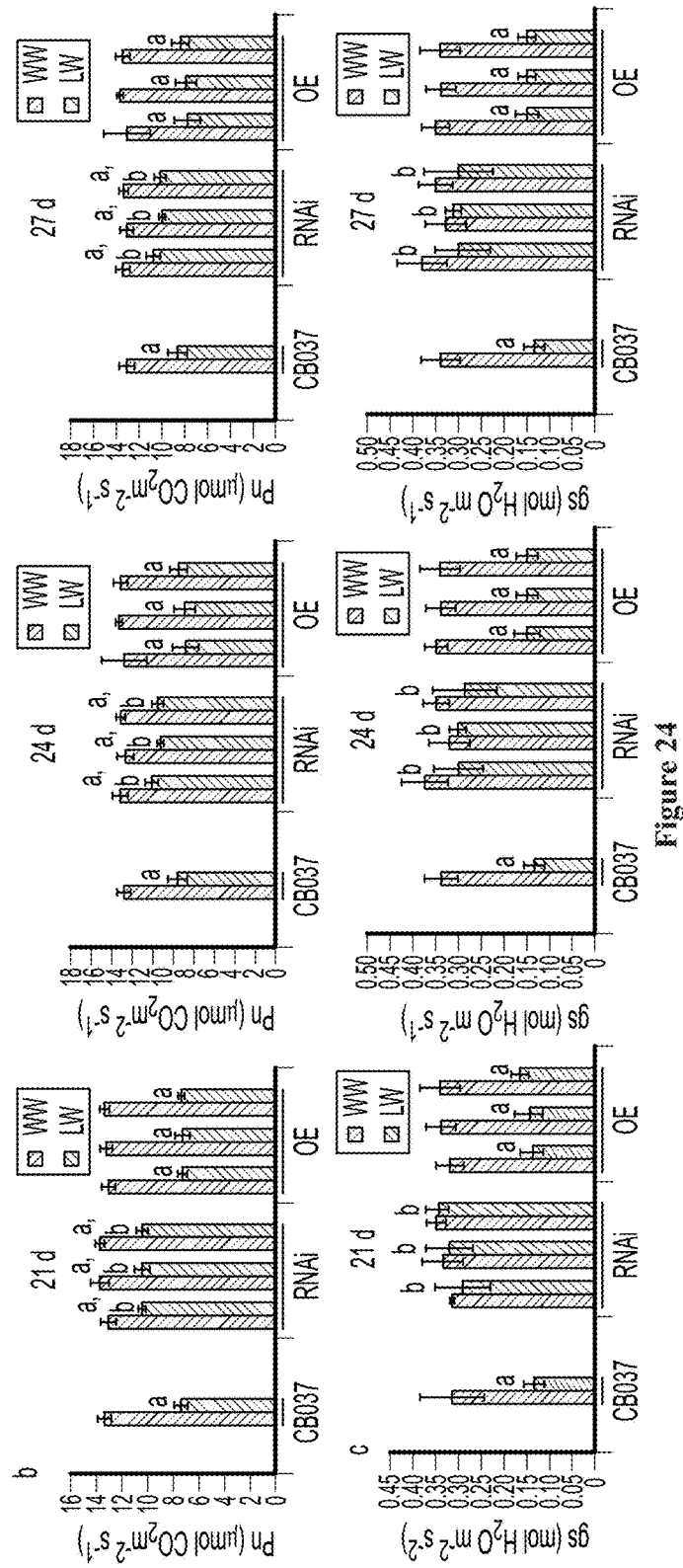

FIG. 24 are graphs showing photosynthetic and stomatal conductance during a progressive drought stress. Panel (a) is a graph showing sand moisture content in the pre-tillering drought stress experiment at 21, 24 and 27 d after transplanting the seedlings from CBO37, RNAi and OE events (mean±sd, n=9). The water availability continues to decline in the LW treatment tubes. Panel (b) is a graph showing that net photosynthetic rate (Pn) declined in all genotypes at 21, 24 and 27 d in response to LW. However, the Pn decline in RNAi events was less than that observed in CBO37 and OE events (mean±sd, n=9). Panel (c) is a graph showing that the LRD7 RNAi events did not experience a drop in the stomatal conductance (gs) at the three time points in LW. "a" indicates significant differences between the WW and LW at p<0.05, and "b" indicates significant (p<0.05) differences between the RNAi or OE and CBO37 in LW.

Figure 25:
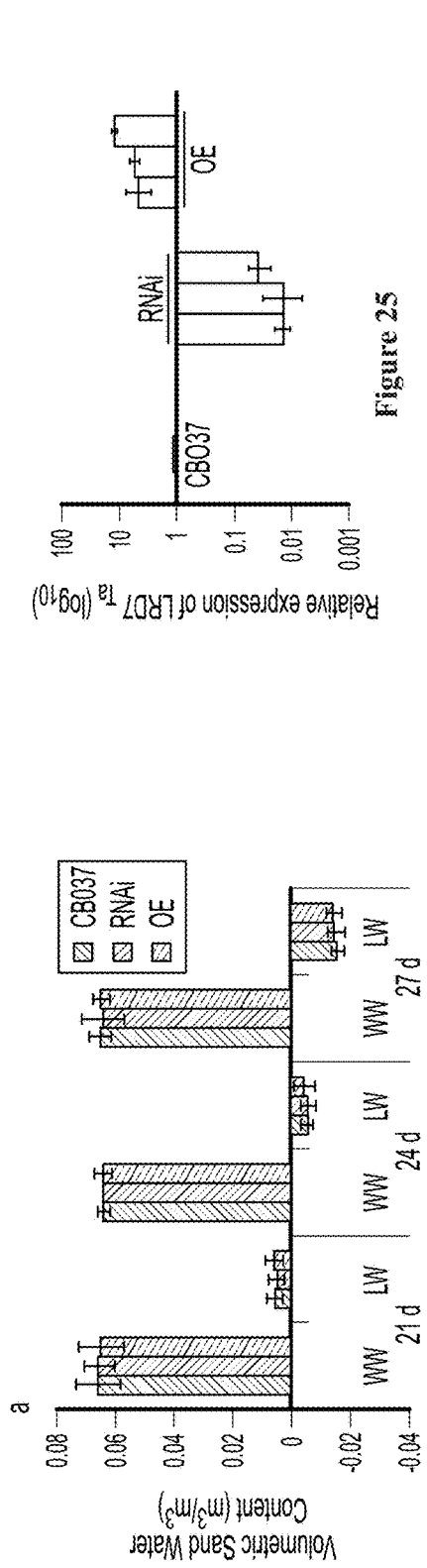

FIG. 25 is a graph showing expression of LRD7Ta in the RNAi and OE events. Gene expression of LRD7Ta from three independent RNAi and OE events used in this study was compared to wild type, CBO37 using qRT-PCR. Expression value of RNAi and OE events are relative to CBO37 expression (set as 1). Leaf tissue from well-watered plants was used for expression analysis (n=3 plants for each independent transgenic event from T2 generation).

Part C

Figure 26:
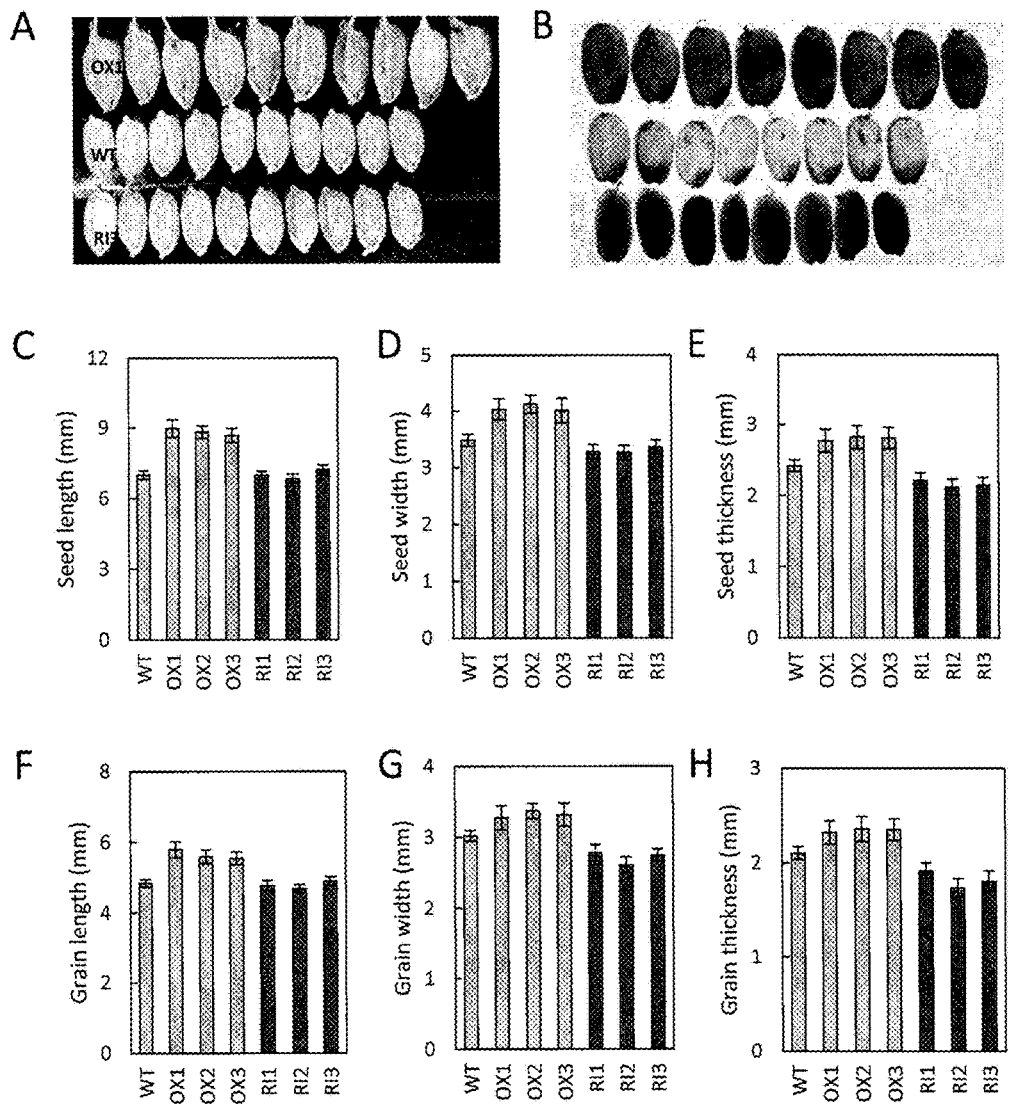

FIG. 26 is data showing the effects of the rice homolog of the E2F-related gene on rice. Panels A and B are photographs showing seed size and grain size, respectively, of plants overexpressing the rice E2F-related sequence (top), wild type plants (middle) and plants expressing an E2F-related RNAi sequence (bottom). Panels C, D, and E are graphs showing seed length, seed width and seed thickness, respectively, and Panels F, G and H are graphs showing the grain length, grain width, and grain thickness, respectively of wild type plants (WT), over-expression plants (OX1, OX2, OX3) and RNAi-expressing plants (RI1, RI2, RI3).

DETAILED DESCRIPTION

This disclosure is based on the discovery that nucleic acids in plants, represented by SEQ ID NO:1 in wheat and SEQ ID NO:3 in rice, and the polypeptides they encode (e.g., SEQ ID NOs: 2 or 4, respectively) are involved in the length of the primary root, the length of the seminal root, lateral root density, and/or root biomass when plants are grown under limiting water conditions (compared to corresponding plants lacking the mutation under corresponding growing conditions). This disclosure also is based on the discovery that the same nucleic acids (e.g., SEQ ID NOs: 1 or 3) and the polypeptides they encode (e.g., SEQ ID NOs: 2 or 4, respectively) are involved in the number of seeds per plant, the average size of the seed, and/or the average weight of the seed when plants are grown under water conditions that are not limiting (compared to a corresponding plant lacking the mutation under corresponding growing conditions).

Based on this discovery, the level of expression of such nucleic acid sequences and/or the function of such polypeptides can be modulated in a number of plant species including, without limitation, *Medicago sativa* (alfalfa), *Hordeum vulgare* (barley), *Phaseolus vulgaris* (beans), *Zea mays* (corn), *Gossypium* spp. (cotton), *Linum usitatissimum* (flax), *Lens culinaris* (lentil), *Elaeis guineensis* (palm), *Pisum sativum* (pea), *Brassica napus* (rapeseed), *Oryza sativa* (rice), *Secale cereal* (rye), *Sorghum bicolor* (sorghum), *Glycine max* (soybean), *Helianthus annuus* (sunflower), *Solanum lycopersicum* (tomato), *Poa pratensis* (Kentucky bluegrass), *Lolium perenne* (Perennial ryegrass), *Festuca arundinacea* (Tall fescue), *Festuca* spp (Fine-leaf fescues), *Agrostis palustris* (Creeping bentgrass), *Cynoden dactylon* (Bermudagrass), *Zoysia japonica* (Zoysia), and *Triticum aestivum* (wheat).

Nucleic Acids and Polypeptides

Representative nucleic acids are provided herein from wheat (see, for example, SEQ ID NO:1) or from rice (see, for example, SEQ ID NO:3). As used herein, nucleic acids can include DNA and RNA, and includes nucleic acids that contain one or more nucleotide analogs or backbone modifications. A nucleic acid can be single stranded or double stranded, which usually depends upon its intended use. The nucleic acids provided herein encode polypeptides (see, for example, SEQ ID NOs: 2 or 4, respectively).

Also provided are nucleic acids and polypeptides that differ from such representative sequences (e.g., SEQ ID NOs: 1 or 3 and SEQ ID NOs: 2 or 4, respectively). Nucleic acids and polypeptides that differ in sequence from SEQ ID NOs: 1 or 3 and SEQ ID NOs: 2 or 4, can have at least 50% sequence identity (e.g., at least 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity) to SEQ ID NOs: 1 or 3 or SEQ ID NOs: 2 or 4, respectively.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity can be performed using the computer program ClustalW and default parameters, which allows alignments of nucleic acid or polypeptide sequences to be carried out across their entire length (global alignment). Chenna et al., 2003, Nucleic Acids Res., 31(13): 3497-500. ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. For fast pairwise alignment of polypeptide sequences, the following parameters can be used: word size: 1; window size: 5; scoring method: percentage; number of top diagonals: 5; and gap penalty: 3. For multiple alignment of polypeptide sequences, the following parameters can be used: weight matrix: blossom; gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid molecule (e.g., SEQ ID NOs: 1 or 3), thereby leading to changes in the amino acid sequence of the encoded polypeptide (e.g., SEQ ID NOs: 2 or 4). For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5(Suppl. 3):345-352), which provides frequency tables for amino acid substitutions), and a non-conservative substitution is one in which an amino acid residue is replaced with an amino acid residue that does not have a similar side chain.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

As used herein, a "purified" polypeptide is a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the polypeptides and naturally occurring molecules with which it is naturally associated. Since a polypeptide that is chemically synthesized is, by nature, separated from the components that naturally accompany it, a synthetic polypeptide is "purified."

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

A vector containing a nucleic acid (e.g., a nucleic acid that encodes a polypeptide) also is provided. Vectors, including expression vectors, are commercially available or can be produced by recombinant DNA techniques routine in the art. A vector containing a nucleic acid can have expression elements operably linked to such a nucleic acid, and further can include sequences such as those encoding a selectable marker (e.g., an antibiotic resistance gene). A vector containing a nucleic acid can encode a chimeric or fusion polypeptide (i.e., a polypeptide operatively linked to a heterologous polypeptide, which can be at either the N-terminus or C-terminus of the polypeptide). Representative heterologous polypeptides are those that can be used in purification of the encoded polypeptide (e.g., 6×His tag, glutathione S-transferase (GST))

Expression elements include nucleic acid sequences that direct and regulate expression of nucleic acid coding sequences. One example of an expression element is a promoter sequence. Expression elements also can include introns, enhancer sequences, response elements, or inducible elements that modulate expression of a nucleic acid. Expression elements can be of bacterial, yeast, insect, mammalian, or viral origin, and vectors can contain a combination of elements from different origins. As used herein, operably linked means that a promoter or other expression element(s) are positioned in a vector relative to a nucleic acid in such a way as to direct or regulate expression of the nucleic acid (e.g., in-frame). Many methods for introducing nucleic acids into host cells, both in vivo and in vitro, are well known to those skilled in the art and include, without limitation, electroporation, calcium phosphate precipitation, polyethylene glycol (PEG) transformation, heat shock, lipofection, microinjection, and viral-mediated nucleic acid transfer.

Vectors as described herein can be introduced into a host cell. As used herein, "host cell" refers to the particular cell into which the nucleic acid is introduced and also includes the progeny of such a cell that carry the vector. A host cell can be any prokaryotic or eukaryotic cell. For example, nucleic acids can be expressed in bacterial cells such as E. coli, or in insect cells, yeast or mammalian cells (such as Chinese hamster ovary cells (CHO) or COS cells). Other suitable host cells are known to those skilled in the art.

Nucleic acids can be detected using any number of amplification techniques (see, e.g., PCR Primer: A Laboratory Manual, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188) with an appropriate pair of oligonucleotides (e.g., primers). A number of modifications to the original PCR have been developed and can be used to detect a nucleic acid.

Nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. discloses suitable Southern blot conditions for oligonucleotide probes less than about 100 nucleotides (Sections 11.45-11.46). The Tm between a sequence that is less than 100 nucleotides in length and a second sequence can be calculated using the formula provided in Section 11.46. Sambrook et al. additionally discloses Southern blot conditions for oligonucleotide probes greater than about 100 nucleotides (see Sections 9.47-9.54). The Tm between a sequence greater than 100 nucleotides in length and a second sequence can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a nucleic acid but not to another nucleic acid if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantitated directly on a membrane or from an autoradiograph using, for example, a PhosphorImager or a Densitometer (Molecular Dynamics, Sunnyvale, Calif.).

Polypeptides can be detected using antibodies. Techniques for detecting polypeptides using antibodies include enzyme linked immunosorbent assays (ELISAs), Western blots, immunoprecipitations and immunofluorescence. An antibody can be polyclonal or monoclonal. An antibody having specific binding affinity for a polypeptide can be generated using methods well known in the art. The antibody can be attached to a solid support such as a microtiter plate using methods known in the art. In the presence of a polypeptide, an antibody-polypeptide complex is formed.

Detection (e.g., of an amplification product, a hybridization complex, or a polypeptide) is usually accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

SEQ ID NO:1 and 3 are predicted to encode polypeptides (e.g., SEQ ID NOs: 2 and 4) that belong to the Lateral Root Density 7 (LRD7) family of sequences that confer drought tolerance through larger roots. LRD7 from wheat has homology to knotted-like3 (KNAT3; At5g25220), a homeobox gene from *Arabidopsis thaliana* that acts as a negative regulator of lateral root development (Truernit et al., 2006, Plant Mol. Biol., 60:1-20; Truernit and Haseloff, 2007, Plant Signal. Behav., 2:10-12). The *Agropyron* allele, LRD7Ag, is down-regulated by drought stress, allowing continued lateral root growth; however, the allele in domesticated wheat, LRD7Ta, is not repressed, thereby limiting root growth and water uptake. In addition to the LRD7 nucleic acid and polypeptide sequences disclosed herein, exemplary related sequences (e.g., those having at least 95% sequence identity) are shown in Accession Nos. BAJ85164.1, BAJ89425.1, AAQ11887.1 and XP_003563314.1.

(*Arabidopsis* KNAT3 nucleic acid sequence)
SEQ ID NO: 7
ATGGCGTTTCATCACAATCATCTCTCACAAGACCTCTCCTTCAATCATTT
CACCGACCAACACCAACCTCCACCTCCGCAACCGCCTCCTCCTCCTCCGC
AACAGCAACAACATTTCCAAGAAGCACCGCCTCCTAATTGGTTAAACACA
GCGCTTCTTCGTTCCTCAGATAACAACAATAACTTCCTCAACCTCCACAC
AGCCACCGCTAACACCACAACCGCAAGCAGCTCCGATTCTCCTTCCTCCG
CCGCCGCCGCCGCCGCTGCTAACCAGTGGCTATCTCGCTCCTCCTCTTTC -continued
CTCCAACGAAACAACAACAACAACGCTTCCATAGTCGGAGATGGGATCGA
TGATGTCACCGGAGGAGCAGACACTATGATTCAGGGAGAGATGAAAACCG
GCGGTGGAGAAAACAAAAACGACGGCGGAGGAGCTACGGCGGCGGATGGA
GTAGTGAGCTGGCAGAATGCGAGACACAAGGCGGAGATCCTTTCGCATCC
TCTTTACGAGCAGCTTTTGTCGGCGCACGTTGCTTGTTTGAGAATCGCGA
CTCCGGTTGATCAGCTTCCGAGAATCGATGCTCAGCTTGCTCAGTCTCAA
CACGTCGTCGCTAAATACTCAGCTTTAGGCGCCGCCGCTCAAGGTCTCGT
CGGCGACGATAAAGAACTTGACCAGTTCATGACACATTATGTGTTGCTAC
TGTGTTCATTTAAAGAGCAATTGCAACAACATGTGCGTGTTCATGCAATG
GAAGCTGTGATGGCTTGTTGGGAGATTGAGCAGTCTCTTCAAAGCTTAAC
AGGAGTGTCTCCTGGAGAAGGGATGGGAGCAACAATGTCTGACGATGAAG
ATGAACAAGTAGAGAGTGATGCTAATATGTTCGATGGGGATTAGATGTG
TTGGGTTTTGGTCCTTTGATTCCTACTGAGAGTGAGAGGTCGTTGATGGA
AAGAGTTAGACAAGAACTTAAACATGAACTCAAACAGGGTTACAAGGAGA
AGATAGTAGACATAAGAGAGGAGATATTAAGGAAGAGAAGAGCTGGGAAG
TTACCAGGAGATACCACCTCTGTTCTCAAAGCTTGGTGGCAATCTCATTC
CAAATGGCCTTACCCTACTGAGGAAGATAAGGCGAGGTTGGTGCAAGAGA
CAGGTTTGCAGCTAAAACAGATAAACAATTGGTTCATCAATCAGAGAAAG
AGGAACTGGCATAGCAATCCATCTTCTTCCACTGTATTGAAGAACAAACG
CAAAAGCAATGCAGGTGACAATAGCGGAAGAGAGCGGTTCGCGTAG (*Arabidopsis* KNAT3 amino acid sequence)
SEQ ID NO: 8
MAFHHNHLSQDLSFNHFTDQHQPPPPQPPPPPPQQQQHFQEAPPPNWLNT
ALLRSSDNNNNFLNLHTATANTTTASSSDSPSSAAAAAAANQWLSRSSSF
LQRNNNNNASIVGDGIDDVTGGADTMIQGEMKTGGGENKNDGGGATAADG
VVSWQNARHKAEILSHPLYEQLLSAHVACLRIATPVDQLPRIDAQLAQSQ
HVVAKYSALGAAAQGLVGDDKELDQFMTHYVLLLCSFKEQLQQHVRVHAM
EAVMACWEIEQSLQSLTGVSPGEGMGATMSDDEDEQVESDANMFDGGLDV
LGFGPLIPTESERSLMERVRQELKHELKQGYKEKIVDIREEILRKRRAGK
LPGDTTSVLKAWWQSHSKWPYPTEEDKARLVQETGLQLKQINNWFINQRK
RNWHSNPSSSTVLKNKRKSNAGDNSGRERFA In addition to LRD7, nucleic acid sequences having homology to E2F-related (E2F) transcription factor and somatic embryogenesis receptor kinase-1 (SERKI) were identified as being involved in regulation of root biomass. E2F transcription factors are a family of proteins that regulate cell cycle progression in plants and animals and, in *Arabidopsis*, is a negative regulator of lateral root formation (del Pozo et al., 2002, Plant Cell, 18:2224-35; Ramirez-Parra et al., 2004, Plant Cell, 16:2350-63). SERK sequences are members of the Leucine-rich repeat, receptor-like kinase protein family and play a role in root differentiation, somatic embryogenesis and gamete development (Walker, 1994, Plant Mol. Biol., 26:1599-609; Schmidt et al., 1997, Develop., 124:2049-62; Somleva et al., 2000, Plant Cell Rep., 19:718-26; Hecht et al., 2001, Plant Physiol., 127: 803-16).

Plants and Methods of Making

Hybrids, varieties, lines, or cultivars are provided that have a mutation in one or more endogenous nucleic acids described herein (e.g., SEQ ID NOs: 1 or 3). As described herein, plants having a mutation in one or more of the endogenous nucleic acids (e.g., SEQ ID NOs: 1 or 3) can exhibit an increase in the length of the primary root, an increase in the length of the seminal root, an increase in lateral root density and/or an increase in root biomass when grown under limiting water conditions, compared to a corresponding plant lacking the mutation under corresponding conditions). In addition, plants having a mutation in one or more of the endogenous nucleic acids (e.g., SEQ ID NOs: 1 or 3) can exhibit an increase in the number of seeds per plant, an increase in the average size of the seed, and/or an increase in the average weight of the seed when grown under water conditions that are not limiting, compared to a corresponding plant lacking the mutation under corresponding conditions).

Methods of making a plant having a mutation are known in the art. Mutations can be random mutations or targeted mutations. For random mutagenesis, plant cells can be mutagenized using, for example, a chemical mutagen, ionizing radiation, or fast neutron bombardment (see, e.g., Li et al., 2001, *Plant J.*, 27:235-42). Representative chemical mutagens include, without limitation, nitrous acid, sodium azide, acridine orange, ethidium bromide, and ethyl methane sulfonate (EMS), while representative ionizing radiation includes, without limitation, x-rays, gamma rays, fast neutron irradiation, and UV irradiation. The dosage of the mutagenic chemical or radiation is determined experimentally for each type of plant tissue such that a mutation frequency is obtained that is below a threshold level characterized by lethality or reproductive sterility. The number of $M_1$ generation seed or the size of $M_1$ plant populations resulting from the mutagenic treatments are estimated based on the expected frequency of mutations. For targeted mutagenesis, representative technologies include TALEN technology (see, for example, Li et al., 2011, *Nucleic Acids Res.*, 39(14):6315-25), zinc-finger technology (see, for example, Wright et al., 2005, *The Plant J.*, 44:693-705), and CRISPR technology (see, for example, Mali et al., 2013, Nature Methods, 10:957-63). Whether random or targeted, a mutation can be a point mutation, an insertion, a deletion, a substitution, or combinations thereof.

Conserved domains in polypeptides can be important for polypeptide function as well as cellular or subcellular location. FIG. 15A shows an alignment of LRD7 coding sequences from *Agropyron elongatum* and from the P76 and TL lines. The underlined sequences denote conserved domains (KNOX2, ELK and homeodomain) in the coding region. FIG. 15B shows an alignment of LRD7 promoter sequences from *Agropyron elongatum* and from the P76 and TL lines.

As discussed herein, one or more nucleotides can be mutated to alter the expression and/or function of the encoded polypeptide, relative to the expression and/or function of the corresponding wild type polypeptide. It will be appreciated, for example, that a mutation in one or more of the highly conserved regions would likely alter polypeptide function, while a mutation outside of those conserved regions would likely have little to no effect on polypeptide function. In addition, a mutation in a single nucleotide can create a stop codon, which would result in a truncated polypeptide and, depending on the extent of truncation, loss-of-function.

A mutation in one of the nucleic acids disclosed herein results in reduced or even complete elimination of LRD7 expression and/or activity in a plant comprising the mutation. Suitable types of mutations include, without limitation, insertions of nucleotides, deletions of nucleotides, or transitions or transversions. In some instances, a mutation is a point mutation; in some instances, a mutation encompasses multiple nucleotides. In some cases, a sequence includes more than one mutation or more than one type of mutation.

For example, a mutation in a promoter sequence can result in reduced or complete elimination of LRD7 expression in a plant comprising the mutation. For example, a mutation in a promoter sequence can alter or eliminate the binding or recognition site of a transcription factor or of the polymerase enzyme, or a mutation in a promoter sequence can alter or eliminate the function of an enhancer, an activator or the like, or a repressor, a silencer or the like. Mutations in a promoter sequence can result in altered or absent transcription, or production of a less-than-functional or non-functional transcript. A less-than-functional or non-functional transcript can result from improper expression (e.g., expressed in the wrong place or at the wrong time), or from degradation of the transcript. Alternatively, a mutation in a promoter sequence may allow transcription to take place, but may interfere with or eliminate the ability of the transcript to be translated.

Mutations in a coding sequence can result in insertions of one or more amino acids, deletions of one or more amino acids, and/or non-conservative amino acid substitutions in the encoded polypeptide. Insertion or deletion of amino acids in a coding sequence, for example, can disrupt the conformation of the encoded polypeptide. Amino acid insertions or deletions also can disrupt sites important for recognition of a binding ligand or for activity of the polypeptide. It is known in the art that the insertion or deletion of a larger number of contiguous amino acids is more likely to render the gene product non-functional, compared to a smaller number of inserted or deleted amino acids. In addition, one or more mutations can change the localization of a polypeptide, introduce a stop codon to produce a truncated polypeptide, or disrupt an active site or domain (e.g., a catalytic site or domain, a binding site or domain) within the polypeptide.

Non-conservative amino acid substitutions can replace an amino acid of one class with an amino acid of a different class. Non-conservative substitutions can make a substantial change in the charge or hydrophobicity of the gene product. Non-conservative amino acid substitutions can also make a substantial change in the bulk of the residue side chain, e.g., substituting an alanine residue for an isoleucine residue. Examples of non-conservative substitutions include a basic amino acid for a non-polar amino acid, or a polar amino acid for an acidic amino acid.

Polypeptides can include particular sequences that determine where the polypeptide is located within the cell, within the membrane, or outside of the cell. Target peptide sequences often are cleaved (e.g., by specific proteases that recognize a specific nucleotide motif) after the polypeptide is localized to the appropriate position. By mutating the target sequence or a cleavage motif, the location of the polypeptide can be altered.

It would be understood by a skilled artisan that mutations also can include larger mutations such as, for example, deletion of most or all of the promoter, deletion of most of all of the coding sequence, or deletion or translocation of the chromosomal region containing some or all of the LRD7 sequences. It would be understood, however, that, the larger the mutation, the more likely it is to have an effect on other traits as well.

Following mutagenesis, $M_0$ plants are regenerated from the mutagenized cells and those plants, or a subsequent generation of that population (e.g., $M_1$, $M_2$, $M_3$, etc.), can be screened for a mutation in a sequence of interest (e.g., SEQ ID NOs: 1 or 3). Screening for plants carrying a mutation in a sequence of interest can be performed using methods routine in the art (e.g., hybridization, amplification, combinations thereof) or by evaluating the phenotype of the plants (e.g., the length of the primary root, the length of the seminal root, lateral root density, root biomass, the number of seeds per plant, the average size of the seed, and/or the average weight of the seed). Generally, the presence of a mutation in one or more of the nucleic acid sequences disclosed herein (e.g., SEQ ID NOs: 1 or 3) results in an increase in the length of the primary root, an increase in the length of the seminal root, an increase in lateral root density, and/or an increase in root biomass under limiting water conditions, or an increase in the number of seeds per plant, an increase in the average size of the seed and/or an increase in the average weight of the seed under water conditions that are not limiting, compared to a corresponding plant (e.g., having the same varietal background) lacking the mutation under corresponding conditions.

As used herein, an "increase" in the length of the primary root, the length of the seminal root, in lateral root density, and/or in root biomass under limiting water conditions, or in the number of seeds per plant, the average size of the seed and/or the average weight of the seed under water conditions that are not limiting, refers to an increase (e.g., a statistically significant increase) in the indicated feature under the indicated water condition by at least about 5% up to about 95% (e.g., about 5% to about 10%, about 5% to about 20%, about 5% to about 50%, about 5% to about 75%, about 10% to about 25%, about 10% to about 50%, about 10% to about 90%, about 20% to about 40%, about 20% to about 60%, about 20% to about 80%, about 25% to about 75%, about 50% to about 75%, about 50% to about 85%, about 50% to about 95%, and about 75% to about 95%) relative to the same feature from a corresponding plant lacking the mutation grown under corresponding conditions. As used herein, statistical significance refers to a p-value of less than 0.05, e.g., a p-value of less than 0.025 or a p-value of less than 0.01, using an appropriate measure of statistical significance, e.g., a one-tailed two sample t-test.

An $M_1$ plant may be heterozygous for a mutant allele and exhibit a wild type phenotype. In such cases, at least a portion of the first generation of self-pollinated progeny of such a plant exhibits a wild type phenotype. Alternatively, an $M_1$ plant may have a mutant allele and exhibit a mutant phenotype. Such plants may be heterozygous and exhibit a mutant phenotype due to a phenomenon such as dominant negative suppression, despite the presence of the wild type allele, or such plants may be homozygous due to independently induced mutations in both alleles.

A plant carrying a mutant allele can be used in a plant breeding program to create novel and useful cultivars, lines, varieties and hybrids. Thus, in some embodiments, an $M_1$, $M_2$, $M_3$ or later generation plant containing at least one mutation is crossed with a second plant, and progeny of the cross are identified in which the mutation(s) is present. It will be appreciated that the second plant can contain the same mutation as the plant to which it is crossed, a different mutation, or be wild type at the locus. Additionally or alternatively, a second line can exhibit a phenotypic trait such as, for example, disease resistance, high yield, leaf quality, height, plant maturation, stalk size, and/or leaf number per plant.

Breeding is carried out using known procedures. DNA fingerprinting, SNP or similar technologies may be used in a marker-assisted selection (MAS) breeding program to transfer or breed mutant alleles into other lines, varieties or cultivars, as described herein. Progeny of the cross can be screened for a mutation using methods described herein, and plants having a mutation in a nucleic acid sequence disclosed herein (e.g., SEQ ID NOs: 1 or 3) can be selected. For example, plants in the $F_2$ or backcross generations can be screened using a marker developed from a sequence described herein or a fragment thereof, using one of the techniques listed herein. Plants also can be screened for the length of the primary root, the length of the seminal root, in lateral root density, and/or in root biomass under limiting water conditions, or in the number of seeds per plant, the average size of the seed and/or the average weight of the seed under water conditions that are not limiting, and those plants having one or more of such phenotypes, compared to a corresponding plant that lacks the mutation, can be selected. Plants identified as possessing the mutant allele and/or the mutant phenotype can be backcrossed or self-pollinated to create a second population to be screened. Backcrossing or other breeding procedures can be repeated until the desired phenotype of the recurrent parent is recovered.

Successful crosses yield $F_1$ plants that are fertile and that can be backcrossed with one of the parents if desired. In some embodiments, a plant population in the $F_2$ generation is screened for the mutation or variant gene expression using standard methods (e.g., PCR with primers based upon the nucleic acid sequences disclosed herein). Selected plants are then crossed with one of the parents and the first backcross ($BC_1$) generation plants are self-pollinated to produce a $BC_1F_2$ population that is again screened for variant gene expression. The process of backcrossing, self-pollination, and screening is repeated, for example, at least four times until the final screening produces a plant that is fertile and reasonably similar to the recurrent parent. This plant, if desired, is self-pollinated and the progeny are subsequently screened again to confirm that the plant contains the mutation and exhibits variant gene expression. Breeder's seed of the selected plant can be produced using standard methods including, for example, field testing, genetic analysis, and/or confirmation of the phenotype.

The result of a plant breeding program using the mutant plants described herein are novel and useful cultivars, varieties, lines, and hybrids. As used herein, the term "variety" refers to a population of plants that share constant characteristics which separate them from other plants of the same species. A variety is often, although not always, sold commercially. While possessing one or more distinctive traits, a variety is further characterized by a very small overall variation between individual with that variety. A "pure line" variety may be created by several generations of self-pollination and selection, or vegetative propagation from a single parent using tissue or cell culture techniques. A "line," as distinguished from a variety, most often denotes a group of plants used non-commercially, for example, in plant research. A line typically displays little overall variation between individuals for one or more traits of interest, although there may be some variation between individuals for other traits.

Depending on the plant, hybrids can be produced by preventing self-pollination of female parent plants (i.e., seed parents) of a first variety, permitting pollen from male parent plants of a second variety to fertilize the female parent plants, and allowing $F_1$ hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), nuclear male sterility, genetic male sterility, molecular male sterility wherein a transgene inhibits microsporogenesis and/or pollen formation, or self-incompatibility. Female parent plants containing CMS are particularly useful. In embodiments in which the female parent plants are CMS, the male parent plants typically contain a fertility restorer gene to ensure that the $F_1$ hybrids are fertile. In other embodiments in which the female parents are CMS, male parents can be used that do not contain a fertility restorer. $F_1$ hybrids produced from such parents are male sterile. Male sterile hybrid seed can be interplanted with male fertile seed to provide pollen for seed-set on the resulting male sterile plants.

Varieties, lines and cultivars described herein can be used to form single-cross $F_1$ hybrids. In such embodiments, the plants of the parent varieties can be grown as substantially homogeneous adjoining populations to facilitate natural cross-pollination from the male parent plants to the female parent plants. The $F_2$ seed formed on the female parent plants is selectively harvested by conventional means. One also can grow the two parent plant varieties in bulk and harvest a blend of $F_1$ hybrid seed formed on the female parent and seed formed upon the male parent as the result of self-pollination. Alternatively, three-way crosses can be carried out wherein a single-cross $F_1$ hybrid is used as a female parent and is crossed with a different male parent. As another alternative, double-cross hybrids can be created wherein the $F_1$ progeny of two different single-crosses are themselves crossed. Self-incompatibility can be used to particular advantage to prevent self-pollination of female parents when forming a double-cross hybrid.

In addition to mutation, another way in which LRD7 expression can be reduced or knocked-out is to use inhibitory RNAs (e.g., RNAi). Therefore, transgenic plants are provided that contain a transgene encoding at least one RNAi molecule, which, when expressed, silences at least one of the endogenous nucleic acids described herein (e.g., SEQ ID NOs: 1 or 3). As described herein, such transgenic plants exhibit an increase in the length of the primary root, an increase in the length of the seminal root, an increase in lateral root density, and/or an increase in root biomass under limiting water conditions, or an increase in the number of seeds per plant, an increase in the average size of the seed and/or an increase in the average weight of the seed under water conditions that are not limiting (e.g., compared to a plant lacking or not expressing the RNAi).

RNAi technology is known in the art and is a very effective form of post-transcriptional gene silencing. RNAi molecules typically contain a nucleotide sequence (e.g., from about 18 nucleotides in length (e.g., about 19 or 20 nucleotides in length) up to about 700 nucleotides in length) that is complementary to the target gene in both the sense and antisense orientations. The sense and antisense strands can be connected by a short "loop" sequence (e.g., about 5 nucleotides in length up to about 800 nucleotides in length) and expressed in a single transcript, or the sense and antisense strands can be delivered to and expressed in the target cells on separate vectors or constructs. A number of companies offer RNAi design and synthesis services (e.g., Life Technologies, Applied Biosystems), and representative RNAi molecules to the sequences described herein are provided in SEQ ID NOs: 5 and 6.

The RNAi molecule can be expressed using a plant expression vector. The RNAi molecule typically is at least 25 nucleotides in length and has at least 91% sequence identity (e.g., at least 95%, 96%, 97%, 98% or 99% sequence identity) to one of the nucleic acid sequences disclosed herein (e.g., SEQ ID NOs: 1 or 3) or hybridizes under stringent conditions to one of the nucleic acid sequences disclosed herein (e.g., SEQ ID NOs: 1 or 3). Hybridization under stringent conditions is described above.

Methods of introducing a nucleic acid (e.g., a heterologous nucleic acid) into plant cells are known in the art and include, for example, particle bombardment, *Agrobacterium*-mediated transformation, microinjection, polyethylene glycol-mediated transformation (e.g., of protoplasts, see, for example, Yoo et al. (2007, *Nature Protocols*, 2(7):1565-72)), liposome-mediated DNA uptake, or electroporation. Following transformation, the transgenic plant cells can be regenerated into transgenic plants. As described herein, expression of the transgene results in plants that exhibit an increase in the length of the primary root, an increase in the length of the seminal root, an increase in lateral root density, and/or an increase in root biomass under limiting water conditions, or an increase in the number of seeds per plant, an increase in the average size of the seed and/or an increase in the average weight of the seed under water conditions that are not limiting, relative to a plant not expressing the transgene. The regenerated transgenic plants can be screened for the length of the primary root, the length of the seminal root, lateral root density, and/or root biomass under limiting water conditions, or the number of seeds per plant, the average size of the seed and/or the average weight of the seed under water conditions that are not limiting, compared to a corresponding non-transgenic plant, and can be selected for use in, for example, a breeding program as discussed herein.

The sequences described herein can be overexpressed in plants, if so desired. Therefore, transgenic plants are provided that are transformed with a nucleic acid molecule described herein (e.g., SEQ ID NOs: 1 or 3) or a functional fragment thereof under control of a promoter that is able to drive expression in plants (e.g., a plant promoter). As discussed herein, a nucleic acid molecule used in a plant expression vector can have a different sequence than a sequence described herein, which can be expressed as a percent sequence identity (e.g., relative to SEQ ID NOs: 1 or 3) or based on the conditions under which sequences hybridize (e.g., to SEQ ID NOs: 1 or 3). As an alternative to using a full-length sequence, a portion of the sequence can be used that encodes a polypeptide fragment having the desired functionality (referred to herein as a "functional fragment"). When used with respect to nucleic acids, it would be appreciated that it is not the nucleic acid fragment that possesses functionality but the encoded polypeptide fragment.

Following transformation, the transgenic cells can be regenerated into transgenic plants, which can be screened for the length of the primary root, the length of the seminal root, lateral root density, and/or root biomass under limiting water conditions, or the number of seeds per plant, the average size of the seed and/or the average weight of the seed under water conditions that are not limiting, and plants having increased amounts of at least one of such features, compared to the feature in a corresponding non-transgenic plant, can be selected and used, for example, in a breeding program as discussed herein.

Food or Feed Products and Methods of Making

The plants described herein (e.g., exhibiting an increase in the length of the primary root, an increase in the length of the seminal root, an increase in lateral root density, and/or an increase in root biomass when grown under limiting water conditions, or exhibiting an increase in the number of seeds per plant, an increase in the average size of the seed, and/or an increase in the average weight of the seed when grown under water conditions that are not limiting, compared to a corresponding plant lacking the mutation under corresponding conditions) or portions thereof (e.g., seed or grain, seed oil, or leaf) can be used in food products for consumption by humans or in feed products for consumption by companion animals or animals raised for commercial purposes. In addition, the plants described herein also exhibited an increase in shoot biomass under limiting water conditions, which can be used to increase the above-ground biomass for use with turf grasses or in plants that are useful in the production of biofuels or bioenergy.

The plants described herein or portions thereof can be used in food products for human consumption. Food products can be, without limitation, pasta (e.g., spaghetti), a baked product (e.g., bread, cake, cookies, or biscuits), a snack food (e.g., chips, crackers, energy bars, or energy drinks), or a meat (e.g., chicken, pork, beef, or fish). In addition, the plants described herein or portions thereof can be used in feed products for animal consumption. Animals can be a companion animal (e.g., dogs, cats, birds, fish, potbelly pigs, reptiles, amphibians, and rodents) or an animal raised for commercial purposes (e.g., chickens, turkeys, game birds, cattle, fish, pigs, sheep, wild birds, frogs, shrimp, snails, reptiles, amphibians, and rodents).

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Part A

Example 1—Plant Material

The translocation line (TL) and the P76 line used in this study were obtained from A. J. Lukaszewski, University of California, Riverside. These included a third generation derivative of the original wheat-*Agropyron* translocation chromosome produced by E. R. Sears (Sears, 1978, Proc. $8^{th}$ Congress of Eucarpia II Interspecific Gene Transfer, 63-72) and controls. The starting chromosome Transfer #1 (Sears, supra) was generated by the phI b-induced homoeologous recombination and it consists of normal 7DS, a short proximal segment of 7DL and a long distal segment of *A. elongatum* chromosome 7EL. A line of cv. Chinese Spring homozygous for Transfer #1 was crossed and backcrossed three times to cv. Pavon 76. The last two backcrosses were to a phI b line of Pavon, resulting in several plants heterozygous for Transfer #1 and homozygous for the phib mutation. These plants were grown, self-pollinated and their progenies screened to identify secondary wheat-*Agropyron* recombinant chromosomes. Among many such chromosomes isolated there was chromosome labeled 1-96 (Zhang et al., 2005, TAG, 111:573-82).

Figure 1:
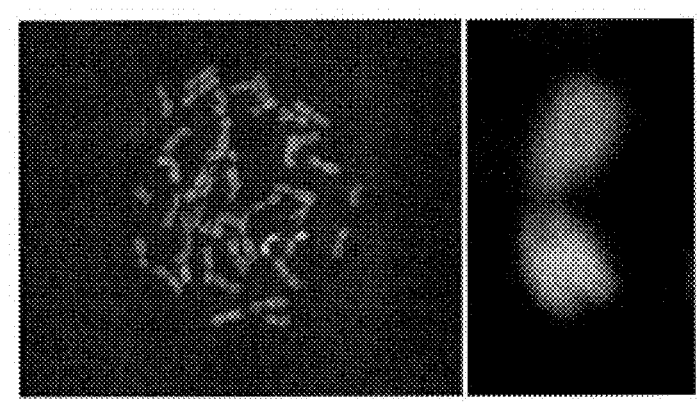
FIG. 1 are images of the wheat-*Agropyron elongatum* (7Ag.7DL) translocation. A CIMMYT hexaploid wheat cultivar Pavon76 carrying a chromosome 7 segment from *Agropyron elongatum* (7Ag.7DL) is visualized by genomic in situ hybridization. In both images (right and left), green staining represents the translocated segment from *Agropyron*. Wheat genomic probe was directly labeled with rhodamine (red). Root system architecture analysis was performed on the background parent, Pavon76, the Pavon76 (7Ag.7DL) translocation line and a segregating null line.

Chromosome 1-96 is essentially a normal chromosome 7D of wheat with terminal segment of the long arm, perhaps 20% in length, originating from 7E of *A. elongatum*. The *A. elongatum* segment carries Lr 19 and Y. This chromosome was again combined with the phI b mutation in cv. Pavon 76 and a tertiary recombinant chromosome was recovered, labeled 1-96-1. This chromosome differs from 1-96 by the absence of the terminal *A. elongatum* segment that normally carries the Y locus. The translocated chromosome 1-96-1 has a normal 7DS arm, long (ca. 75%) proximal segment of 7DL, a homeologous segment from TEL of *A. elongatum* and a short terminal segment of 7DL (FIG. 1). Since the chromosome was produced by crossing over it is assumed to be fully compensating for normal 7D. No indications of reduced compensation have been observed.

After recovery, plants with chromosome 1-96-1 were backcrossed additional three times to cv. Pavon 76 and two sets of sister lines were isolated among progenies from self-pollinated BC3 heterozygotes: homozygotes for the 1-96-1 translocations and disomics of normal chromosomes 7D. These two are sister lines that differ by the presence/absence of the *A. elongatum* segment; disomics 7D serve as additional controls for the translocation lines. Overall, the recovered lines have eight backcrosses to Pavon 76; however, it needs to be taken into account that the phI b lines carry substantial and extensive genome rearrangements, and new ones are generated in each generation. There were only three backcrosses to normal Pavon 76 after the last round of the phI b-induced recombination. For this reason, additional controls in the form of sister lines are highly desirable. For simplicity, the line of cv. Pavon 76 homozygous for the 1-96-1 translocation will be referred to as TL (translocation line), original cv. Pavon 76 will be abbreviated as P76 while the sister lines of TL without the translocation will be called NC (negative control). Nulli-tetrasomics (NT) for the homoeologous group 7 as well as ditelosomics (Dt) lines of chromosome 7D in cv. Chinese spring were used to determine and verify the chromosome locations of various candidate genes.

Example 2—Cigar Roll Root Assays

For the early seedling stage root screening we used the cigar roll method (Zhu et al., 2006, TAG, 113:1-10). Similar sized seeds were germinated in a petri dish with moist paper towel for three days in the dark at 22-2S° C. Three seedlings per genotype were placed between two sheets of germination paper and rolled vertically. Three batches of 10 cigar rolls, totaling 30 plants per genotype were soaked in tap water and placed vertically in 1 L beaker filled with SO mL of water. Seedlings were grown in a controlled environment using a Percival Intellus Control System incubator (Model: I36VLC8) set at 25/27° C., 11.5/12.5 h day/night, 50/70% relative humidity and illumination of 80 µmols $m^{-2}$ $sec^{-1}$ during the duration of the experiments (Percival Scientific, Inc., Iowa). Water was added to each beaker twice daily to maintain the volume of 50 ml. All measurements were carried until 6 days after germination. Measurements after Day 6 can potentially be affected by limiting seed resources that drive seedling growth. For gene expression experiments, seedlings were harvested at 2, 4 and 6 days after germination. Root tissue samples were collected and snap frozen.

Example 3—Greenhouse Experiments

Seeds were germinated in glass petri dishes in the dark at 25° C. Once the coleoptiles were approximately 1 cm, uniform seedlings were selected and transplanted to PVC pipes (1 m×15.5 cm; height×diameter; NDS Inc., Texas). Each pipe was lined with clear poly plastic bags (length× width; 153 cm×18.5 cm) (Uline, Tex.) and filled with approximately 9 Kg of fine silica sand (Lane Mountain Co., Valley, Wash.). A gap was maintained between the plastic bags and the inner wall of the pipes. Small holes were made at the side and bottom of the plastic bags as well as the pipes to provide adequate aeration and drainage. For the first week after transplant, each tube was watered daily with 100 mL. After the first week, the well-watered, control plants were supplied with 50 mL of tap water and 50 mL of half strength Hoagland solution twice weekly. For the limited-water treatment, each tube received 50 mL of half-strength Hoagland solution twice weekly. Each treatment consisted of seven replicates per genotype with five plants per tube/replicate (35 plants per treatment).

The pre-tillering stage experiment was done from July 2011 to October 2011. The greenhouse temperature was set between 26.7-32.2° C. during the day and 26.1-29.4° C. during the night, humidity ranges from 33%-73% and light period was between 0700-1800 hrs by Metal Halide Lamp 1000 watt bulbs (Philips Lighting Co., Somerset, N.J.).

Using the LI-250A Light Meter, the average light reading is 215.8±44.5 µmol s$^{-1}$ m$^{-2}$ (LI-COR Biosciences, Lincoln, Nebr., USA).

Wheat roots were harvested 18 days after germination. The plastic sleeve was carefully removed from each tube and the plastic lining was cut gently to avoid root damage. Roots were gently removed from the sand column. Excess sand was removed using a paint brush with soft bristles. Root and shoot length were recorded. Root and shoot dry weights were determined after drying for 5 days at 60° C. Statistical analyses were done using the one-way ANOVA function using Tukey's method using R-Commander package for R (Fox, 2005, J. Statistical Software, 14).

Example 4—Chlorophyll Fluorescence, Photosynthesis and Gas Exchange Measurements Chlorophyll fluorescence measurements were recorded day 18 after transplant for each treatment on the leaf below the newest fully expanded leaf using a portable photosynthesis system (LI-COR 6400xt) equipped with a leaf chamber fluorometer (LI-COR 6400-40) (LI-COR Biosciences). The area of each leaf in the leaf chamber was determined and values entered manually into the system. Measurements were recorded between 1000 hrs-14:00 hrs. Reference $CO_2$ levels were maintained at 400 µmol sec$^{-1}$ and chamber flow was set at 500 µmol. Actinic light intensity was set at 1000 µmol with 10% blue LEDs. Maximal fluorescence values of light adapted leaves were obtained by saturating the leaf using a multiphase flash (Loriaux et al., 2006, Am. Soc. Plant Biol. Ann. Meet., Poster Presentation). The first phase consisted of an 8000 µmol pulse for 300 ms followed by a 100% ramp for 400 ms, and a second saturating flash of 8000 µmol for 300 ms. The maximum quantum efficiency of PSII (Fv'/Fm') was calculated using the equation: Fv'/Fm'=Fm'-Fo'/Fm', where Fv' refers to variable fluorescence, Fm' is maximal fluorescence, Fo' is minimum fluorescence, and Fs is the steady state fluorescence. Photochemical quenching (qP) was calculated using the equation: Fm'-Fs'/Fm'-Fo'. Non-photochemical quenching (qN) was determined using the equation: =Fm-Fm'/Fm-Fo'.

Example 5—A/Ci Curve with Chlorophyll Fluorescence

Gas exchange and fluorescence measurements were recorded for each replicate with the LI-COR 6400xt using PVC-cultured wheat plants on day 18 day. Instrument settings were identical to those described above. Six $CO_2$ response curves per genotype were generated for each treatment. Gas exchange and fluorescence measurements were recorded at 13 $CO_2$ flow rates (400, 300, 200, 100, 50, 100, 150, 200, 300, 400, 500, 600, and 800 µmol sec$^{-1}$). $CO_2$ assimilation was plotted against intercellular $CO_2$ ($C_i$) and the data points were fit to the equation of Farquhar et al. (1980, Planta, 149:78-90) using SAS and the methods described by Dubois et al. (2007, New Phytol., 176:402-14).

Example 6—RNA Isolation and RNA Cleanup

Eighteen days after transplanting, leaf and root tissues were collected and snap frozen in liquid nitrogen for RNA extraction. RNA was extracted using the TRIzol method. RNA concentration was quantified (1:1000) with Beckman Coulter DU 730 Life Science UV/Vis Spectrophotometer (Beckman Coulter, Brea, Calif.). RNA cleanup was performed according to RNeasy MinElute Cleanup kit protocol (Qiagen, Valencia, Calif.). The RNA was eluted with 15 µl RNase-free water along with on-column DNase1 treatment.

Example 7—First-Strand cDNA Synthesis and qRT-PCR Reaction

We used SuperScript VILO to synthesize cDNA for semi- and real-time quantitative PCR (qPCR) (Invitrogen Corp., Carlsbad, Calif.). First-strand cDNA was generated for the two-step qRT-PCR by following the protocol from Superscript VILO cDNA synthesis kit. An amount of 2 µg of RNA was used in the 20 µL reaction mixture. For the qPCR reaction, 4 µL of the diluted cDNA (1:20) was used in the 15 µL reaction mixture. In the qPCR reaction volume, 7.5 µL of iQ SYBR Green Supermix was used (Bio-Rad Laboratories, Hercules, Calif.). The qRT-PCR was run using Roche Light-Cycle 480 II with the following parameter settings (Roche Applied Science, Indianapolis, Ind.): 95° C. pre-incubation for 10 mins, amplification was done for 45 cycles at 95° C. for 10 sec and 60° C. for 10 sec; the melting curve was set-up for 95° C., 65° C., 97° C.; cooling was set-up at 40° C. for 30 sec. Each qPCR run was performed with three independent tissue samples, each sample having two technical replicates. Two genes that showed stable expression values in a large set of microarray experiments across treatments and tissue samples were used as internal controls. A description of the genes and primer sequences is provided in Table 4. Crossing point value (Cp or Ct), which was the point at which the fluorescence crosses the threshold, and melting curve analyses were obtained using the LightCycler Roche 480 Software v1.5. The melting curve data was collected for all samples and genes to ensure a single peak, indicating amplification of specific region by a pair of primers.

Example 8—Microarray Data Analysis

Wheat Array GeneChip data was generated using standard Affymetrix protocol (Affymetrix, Santa Clara, Calif.). Two independent biological replicates were used for array experiment. CEL files were analyzed using the limma package in the R software program. Briefly, the bioconductor 'affy' and 'limma' packages was used for reading CEL files and normalizing microarray data (Smyth, 2005, Bioinformatics and Computational Biology Solutions using R and Bioconductor, Springer, New York, 397-420). The raw intensity values for the GeneChip arrays were background corrected, log$_2$-transformed and quantile normalized with robust multi array average (RMA) within the R package 'affy' (Irizarry et al., 2003, Biostatistics, 4:249-264). The statistical computation and assessment of differential expression was done with empirical Bayes function which moderates the standard errors of estimated log-fold changes toward a pooled standard deviation value. The p-values were adjusted to Benjamini and Hochberg's method (BH) to control the false discovery rate. The top table function was used to list the genes according to the specified p-value of 0.05, log 2 fold change of 1, and p-value adjust=BH. Probe set annotated was generated from HarvEST:WheatChip (Close et al., 2007, Methods Mol. Biol., 406:161-77). The raw array data is publically available through NCBI GEO (GSE42214). A complete list of differentially expressed transcripts is listed in Table 5.

TABLE 5

List of Differentially Expressed Genes

| Category | Probeset | Fold Change | Rice Locus | Rice Description | Arabidopsis Accession | Arabidopsis Description |
|---|---|---|---|---|---|---|
| Cell Wall | Ta.10287.1.A1_at | -2.99 | LOC_Os03g18860.1 | pectinesterase | AT4G02330 | pectinesterase |
|  | Ta.10848.1.S1_at | -2.75 | LOC_Os06g51500.1 |  | AT5G49720 | ARABIDOPSIS THALIANA GLYCOSYL HYDROLASE 9A1; cellulase/hydrolase, hydrolyzing O-glycosyl compounds |
|  | TaAffx.86606.1.S1_at | -2.12 | LOC_Os09g25490.1 | CESA9 cellulose synthase | AT5G17420 | IRX3 (IRREGULAR XYLEM 3); cellulose synthase |
|  | TaAffx.69760.1.S1_at | -1.76 | LOC_Os08g01670.1 | pectin methylesterase inhibitor | AT5G64620 | pectinesterase inhibitor |
|  | Ta.79853.1.S1_at | 1.11 | LOC_Os01g32100.1 | protein transposon protein | AT2G15880 | leucine-rich repeat family protein/extension family protein |
|  | TaAffx.56769.1.S1_at | 1.74 | LOC_Os01g18080.1 | retrotransposon protein | AT1G20130 | hydrolase, acting on ester bonds/lipase/structural constituent of cell wall |
|  | Ta.30682.2.S1_at | 2.48 | LOC_Os08g17170.1 | protein retrotransposon protein | AT4G18670 | structural constituent of cell wall |
|  | TaAffx.8948.1.S1_at | 2.71 | LOC_Os07g10770.1 | CESA8-cellulose synthase | AT5G05170 | CEV1 (CONSTITUTIVE EXPRESSION OF VSP 1); cellulose synthase/transferase |
| Signaling | Ta.9675.2.S1_at | 3.12 | LOC_Os01g57630.3 | protein kinase domain containing protein | AT4G13340 | leucine-rich repeat family protein/extension family protein |
|  | Ta.5029.2.A1_at | -6.3 | LOC_Os11g11890.1 |  | AT4G23140 | CRK6 (CYSTEINE-RICH RLK 6); kinase |
|  | TaAffx.36786.1.S1_at | -2.38 | LOC_Os04g12560.1 | receptor-like protein kinase | AT5G60900 | RLK1 (RECEPTOR LIKE PROTEIN KINASE1) |
|  | TaAffx.8197.1.S1_at | -2.34 | LOC_Os01g22590.1 | retrotransposon protein | AT1G26150 | PERK10 (PRONLINE-RICH EXTENSIN LIKE RECEPTOR KINASE 10; ATP binding/protein kinase/protein serine/threonine kinase/protein ty |
|  | Ta.7164.3.S1_x_at | -1.66 | LOC_Os01g23620.1 | aspartokinase | AT1G56330 | ATSAR1B (SECRETION-ASSOCIATED RAS 1 B) |
|  | TaAffx.79885.1.S1_at | -1.57 | LOC_Os07g20544.2 |  | AT5G14760 | CARAB-AK-LYS; aspartate kinase |
|  | TaAffx.79349.1.S1_at | -1.47 | LOC_Os08g09670.1 | F-box/LRR-repeat protein 22 | AT4G05470 | F-box family protein (FBL21) |
|  | TaAffx.61545.1.S1_at | -1.43 | LOC_Os08g44350.1 | histidine containing phosphotransfer protein | AT3G21510 | AHP1 (HISTIDINE CONTAINING PHOSPHOTRANSMITTER 1); histidine phosphotransfer kinase |
|  | TaAffx.108924.1.S1_at | -1.37 | LOC_Os04g01070.1 | protein transposon protein | AT1G26150 | PERK10 (PROLINE-RICH EXTENSIN-LIKE RECEPTOR KINASE 10) |
|  | Ta.10515.1.S1_at | 1.06 | LOC_Os04g44910.1 | receptor like protein kinase | AT2G37710 | RLK (receptor lectin kinase); kinase |
|  | TaAffx.72133.3.S1_x_at | 1.13 | LOC_Os01g47430.2 |  | AT1G29370 | kinase related |
|  | Ta.21202.1.S1_at | 1.18 | LOC_Os06g45660.1 | WD domain, G-beta repeat domain containing protein | AT1G31160 | zinc-binding protein putative/protein kinase C inhibitor protein kinase |
|  | Ta.59697.1S1_at | 1.2 | LOC_Os03g64110.1 | serine/threonine-protein kinase receptor | AT1G70460 | protein kinase |
|  | TaAffx.86549.1.S1_at | 1.21 | LOC_Os06g07300.1 | cDNA UBA and UBX domain-containing protein | AT2G19130 | S-locus lectin protein kinase family protein |
|  | TaAffx.112930.1.S1_at | 1.47 | LOC_Os04g39040.1 |  | AT4G15410 | PUX5 (Arabidopsis thaliana serine/threonine protein phosphatase 2A 55 kDa regulatory subunit B prime gamma) |
|  | TaAffx.81496.1.S1_at | 1.84 | LOC_Or06g45630.1 |  | AT1G71830 | SERK1 (SOMATIC EMBRYOGENESIS RECEPTOR-LIKE KINASE 1) |
|  | Ta.17605.1.S1_at | 1.96 | LOC_Os01g65230.1 | ACG kinases include homologs to PKA, PKG and PKC inactive receptor kinase At1g27190 |  |  |
|  | Ta.22666.1.S1_at | 2.24 | LOC_Os01g66820.1 | atypical receptor-like kinase MARK | AT3G17840 | RLK902; ATP binding/kinase/protein serine/threonine kinase |
|  | Ta.18480.1.S1_x_at | 3 | LOC_Os03g12250.1 | cDNA receptor-like protein kinase 5 precursor, putative expressed | AT5G16590 | LRR1; ATP binding/linase/protein serine/threonine kinase |
|  | TaAffx.83317.1.S1_at | -1.31 | LOC_Os02g40180.1 |  |  |  |
| Transcription Factors | Ta.23792.1.S1_at | -3.92 | LOC_Os06g43860.1 | homeobox protein knotted-1 | AT5G11060 | KNAT4 (KNOTTED1-LIKE HOMEOBOX GENE 4) |
|  | Ta.12700.1.S1_at | -1.68 | LOC_Os05g11414.2 | OsMADS58 | AT4G18960 | AG (AGAMOUS) |
|  | Ta.13267.1.S1_at | -1.05 | LOC_Os06g50310.1 | E2F-related protein | AT4G35040 | bZIP transcription factor family protein |
|  | TaAffx.52152.1.S1_at | 1.06 | LOC_Os02g36880.4 | No apical meristem protein | AT5G61430 | ANAC100 (ARABIDOPSIS NAC DOMAIN CONTAINING PROTEIN 100) |
|  | Ta.3395.2.S1_at | 1.43 | LOC_Os06g06750.1 | MADS-box family gene with MIKCc type-box | AT1G24260 | SEP3 (SEPALLATA3) |
|  | TaAffx.24919.2.S1_at | 1.77 | LOC_Os09g31390.1 |  | AT5G06839 | bZIP family transcription factor |
|  | TaAffx.58172.1.S1_at | 2.05 | LOC_Os01g09800.1 | BTBA1-Bric-a-Bac, Tramtrack, Broad Complex BTB domain with Ankyrin repeat region | AT1G64280 | NPR1(NONEXPRESSER OF PR GENES 1) |
|  | TaAffx.58412.1.S1_at | 1.54 | LOC_Os09g28210.1 | cDNA bHelix-loop-helix transcription factor transcription factor X1, putative, expressed |  |  |
|  | TaAffx.143995.9.S1_at | -1.09 | LOC_Os01g44230.1 | transcription factor X1 | AT3G48670 | XH/XS domain containing protein/XS zinc finger domain containing protein |
|  | TaAffx.128836.1.S1_x_at | -7.79 | LOC_Os01g44230.2 |  | AT4G00380 | XH/XS domain containing protein/XS zinc finger domain containing protein |

TABLE 5-continued

List of Differentially Expressed Genes

| Category | Probeset | Fold Change | Rice Locus | Rice Description | Arabidopsis Accession | Arabidopsis Description |
|---|---|---|---|---|---|---|
| Protein Degradation | TaAffx.93139.1.A1_at | -3.04 | LOC_Os09g35690.1 | cDNA zinc RING finger protein | AT3G63530 | BB (BIG BROTHER); ubiquitin-protein ligase |
| | TaAffx.37159.2.S1_x_at | -2.72 | | | AT5G03240 | UBQ3 (POLYUBIQUITIN 3) |
| | TaAffx.37159.2.S1_at | -2.2 | | | AT5G03240 | UBQ3 (POLYUBIQUITIN 3) |
| | TaAffx.86073.1.S1_at | -1.72 | LOC_Os01g66330.1 | cDNA ATP-dependent Clp protease ATP-binding subunit clpX | | |
| | Ta.5004.2.S1_at | -1.6 | LOC_Os11g14900.5 | thiol protease SEN102 precursor | AT3G48340 | cysteine-type endopeptidase |
| | TaAffx.85253.1.S1_at | -1.51 | LOC_Os02g27360.2 | aspartic proteinase-like protein 2 | AT1G05840 | aspartyl protease family protein |
| | TaAffx.17659.1.S1_x_at | 1.21 | LOC_Os01g60410.2 | cDNA ubiquitin-conjugating enzyme | AT4G27960 | UBC9 (UBIQUITIN CONJUGATING ENZYME 9); ubiquitin-protein ligase |
| | Ta.16236.1.S1_at | -7.98 | LOC_Os06g19800.1 | BURP domain containing protein | AT3G26280 | RD22; nutrient reservoir |
| Other | TaAffx.28894.2.S1_at | -2.72 | LOC_Os02g09400.1 | cytochrome P450 | | CYP71B4; electron carrier/heme binding/iron ion binding/monooxygenase/oxygen binding |
| | Ta.14009.1.A1_at | -2.37 | LOC_Os04g59480.1 | POT family protein | AT1G22540 | proton-dependent oligopeptide transport (POT) family protein |
| | TaAffx.112673.1.S1_at | -2.32 | LOC_Os03g17470.1 | IN2-1 protein | AT3G55040 | GSTL2 |
| | Ta.23822.1.S1_at | -2.21 | LOC_Os08g01510.1 | cytochrome P450 | AT1G13080 | CYP71B2 (CYTOCHROME P450 71B2) electron carrier/heme binding/iron ion binding/monooxygenase/oxygen binding |
| | Ta.5309.3.S1_at | -2.07 | LOC_Os04g39440.3 | | AT4G17170 | RABB1C (ARABIDOPSIS RAB GTPASE HOMOLOG B1C) |
| | Ta.7164.3.S1_at | -2.02 | LOC_Os01g23620.1 | ras-related protein | AT2G56330 | ATSAR1B (SECRETION-ASSOCIATED RAS 1 B) |
| | Ta.17303.1.a_at | -1.92 | LOC_Os12g37419.1 | cytochrome c oxidase polypeptide Vc | AT2G47380 | cytochrome c oxidase subunit Vc family protein/COX5C family protein |
| | TaAffx.120526.2.S1_at | -1.76 | LOC_Os07g31770.1 | chalcone synthase | AT5G13930 | TT4 TRANSPARENT TESTA 4); naringenin-chalcone synthase |
| | TaAffx.8336.1.S1_at | -1.69 | LOC_Os03g10510.1 | outer mitochondrial membrane porin | AT5G67500 | VDAC2 (VOLTAGE DEPENDENT ANION CHANNEL 2) |
| | Ta.23979.1.A1_at | -1.54 | LOC_Os01g73170.1 | peroxidase precursor | AT1G71695 | peroxidase 12 (PER12) |
| | Ta.23663.1.A1_at | -1.29 | LOC_Os01g04360.1 | hsp20/alpha crystallin family protein | AT5G59720 | HSP18.2 (heat shock protein 18.2) |
| | TaAf fx.120375 1.1_at | -1.23 | LOC_Os05g04120.1 | ferroporting domain containing protein | AT5G26820 | ATIREG3 (IRON REGULATED PROTEIN 3) |
| | TaAffx.52969.1.S1_at | -1.22 | LOC_Os04g42100.1 | nodulin, putatively expressed | AT3G19430 | late embryogenesis abundant protein-related nodulin family protein |
| | TaAffx.112558.1.S1_at | -1.22 | LOC_Os08g42010.1 | | AT5G14120 | |
| | Ta.13250.3.S1_at | 1.31 | LOC_Os06g09688.1 | chaperonin, putative | AT5G20720 | CPN20 (CHAPERONIN 20) |
| | TaAffx.86941.1.S1_at | 1.37 | LOC_Os10g07534.1 | disease resistance protein RPM1 | AT1G59780 | disease resistance protein (CC-NBS-LRR class) |
| | Ta.15986.1.S1_at | 1.52 | LOC_Os05g04700.1 | OsRCl2-6 | AT3G05880 | RCI2A (RARE COLD INDUCIBLE 2A) |

TABLE 5-continued

List of Differentially Expressed Genes

| Category | Probeset | Fold Change | Rice Locus | Rice Description | Arabidopsis Accession | Arabidopsis Description |
|---|---|---|---|---|---|---|
| | Ta.Affx.86014.1.S1_at | 1.7 | LOC_Os05g48020.1 | SNARE domain containing protein | AT3G09740 | SYP71 (SYNTAXIN OF PLANTS 71) |
| | Ta.2395715.1.S1_at | 1.76 | LOC_Os08g41880.1 | nucleotide pyrophosphatase/phosphodiesterase | AT5G50400 | PAP27 (PURPLE ACID PHOSPHATASE 27) |
| | Ta.Affx.57715.1.S1_at | 1.9 | LOC_Os12g42230.1 | transketolase | AT2G34590 | transketolase family protein |
| | Ta.20911.2.A1_at | 1.92 | LOC_Os03g17174.1 | Psbp | AT2G39470 | PPL2 (PsbP-like protein 2) |
| | Ta.14590.3.S1_at | 1.96 | LOC_Os06g11800.1 | annexin | AT5G10230 | ANNAT7 (ANNEXIN ARABIDOPSIS 7) |
| | Ta.Affx.57167.1.S1_at | 2.03 | LOC_Os01g43390.1 | uroporphyrinogen decarboxylase | AT3G14930 | HEME1 |
| | Ta.15865.1.A1_at | 2.31 | LOC_Os03g12260.1 | cytochrome P450 protein | AT3G56630 | CYP94D2; electron carrier/heme binding/iron ion binding/monooxygenase/oxygen binding |
| | Ta.17367.1.S1_at | 2.31 | LOC_Os05g13390.1 | | AT1G66240 | ATX1 (ARABIDOPSIS HOMOLOG OF ANTI-OXIDANT 1) |
| | Ta.4978.2.A1_a_at | 2.32 | | | AT4G11430 | hydroxyproline-rich glycoprotein family protein |
| | Ta.Affx.85805.1.S1_s_at | 2.36 | LOC_Os05g06500.1 | universal stress protein domain containing protein | AT3G17020 | universal stress protein (USP) family protein |
| | Ta.Affx.98251.1.S1_at | 2.55 | LOC_Os03g37120.1 | | AT4G19430 | late embryogenesis abundant protein-related/LEA protein-related |
| | Ta.27016.1.A1_x_at | 2.7 | LOC_Os01g27230.1 | 12-oxophytodienoate reductase | AT1G76690 | OPR2 |
| Hormone | Ta.3576.1.S1_at | -1.33 | LOC_Os06g51330.2 | | AT4G09610 | GASA2 (GAST1 PROTEIN HOMOLOG 2) |
| | Ta.Affx.113441.1.S1_at | -2.89 | LOC_Os12g43130.1 | phytoene synthase, chloroplast precursor | AT5G17230 | phytoene synthase (PSY) |
| | Ta.23392.2.S1_x_at | 1.05 | LOC_Os03g09900.1 | | AT5G35735 | auxin-responsive family protein |
| Metabolism | Ta.6293.1.A1_at | -5.18 | LOC_Os08g29650.1 | | AT4G35785 | nucleic acid binding/nucleotide binding |
| | Ta.22589.1.S1_at | -2.34 | LOC_Os02g51930.1 | cytokinin-O-glucosyltransferase 2 | AT1G78270 | AtUGT85A4 (UDP-glucosyl transferase 85A4) |
| | Ta.Affx.824901.S1_at | -2.31 | LOC_Os01g48960.1 | glutamate synthase, chloroplast precursor | AT5G53460 | GLT1; glutamate synthase (NADH) |
| | Ta.Affx.53860.1.S1_at | -1.85 | LOC_Os03g52840.1 | serine hydroxymethyltransferase mitochondrial precursor | AT4G37930 | SHM1 (SERINE TRANSHYDROXYMETHYL TRANSFERASE 1) |
| | Ta.1291.1.A1_x_at | -1.65 | LOC_Os01g71670.1 | glycosyl hydrolases family 17 | AT3G57270 | BG1 (BETA-1,3-GLUCANASE 1) |
| | Ta.Affx.87056.1.S1_at | -1.63 | LOC_Os06g14810.1 | 3-ketoacyl-CoA synthase | AT1G25450 | KCS5 (3-KETOACYL-COA SYNTASE 5); fatty acid elongase |
| | Ta.Affx.55916.2.S1_at | -1.34 | LOC_Os04g46930.2 | protein serine racemase | AT4G11640 | AtSR (ARABIDOPSIS THALIANA SERINE RACEMASE) |
| | Ta.5829.1.S1_at | -1.16 | LOC_Os11g42510.1 | tyrosine aminotransferase | AT2G20610 | SUR1 (SUPERROOT 1); S-alkylthiohydroximate lyase |
| | Ta.Affx.65466.1.S1_at | 1.13 | LOC_Os02g49920.1 | 3-ketoacyl CoA synthase | AT1G25450 | KCS5 (3-KETOACYL-COA SYNTASE 5); fatty acid elongase |
| | Ta.30535.1.S1_at | 1.45 | LOC_Os03g11050.3 | mannose-1-phosphate guanyltransferase | AT3G74910 | ADP-glucose pyrophosphorylase family protein |
| | Ta.Affx.57742.1.S1_at | 1.66 | LOC_Os06g09450.8 | sucose synthase | AT3G43190 | SUS4; UDP-glycosyltransferase/sucrose synthase |
| | Ta.56059.1.S1_at | 2.25 | LOC_Os02g47090.1 | peptide transporter PTR2 | AT1G32450 | NRT1.5 (NITRATE TRANSPORTER 1.5) |

Example 9—Construction of the Co-Expression Network

The co-expression network was constructed with RiceNet using rice orthologous information from HarvEST:Wheat for differentially expressed transcripts between P76 and TL under limited-water conditions (Lee et al., 2011, PNAS USA, 108:1-6). Genes corresponding to ribosomal proteins were removed to reduce the occurrence of false relationships between otherwise non-connected genes. Primers for the genes identified from the network analysis and validated with quantitative PCR are listed in Table 4 and their expression is summarized in Table 6.

TABLE 4

Genes and Primer Sequences (A)

| Probeset ID | Arabidopsis Gene Annotation | Left Primer (5' to 3') | Right Primer (5' to 3') | Product Size (bp) | SEQ ID NO |
|---|---|---|---|---|---|
| TaAffx.81496.1.S1_at | SERK1 | CCTCCTGAGATTGGCACATT | GCATTGTGCCACTGAACTTG | 163 | 12, 13 |
| Ta.23792.1.S1_at | KNAT3 | CCTTCAAGGAACAGCTCCAG | CTCTCACTGTCGACCGGATT | 166 | 14, 15 |
| Ta.13267.1.S1_at | E2f | GTCATGAGTGGCCAGGTTTT | GCCAATAGTCTCTCGCAAGG | 157 | 16, 17 |
| TaAffx.8948.1.S1_at | CESA3 | TTGTGCTGCGATTGATTGTT | TAAGTCTCCCGGTTGATTGG | 169 | 18, 19 |
| Ta.6862.2.S1_at | BRI-1 | TGTTCAAGCCTCAACAGACG | TTGCCAACAAGAAACAACCA | 229 | 20, 21 |
| Ta.9047.2.S1_a_at | GH9B7 | GGTGGAATTCTCTGCAGCAT | AGCTTCATTGGGTTGTCACC | 155 | 22, 23 |
| Ta.856.1.S1_at | ERL1 | GCATTCATGGTGTGGATCAG | ATGGGGTTCGATCAATTCAA | 186 | 24, 25 |
| Ta.4385.1.S1_at | CTL1 | ACCAGACCATCACCGACTTC | GCCGTATCCACATGAGGTCT | 230 | 26, 27 |
| Ta.1804.1.S1_s_at | COB1 | CAAGCTCTCATGTCGTGGAA | ACACAGCTTCCTGGACGAGT | 167 | 28, 29 |
| TaAffx_8566_1_S1_at | PP2C | TGCTAGCAGGAGGTTGGATT | TCCCTGTTTCTTGGTCCTTG | 150 | 30, 31 |
| TaAffx_79349_1_S1_at | FBL21 | CACTGCTAATTCGCTCACCA | CAGCATGGTCTCGGAATTTT | 210 | 32, 33 |
| Ta_18480_1_S1_x_at | RLK902 | CAGAAGGCCGACGTCTACAG | ACCATCTCCTCCTCCACGTT | 195 | 34, 35 |
| Internal Control 4 | — | CCCTGGTTTGAGCAAGTCAT | AGTCGTGACTGAAGGGGTTG | 160 | 36, 37 |
| Internal Control 8 | — | TGAGGTTGTCAAGCAACAGG | CATAAGACCAGCCCAAGCAT | 152 | 38, 39 |

(B)

| Probeset ID | Arabidopsis Gene Annotation | Left Primer (5' to 3') | Right Primer (5' to 3') | Product Size (bp) | SEQ ID NO |
|---|---|---|---|---|---|
| Ta.23792.1.S1_at | KNAT3 | CGTCTACCCTGAAAGCTTGG | CCTCACCTGCATTGTTCCTT | 207 | 40, 41 |
| TaAffx.81496.1.S1_at | SERK1 | GACGGCTTCACCGTCATATT | AGCAGCTACGGCATCAGAAT | 223 | 42, 43 |
| Ta.9675.2.S1_at | LRX | AATCGTACAACCACCCAAGC | ATTGTAGCACTTGGCGTCAG | 238 | 44, 45 |
| Ta.14590.3.S1_at | Annxn | GTCAACACAAGGTTGGCTCA | AGCCTTGAGATCCTTGGTGA | 170 | 46, 47 |

(C)

| Probeset ID | Name used in Manuscript | Left Primer (5' to 3') | Right Primer (5' to 3') | Product Size (bp) | SEQ ID NO |
|---|---|---|---|---|---|
| Ta.28144.1.S1_at | Ta.28144 | AGTATCTGCATCCACCTCGAC | CTGGCATCCACCTTCTTCTT | 153 | 48, 49 |
| Ta.7772.1.S1_at | Ta.7772 | CGTTAATGAGACCGCTTTCC | GATCAGCAATCCAGCATTCA | 199 | 50, 51 |
| Ta.16810.1.S1_at | Ta.16810 | CAGATGGTTCGTTCGGTGAT | AGCAGAGAGCAACGGAAAAC | 261 | 52, 53 |

TABLE 6 pRT-PCR Analysis of Network Associated Genes

|  | Rice Locus | Wheat Probe | Relative Expression | Standard Error |
|---|---|---|---|---|
| SERK1 | LOC_Os06g45630.1 | TaAffx.81496.1.S1_at | 1.5 | 0.2 |
| FBL21 | LOC_Os08g09670 | TaAffx.79349.1.S1_at | 0.2 | 0.05 |
| LRR1 | LOC_Os02g40180 | TaAffx.83317.1.S1_at | 3.2 | 1.09 |
| PP2C | LOC_Os07g32380 | TaAffx.8566.1.S1_at | N/A | N/A |
| BRI1 | LOC_Os02g09359 | Ta.6862.2.S1_at | 2.2 | 0.20 |
| CESA3 | LOC_Os07g10770 | TaAffx.8948.1.S1_at | 6.1 | 3.19 |
| COB | LOC_Os05g32110 | Ta.1804.1.S1_s_at | 11.0 | 4.60 |
| CTL1 | LOC_Os09g32080 | Ta.4385.1.S1_at | 2.2 | 0.63 |
| ERL | LOC_Os06g03970 | Ta.856.1.S1_at | N/A | N/A |
| GH9B7 | LOC_Os09g36350 | Ta.9047.2.S1_a_at | 6.0 | 1.57 |

CELLULOSE SYNTHASE (CESA3),
CHITINASE-LIKE1 (CTL1),
COBRA1 (COB1),
RECEPTOR-LIKE KINASE902 (RLK902),
GLYCOSYL HYDROLASE 9B7 (GH9B7),
BRASSINOSTEROID INSENSITIVE1 (BRI1),
PROTEIN PHOSPHATASE 2C (PP2C),
ERECTA-LIKE1 (ERL1),
SOMATIC EMBRYOGENESIS RECEPTOR KINASE1 (SERK1),
F-BOX21 (FBL21), and
LEUCINE-RICH REPEAT (LRR1)

Example 10—SFP Identification and In Silico Mapping of Candidate Genes

Microarray data were preprocessed as described above. To eliminate probe sets with absent transcripts, we adopted the procedure suggested by Schuster et al. (2007, Genome Biol., 8:R125) making "present" and "absent" calls for each probe set. A probe set was retained and used for SFP detection if it had present calls in all biological replicates of the two genotypes under comparison. We used robustified projection pursuit (RPP) method for SFP detection (Cui et al., 2005, Bioinformatics, 21:3852-8) through pair-wise comparison among parent genotype P76, TL and NC for all samples. For each comparison, we used an arbitrary cutoff value of 10 for calling SFP-containing probe sets, within which a probe will be identified as a SFP probe if it accounts for more than 40% of overall outlying score of its residing probe set.

Primers were designed so that the region flanking each probe were amplified. Sequences were amplified from cDNA using the primers listed in Table 4 using PCR. A 25 µL reaction was prepared using GoTAQ green master mix (Promega) consisting of 1 µL each of forward and reverse primer at 10 µM and 2 µL of cDNA. Sequences were amplified using the following program: denaturation at 94° C. for 3 min followed by 30 cycles of amplification (30 sec at 94° C., 30 sec at 58° C., 30 sec at 72° C.) and a final temperature of 72° C. for 7 min. Prior to cloning each reaction was purified using GeneJET™ PCR Purification Kit (Thermo Scientific). Amplicons were cloned into PGEM T Easy Vector (Promega) and JM109 competent cells were transformed and cultured according to the manufacturer's protocol. Cultures were plated on LB plates supplemented with 100 µg ampicillin and X-Gal-IPTG. Plasmids were retrieved using GeneJET Plasmid Miniprep Kit (Thermo Scientific) and sequenced.

Example 11—PCR-Based Mapping of Genes to Wheat Chromosome 7D

A subset of microarray genes that were mapped through the SFP analysis to 7DL using rice-wheat synteny maps were confirmed using a series of nullisomic-tetrasomic and ditelosomic Chinese Spring wheat lines (Devos et al., 1999, Cereal Res. Commun., 27:231-9; Sorrells et al., 2003, Genome Res., 13:1818-27). Primers specific to 7DL were designed using probe set sequences obtained from HarvEST WheatChip version 1.59, Grain Genes (wheat.pw.usda.gov/ on the World Wide Web) and NCBI BLAST (Altschul et al., 1997, Nucl. Acids Res., 25:3389-402; Close et al., 2007, Methods Mol. Biol., 406:161-77). The selected 7D sequences were used to design primers using Primer3 software (Rozen, 2000, Methods Mol. Biol., 132:365-86). PCR was performed to map the genes using genomic DNA from Chinese spring, nullisomic-tetrasomic and ditelosomic 7DL and 7DS Chinese Spring wheat plants. PCR was performed using the following settings: 95° C. pre-incubation for 3 mins., amplification was done for 40 cycles at 95° C. for 30 sec and 58° C. for 30 sec and 72° C. for 1 min, and extension at 72° C. for 3 mins. The PCR products were run on a 2% agarose gel molecular biology grade (Benchmark Scientific, Edison, N.J.) and imaged using BioDoc-IT Imaging system UV Transillumator (UVP, LLC, Upland, Calif.).

Example 12—*Agropyron* Translocation Introduces an Adaptive Root Response in Wheat It was hypothesized that the differences in biomass and yield between the *Agropyron* 7DL lines and the corresponding parental genotypes could be due to increased investment in root production, thus increasing acquisition of water and nutrients from the soil. We used a parent line, Pavon76 (P76), the 1-96-1 translocation line (TL), and a negative control (NC) for the translocation event for these experiments (FIG. 1). The total number of lateral roots (>1 mm) on the primary root axis were counted, and lateral root density was calculated by dividing the number of lateral roots on the primary root axis by the primary root length. Statistical significance was determined using a one-way ANOVA using Tukeys method.

TL exhibited longer primary roots at 4 days and 6 days when compared to the control genotypes (P76 and NC) ($p<0.05$, Table 1, Table 4). Seminal roots of TL were longer at 2, 4 and 6 days when compared to P76 and NC ($p<0.01$, Table 1). TL line produced significantly more lateral roots on the primary root axis at 4 and 6 days. A significant increase in lateral root density was also observed in TL at 4 and 6 days ($p<0.05$). During the preliminary experiments to optimize the cigar roll method, it was observed that the increased root number in TL was inducible only under a mild water stress. No significant differences were observed under adequate access to water. Collectively, these observations suggested that presence of 7DL.7EL segment in the Pavon background could be conferring an adaptive root response under water limitation in the translocation line. The early seedling root phenotyping prompted investigation of the differences in root architecture in older plants.

TABLE 1

Phenotypic evaluation of early seedling root system

|  | 2 days | 4 days | 6 days |
|---|---|---|---|
|  | Lateral Root Number (primary root axis) | | |
| P76 | nd | 1.3 ± 0.6 | 8.8 ± 1.9 |
| TL | nd | 5.1 ± 0.8 | 27.6 ± 2.3 |
| NC | nd | 1.2 ± 0.6 | 8.8 ± 1.1 |

TABLE 1-continued

Phenotypic evaluation of early seedling root system

|  | 2 days | 4 days | 6 days |
|---|---|---|---|
| Primary Root Length (mm) | | | |
| P76 | 7.2 ± 0.2 | 14.1 ± 1.0** | 18.7 ± 1.9*** |
| TL | 7.2 ± 0.7 | 18.2 ± 0.9 | 27.5 0.6 |
| NC | 7.4 ± 0.3 | 14.4 ± 0.4* | 19.5 ± 0.6*** |
| Lateral Root Density (mm−1) | | | |
| P76 | nd | 0.09 ± 0.03* | 9.47 ± 0.08*** |
| TL | nd | 0.28 ± 0.05 | 1.00 ± 0.08 |
| NC | nd | 0.08 ± 0.04* | 0.44 ± 0.05*** |

***= $p \leq 0.001$,
**= $p \leq 0.005$ and
*= $p \leq 0.05$.
The ± represent standard error.
nd = not detected.
This method was repeated three times using 30 wheat seedlings per cultivar per experiment.

Example 13—TL Lines have Higher Shoot and Root Biomass Under Limited Water Condition To observe the effect of the 1-96-1 translocation on root and shoot phenotypes at pre-tillering stage, we sampled plants at 18 days after germination. The lengths were measured at the time of harvest while the shoot and root dry mass were weighed separately after five days incubation on 60° C. chamber. Statistical significance was determined using a one-way ANOVA using Tukeys method.

Figure 2:
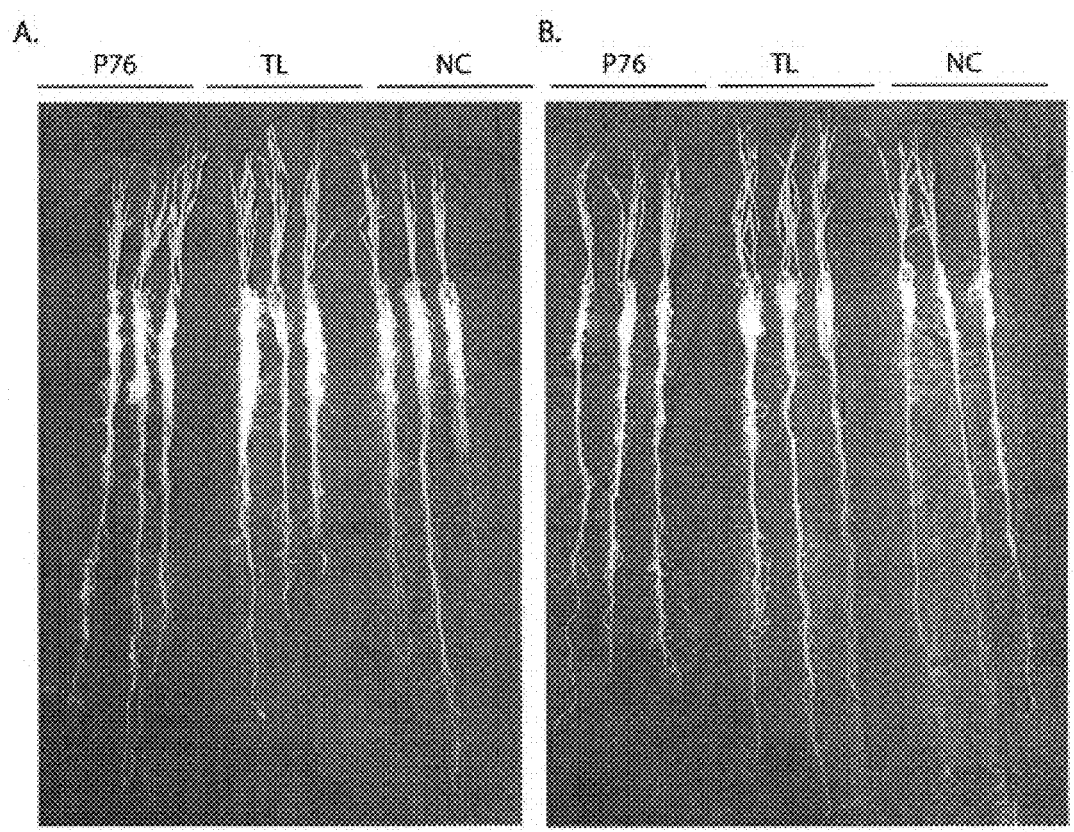
FIG. 2 are photographs of harvested spring wheat cultivar P76 genotypes grown in greenhouse under (A) well-watered and (B) limited-water environments. The images shown are of 18 day old P76 genotypes grown in tubes containing fine sand. The genotypes are labeled as Pavon 76 ("P76"), Pavon 76 with 1-96-1 translocation ("TL") and TL sister line lacking the 1-96-1 translocation ("NC").

Under water stress, TL had higher root ($p \leq 0.01$) and shoot ($p \leq 0.001$) biomass compared to P76 and NC (FIG. 2, Table 2). Moreover, under limited-water conditions, the shoot and root lengths of TL were greater than those of P76 and NC. Under well-watered conditions, there were no differences in root and shoot lengths and dry weights among genotypes. The phenotypic measurements indicate that the 1-96-1 translocation alters root traits under water-limiting conditions.

TABLE 2

Summary of shoot and root lengths and biomasses of spring wheat

| | Shoot | | Root | |
|---|---|---|---|---|
| Genotype | Well-watered | Limited-water | Well-watered | Limited-watered |
| Dry Weight (mg) | | | | |
| P76 | 366.6 ± 57.8 | 209.5 ± 30.0 | 343.6 ± 56.1 | 192.2 ± 18.2 |
| TL | 327.0 ± 51.5 | 336.4 ± 53.1** | 335.7 ± 81.0 | 290.2 ± 44.4*** |
| NC | 320.9 ± 16.9 | 219.5 ± 30.5 | 318.9 ± 54.1 | 206.7 ± 39.4 |
| Length (cm) | | | | |
| P76 | 35.2 ± 13.1 | 24.8 ± 2.0 | 76.2 ± 6.8 | 71.1 ± 3.8 |
| TL | 26.1 ± 2.3 | 27.5 ± 2.8 | 75.6 ± 4.0 | 79.6 ± 7.0* |
| NC | 27.6 ± 3.0 | 26.3 ± 1.9 | 79.8 ± 10.6 | 78.4 ± 2.9 |

***= $p \leq 0.001$ and
*= $p \leq 0.01$.
The ± represent standard error.
This method was repeated three times using 35 wheat plants per cultivar per experiment.

Figure 3:
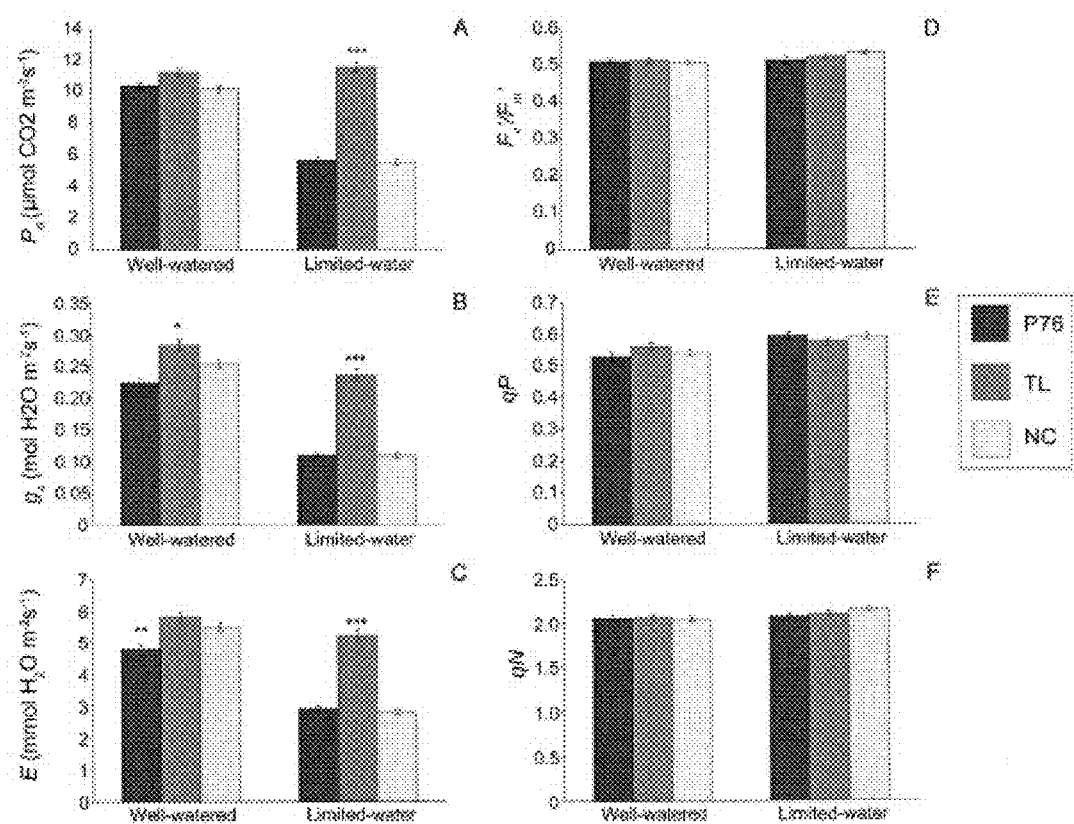
FIG. 3 are graphs showing the results of physiological analyses to assess the response by each genotype under well-watered and limited-water conditions. Panel A shows the photosynthetic rate (Pn), Panel B shows the stomatal conductance ($g_s$) and Panel C shows the transpiration rate (E) measurements obtained for the 18 d old post-transplanted spring wheat plants using the LI-COR 6400. Panel D shows the maximum quantum efficiency of PSII (Fv'/Fm'); Panel E shows photochemical quenching (qP); and Panel F shows non-photochemical quenching (qN). Experiments were performed three times independently. At least nine individual leaves for each genotype in each experiment were measured. Error bars represent standard error. Statistical significance was determined using a one-way ANOVA using Tukeys method. Bars with *** are statistically different at $p \leq 0.001$. As above, the genotypes are labeled Pavon 76 ("P76"), Pavon 76 with 1-96-1 translocation ("TL") and TL sister line lacking the 1-96-1 translocation ("NC").

Example 14—Stomatal Factors Limit Photosynthesis in P76 and NC During Water Deficit To elucidate the physiological impact of higher root biomass in TL during water stress, the $CO_2$ assimilation and gas exchange rates were measured for the three genotypes. Carbon assimilation was different among the three genotypes under limited-water conditions (FIG. 3). Photosynthetic rates were reduced by 45% and 46% in P76 and NC ($p<0.001$), respectively, but did not change significantly in TL (FIG. 3A, 3B, 3C). Water deficit also severely impacted stomatal conductance and transpiration, reducing stomatal conductance ($g_s$) by 50% and 56% and transpiration rate (E) by 39% and 49% compared to well-watered conditions in P76 and NC, respectively. Stomatal conductance was also reduced ($p=0.001$) in TL, but only by 16%. No reductions in transpiration were observed for TL during water deficit. Clearly, TL showed lower sensitivity to water limitation compared to P76 and NC.

Reductions in gas exchange and carbon assimilation are common in drought stressed plants due to decrease in stomatal aperture. However other aspects of photosynthesis such as light utilization and photosynthetic electron transport can also be impacted by drought stress. Therefore, we also measured chlorophyll fluorescence at the pre-tillering stage. Calculation of maximum quantum efficiency of open PSII reaction centers (Fv'/Fm') and the amount of energy used to drive photosynthesis (photochemical quenching; qP) or dissipated as heat (non-photochemical quenching; qN) from fluorescence data is described herein. In well-watered conditions, no differences in Fv'/Fm', qP or qN were observed among the genotypes (FIG. 3D, 3E, 3F). Photochemical quenching (qP) increased under limited-water by 12% and 9% in P76 and NC, respectively, but not in TL.

Figure 4:
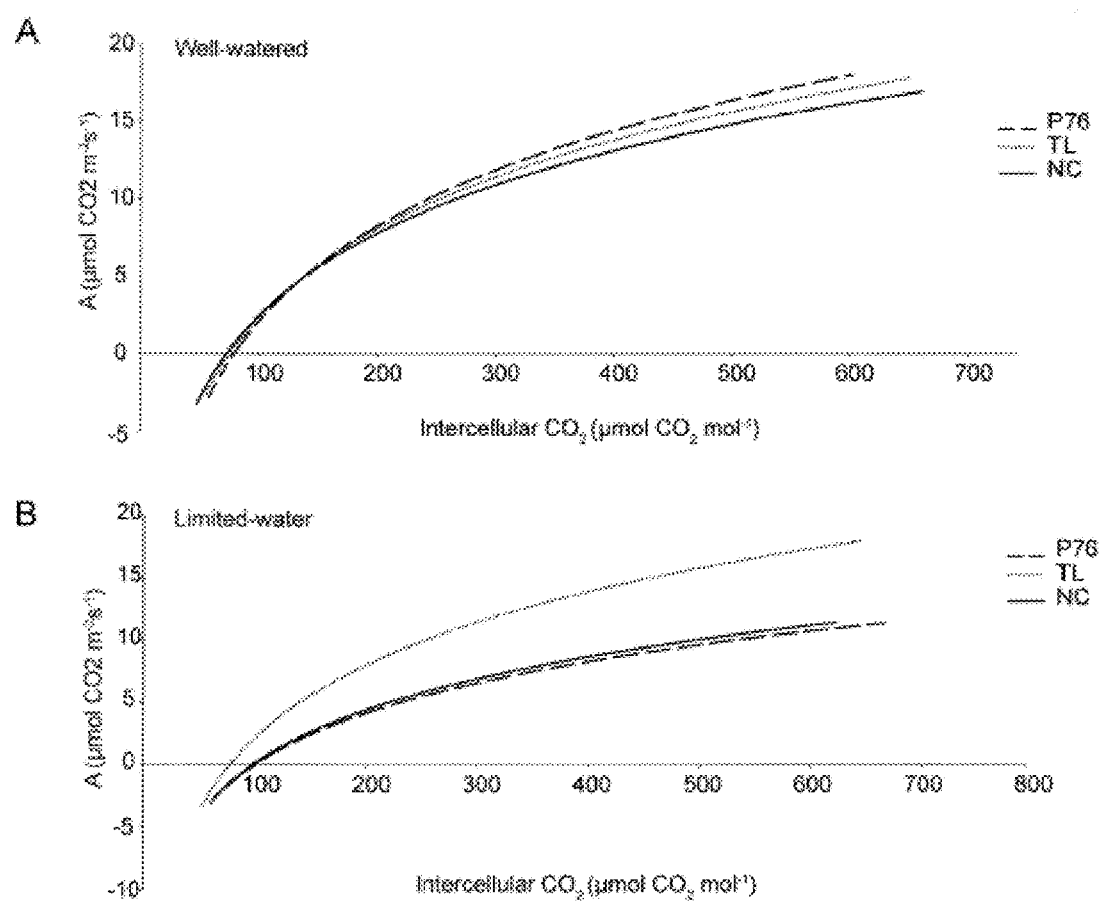
FIG. 4 are graphs showing A/Ci curve analysis of the Pavon 76 (P76), Pavon 76 with 1-96-1 translocation (TL) and TL sister line lacking the 1-96-1 translocation (NC) under well-watered (Panel A) and limited-water environment (Panel B). The $CO_2$ assimilation rates, A ($\mu mol\ m^{-2}\ s^{-1}$), were measured at light saturation (PAR=1000 $\mu mol\ m^{-2}\ s^{-1}$) and were recorded at different chamber $CO_2$ concentration. Experiments were performed three times independently. Six leaf samples per genotype per experiment were used for measurements.

In addition to stomatal aperture and photosynthetic electron transport, biochemical components of carbon assimilation such as the carboxylation of ribulose-1,5-bisphosphate (RuBP) or the rate at which RuBP is regenerated, contribute to the photosynthetic capacity of a plant. To assess whether biochemical factors were contributing to the decline in $CO_2$ assimilation (Pn) in P76, NC, and TL during water deficits, photosynthesis was measured at a series of $CO_2$ concentrations and plotted against intercellular $CO_2$ and the maximum rate of carboxylation by Rubisco (Vcmax) and the rate of electron transport (Jmax) were calculated according to the methods outlined by Dubois et al. (2007, New Phytologist, 176:402-14). Under limited water conditions, Jmax declined significantly by 31% and 24% in P76 and NC respectively (FIG. 4, Table 3), but did not change in TL. Vcmax was reduced by 31% in P76; however, it increased in TL by 18%. Although a 7% reduction in Vcmax was observed in NC, the difference was not significant. The results suggest that the major cause of photosynthetic decline in P76 and NC during water stress could be RuBp regeneration rate.

significantly repressed (p<0.05) in TL compared to P76 and NC at 4 d and 6 d (FIG. 5B).

TABLE 3

Carboxylation rate of Rubisco and RuBP regeneration rate

| | Well-watered | | | Limited-water | | |
|---|---|---|---|---|---|---|
| | P76 | Tl | NC | P76 | TL | NC |
| Vcmax | 69.6 ± 3.8 | 63.1 ± 2.6 | 64.4 ± 4.1 | 50.1 ± 2.1* | 74.9 ± 2.7 | 59.8 ± 4.7 |
| Jmax | 93.9 ± 4.7 | 90.6 ± 4.1 | 83.2 ± 3.9 | 64.3 ± 2.3* | 90.8 ± 2.2 | 63.0 ± 2.5* |
| Ri | 0.86 | 0.90 | 0.86 | 0.92 | 0.95 | 0.92 |

*denotes statistically differences.

Figure 5:
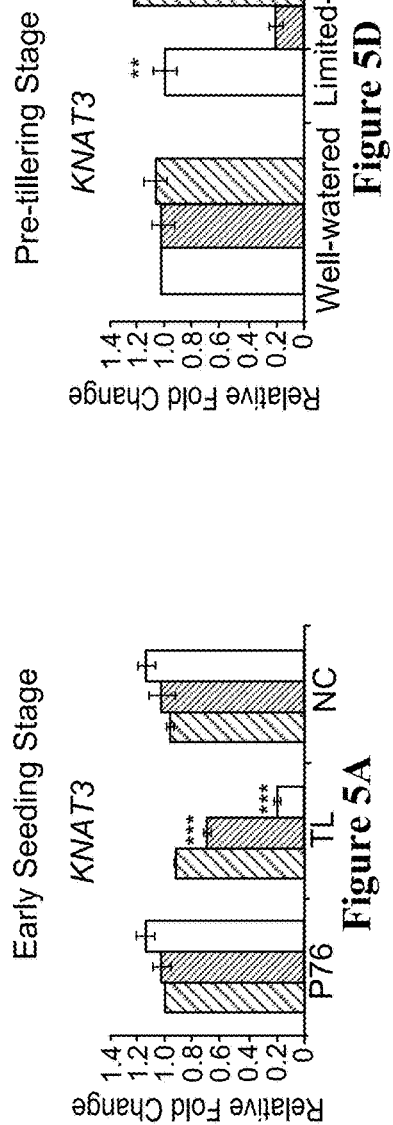
FIG. 5 are graphs showing gene expression analysis of root-related genes by qRT-PCR method. Panels A-C show the expression of microarray genes in early seedling stages using root tissues collected at 2 d, 4 d and 6 d. The genotypes are labeled Pavon 76 (P76), Pavon 76 with 1-96-1 translocation (TL) and TL sister line lacking the 1-96-1 translocation (NC). P76 at 2 d was used as a reference for comparison for each gene expression. Panels D-E show the validation of micro array gene expression using cDNA from 18 d root tissues of P76, TL and NC. The P76 well-watered value was used as a baseline for comparison for gene expression analysis. The representative genes are the following: KNAT3=Knotted-like homeobox gene 3 (in *Arabidopsis*; also known as LRD7=Lateral Root Density 7 (in wheat); E2f=E2F-like transcription factor; SERKl=Somatic embryogenesis receptor-like kinase 1. The error bars represent standard error. The experiment was performed using three biological replicates with two technical replicates per sample. Statistical significance was determined using a one-way ANOVA using Tukeys method. Bars with * are statistically different at $p \leq 0.001$, while those with  indicate a statistical difference at $p \leq 0.01$ and *=$p \leq 0.05$.

Example 15—TL Line Differentially Regulates Genes Associated with Root Architecture To elucidate the molecular mechanism underlying the increased root biomass phenotype observed in the TL line during water stress, we analyzed the root transcriptome of the three genotypes at pre-tillering stage (18 d) under well-watered and water-stressed conditions. A list of differentially expressed genes from various comparisons is provided as Table 5. Several genes known to play a role in root development were differentially expressed between the TL and P76/NC lines in limited water samples. One of these genes is a wheat ortholog of KNOTTED-like homeobox gene 3 in *Arabidopsis* (KNAT3). The wheat ortholog of KNAT3 was down-regulated in TL line compared to P76 and NC under limited water conditions (FIG. 5). In *Arabidopsis*, KNAT3 has been proposed to act as a negative regulator of lateral root development (Truernit et al., 2006, Plant Mol. Biol., 60:1-20; Truernit and Haseloff, 2007, Plant Signaling Behav., 2:10-2). In wheat, the differences in the expression level of the wheat KNAT3 ortholog among the genotypes was notable in the context of increased lateral root formation in TL under water stress. Transcript abundance in early seedlings was lower (p≤0.05) at 4 d in TL compared to P76 and NC (FIG. 5A). At 6 d after germination, the wheat KNAT3 ortholog was down-regulated by 5-fold in TL compared to Pavon at 2 d, while expression was slightly up-regulated in both P76 and NC when compared to P76 at 2 d. No genotypic differences were observed at 2 days after germination.

A wheat E2F-related transcription factor is down-regulated by −1.0 fold in TL under water limited conditions compared to P76 (FIG. 5). The E2F expression is lower in TL by 2.5-fold compared to the NC line. E2F proteins are a family of transcription factors that regulate cell cycle progression in plants and animals. In *Arabidopsis*, E2Fc is known to play an antagonistic role in cell division and is a negative regulator of lateral root formation (del Pozo et al., 2002, Plant Cell, 14:3057-71; Ramirez-Parra et al., 2004, Plant Cell, 16:2350-63). We validated the expression of E2F using qPCR in pre-tillering stage and early seedling stage plants (FIG. 5B, 5D). E2F expression was reduced under water stress in the three genotypes during pre-tillering stage. However, transcript abundance of E2F in TL was repressed by 1.2-fold, compared to less than 1-fold decrease in P76 and NC when compared to corresponding well-watered plants. The expression patterns of E2F in seedling roots was Example 16—Expression of E2F in Seedling Roots Did not Change Significantly in the P76 and NC Under Water Stress Expression of Somatic Embryogensis Receptor Kinase1 (SERKI), a member of the leucine-rich repeat, receptor-like kinase (LRR-RLK) family, was notable among the differentially expressed genes among the genotypes during water stress. Wheat ortholog of SERKI in *Arabidopsis* was up-regulated by 1.8-fold in TL under water-limitation compared to P76 in the array experiment (FIG. 5C, 5E). Expression of SERKI in TL was 3-fold higher than NC under water stress. SERKI plays a critical role in root differentiation in response to auxin in addition to being involved in somatic embryogenesis and gamete (Walker, 1994, Plant Mol. Biol., 26:1599-609; Schmidt et al., 1997, Dev., 124:2049-62; Somleva et al., 2000, Plant Cell Rep., 19:718-26; Hecht et al., 2001, Plant Physiol., 127:803-16). Higher expression of SERKI in TL relative to the P76 and NC was validated by qPCR in roots of pre-tillering plants. SERK I expression was significantly induced in 4 d and 6 d TL seedling roots but not in P76 and NC (FIG. 5C). In summary, our transcriptome analysis identified several differentially regulated genes that could directly or indirectly be associated with the 1-96-1 translocation. We have focused on a relatively small subset of genes for further characterization based on their role growth and development in model species.

Example 17—Role of Brassinosteroids in Shaping Root System Architecture Emerges from Gene Network Analysis To further extract root-associated genetic components involved in the water stress response from our list of differentially expressed microarray genes, we used the wheat-rice orthologous relationships to generate gene regulatory networks using a computational approach. Gene networks were constructed using the recently developed tool RiceNet to determine putative relationships among genes and predict root trait associated genes (Lee et al., 2011, PNAS USA, 108:1-6). This approach is likely to uncover some genes that are expected to be missed in transcriptome analysis due to low expression levels or lack of representation on the wheat array. RiceNet combines functional genomics, proteomics and comparative genome-scale datasets from diverse organisms to predict functional relationships among genes using a Bayesian log likelihood scoring (LLS) method (Lee et al., 2011, PNAS USA, 108:1-6). Comparisons of root transcriptome of P76 and TL under limited water conditions resulted in the identification of the 384 differentially expressed wheat transcripts. Of these, 224 were assigned to corresponding rice loci. After removal of duplicate loci, a list of 202 genes was queried in RiceNet, resulting in the construction of nine networks from 58 connected genes. Fifty genes were not found in RiceNet, while an additional 94 genes remained unlinked to other genes in the input set. We selected candidate genes with a LSS score >2.0 with particular focus on genes associated with regulation of cell division, growth and root development.

Figure 6:
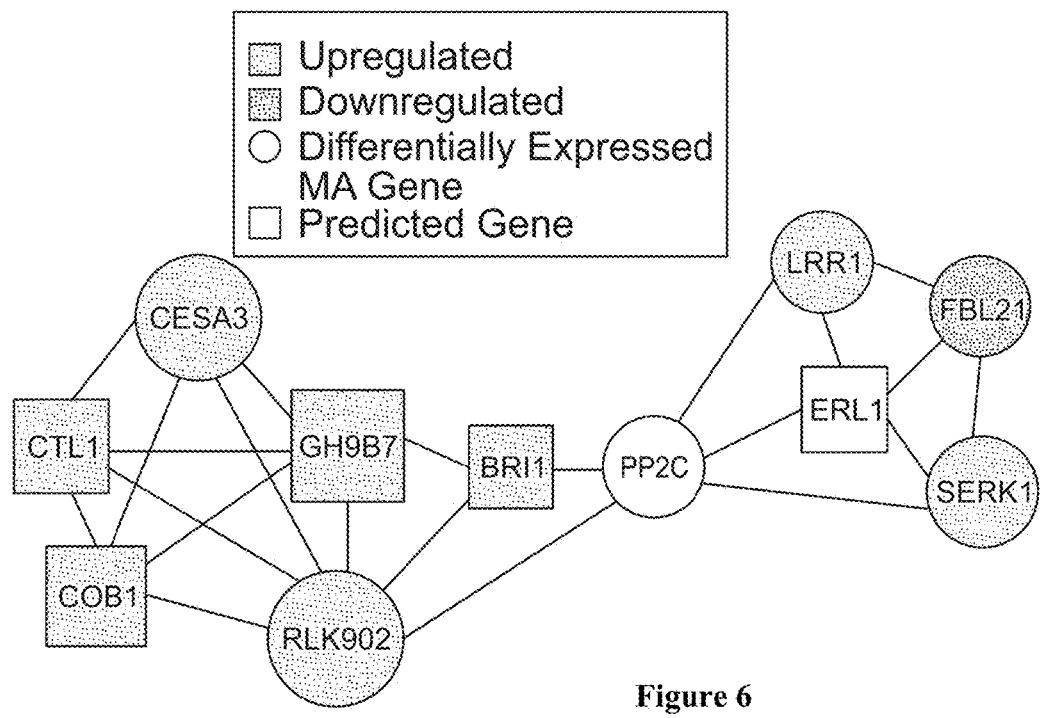
FIG. 6 is a schematic showing the predicted root-associated gene network based on transcriptome data from the wheat experiment. The network was generated by leveraging the wheat-rice orthologous relationship. Wheat genes differentially expressed between Pavon 76 (P76) and Pavon 1-96-1 translocation line (TL) were identified, their orthologs used to seed the network using RiceNet network tool. The displayed network is populated by genes known to be involved in root trait regulation in model species such as *Arabidopsis*. New genes connected to the input gene set were identified based on RiceNet analysis. The network includes cellulose synthase (CESA3), Chitinase-like 1 (CTL1), Cobra1 (COB 1), Receptor-like Kinase902 (RLK902), Glycosyl Hydrolase 9B7 (GH9B7), Brassinosteroid Insensitivel (BRIt), Protein Phosphatase 2C (PP2C), Erecta-like1 (ERL1), Somatic Embryogenesis Receptor Kinase I (SERKI), F-Box21 (FBL21), and Leucine-Rich Repeat 1 (LRR1).

We found a network populated by genes that are either induced by brassinosteroids (BR) or are directly involved in the BR signaling, indicating a possible role of BR in regulating root system architecture (FIG. 6). This network consists of six genes identified during microarray analysis and five predicted genes. The network includes a component of the BR receptor complex BRI1. Although BRI1 was not identified from our microarray analysis, similarly to SERKI, its expression was also up-regulated in TL compared to P76 under water limited conditions in our real-time PCR assays (FIG. 6 and Table 6). This is consistent with the role of BR in promoting cell wall loosening, root elongation and lateral root development (Mussig et al., 2003, Plant Physiol., 133: 1261-71; Bao et al., 2004, Plant Physiol., 134:1624-31; Wolf et al., 2012, Sci. Signal., 4:ra29). During the early seedling stage, expression of network members, CESA3 and SERKI was higher in TL at 4 and 6 days compared to P76 and NC. Differences in the lateral root production were also observed at these time points in TL relative to the other two genotypes. The BR gene regulatory network identified from our analysis yielded other members that are listed in Table 6. Several of these genes have been previously reported to have root specific phenotypes in when their expression is altered in mutants and/or transgenic plants in model species.

Example 18—In Silico Mapping of Root Related Genes to 7DL of Wheat

Figure 7:
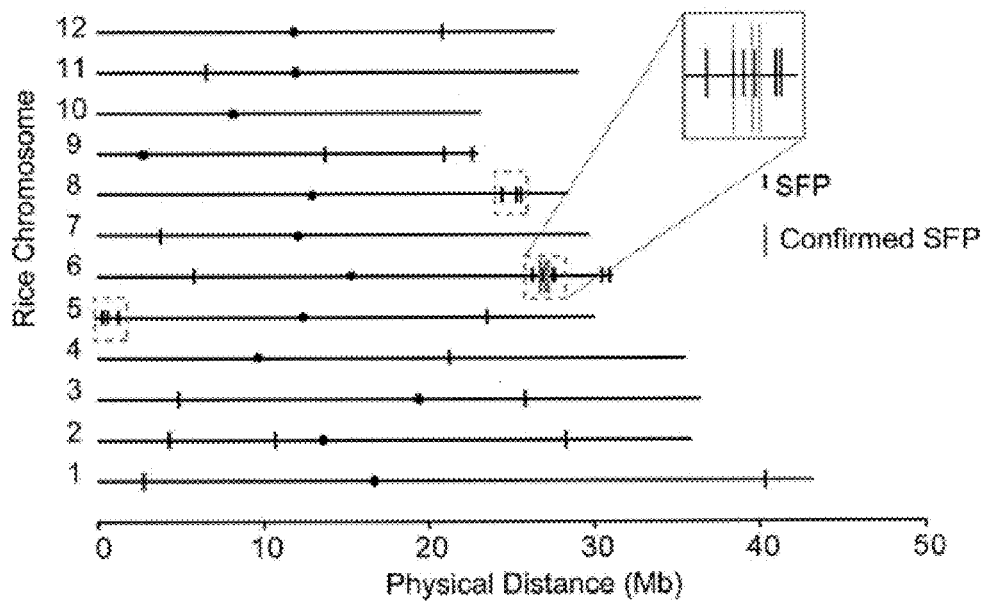
FIG. 7 is a schematic showing in silico mapping of wheat genes on the rice genome using single feature polymorphism analysis (SFP). An SFP analysis was performed by comparing the TL line with P76 and NC to obtain microarray probes that exhibited significant hybridization difference among the genotypes, putatively due to underlying sequence polymorphism. Rice orthologs (vertical bars) of the wheat SFP probe sets were mapped to the rice genome (horizontal bars representing the 10 chromosomes). Based on this analysis, a major rice gene cluster (boxed) on chromosome 6 was identified that has a syntenic relationship with the wheat long arm of chromosome 7D. Rice orthologs in grey represent wheat genes that were differentially expressed between the TL and control genotypes (P76 and NC) under limiting water conditions.

We next explored if the root related differentially expressed genes identified from the microarray analysis between TL and P76 and NC map to the 7DL translocation. We used the wheat array transcriptome dataset to mine for polymorphisms between TL and P76 and the NC using the single feature polymorphism analysis (SFP) (Cui et al., 2005, Bioinformatics, 21:3852-8; Walia et al., 2007, BMC Genomics, 8:87; Kim et al., 2009, BMC Plant Biol., 9:65). Distribution of the SFP probe sets between TL and P76 on the rice genome based on sequence alignment is shown in FIG. 7. The syntenic regions of wheat 7DL region correspond to the rice chromosomes 6 and 8 (Sorrells et al., 2003, Genome Res., 13:1818-27). Six SFP markers clustered to a region on the distal end of chromosome 6 in rice (FIG. 7). Another potential cluster was observed on rice chromosomes 5 and 8, with three SFPs mapped to each cluster. We selected three predicted SFPs from the chromosome 6 cluster, which is syntenic to wheat chromosome 7D for validation by sequencing the PCR amplicons covering the region around the individual SFP probe. We were able to confirm the polymorphic probe sequences for these three probe sets (FIG. 8).

We then tested if rice orthologs of previously identified genes with predicted root related functions map to the chromosome 6 region in the SFP cluster. Both the KNAT3 ortholog and SERKI map to the cluster of SFP markers outlined by the grey box in FIG. 7, while E2F mapped to a region closer to the telomere of chromosome 6. Mapping results suggest that these genes are likely located on the 7DL.7EL translocation. We confirmed the genomic locations of the KNAT3 ortholog and SERKI in wheat using genomic DNA from a subset of ditelosomic and nullisomic-tetrasomic genetic stocks. The set includes six nulli-tetrasomic lines, which lack chromosome 7 for a given genome (A, B or D) and carries four copies of a corresponding homeologous chromosome of another genome, and two ditelosomic lines in which one chromosome pair is composed entirely of either short or long arms. SERKI and the KNAT3 ortholog mapped to 7DL (FIG. 9). Although E2F mapped to the distal segment of rice chromosome 6 in the SFP analysis, we were unable to PCR amplify the transcript in wheat for confirmation.

Part B

Example 19—Identification of Genes Associated with the *Agropyron* Introgression Bread wheat is a hexaploid and has seven homoeologous groups of chromosomes, derived from A, B and D progenitor genomes (Sears, 1969, Ann. Rev. Cytogenet., 3:451-68). Several stress tolerance genes have been introduced into wheat through alien introgressions, which are tolerated due to hexaploid buffering (Gill et al., 2011, PNAS USA, 108:7657-8). One such alien introgression from *Agropyron elongatum* was used to improve leaf rust resistance (Sharma and Knott, 1966, Canadian J. Genet. Cytol., 8:137-43). This *Agropyron* introgression on the wheat chromosome 7D also improved drought tolerance in the translocation line (TL) during vegetative development compared to parental control, Pavon 76 (P76) (FIG. 1a; Placido et al., 2013, Plant Physiol., 161:1806-19). TL apparently exhibits drought tolerance by mitigating the decline in lateral root emergence and lateral root growth experienced by P76 under LW (FIG. 1b, 1c). TL maintained its photosynthetic rate and stomatal conductance in limited water (LW) conditions, while P76 showed a significant drop in these two parameters (FIG. 1d, 1e). No difference was observed between TL and P76 in well-watered (WW) conditions.

To discover the *Agropyron* gene underlying lateral root-associated drought tolerance in TL, we performed root transcriptome assays in well-watered (WW) and limited water (LW) conditions. A gene that we have named Lateral Root Density 7 (LRD7) was identified, which harbors KNOX2 and homeobox domains (FIG. 15). LRD7 was mapped to chromosome 7DL of wheat, corresponding to the *Agropyron* translocation region (Placido et al., 2013, Plant Physiol., 161:1806-19). We sequenced the coding region of LRD7 and identified polymorphisms that confirmed that TL carries the *Agropyron* allele of LRD7 (FIG. 15). To test the allele-specific drought stress regulation of LRD7Ag, we performed qRT-PCR on TL and P76 in WW and LW conditions. In contrast to the wheat allele (LRD7Ta), the LRD7Ag allele is down-regulated in response to water stress in TL (FIG. 1f). These results suggest that drought tolerance in TL is correlated with down-regulation of LRD7Ag during water limitation, likely a consequence of sequence differences associated with the *Agropyron* donor translocation.

(wheat LRD nucleic acid sequence)

SEQ ID NO: 1

ATGACACACTATGTGCTGCTCCTCTGTTCCTTCAAGGAACAGCTCCAGCA
GCATGTGCGCGTCCACGCCATGGAGGCGGTGATGGCCTGCTGGGAGCTCG
AGCAAACTTTGCAGAGTCTTACAGGGGCATCTCCTGGTGAAGGCACCGGG
GCAACTATGTCCGATGACGAAGACAATCCGGTCGACAGTGAGAGCAACAT
GTTTGACGGGAACGATGTGTCAGATGGCATGGGCTTCGGAATGCTAACCG
AGGGTGAGAGATCCTTGGTCGAGCGCGTGAGGCAAGAGCTGAAGCATGAG

-continued
```
CTTAAACAGGGGTATAGAGAAAAGCTTGTGGACATCAGGGAGGAGATACT
GCGGAAGCGAAGAGCCGGAAAGCTCCCAGGGGACACGGCGTCTACCCTGA
AAGCTTGGTGGCAAGCCCACGCCAAATGGCCGTACCCAACTGAGGAGGAC
AAGGCGCGGCTGGTGCAGGAGACGGGGCTGCAGCTGAAGCAGATCAACAA
CTGGTTCATCAACCAGCGCAAGCGGAACTGGCACAGCAACCCTACCTCGT
CCTCGTCAGACAAGAGCAAGAGAAAAAGGAACAATGCAGGTGAAGGCAAC
GCCGAGCAGTCCTGGTAG
```

(wheat LRD amino acid sequence)
SEQ ID NO: 2
```
MTHYVLLLCSFKEQLQQHVRVHAMEAVMACWELEQTLQSLTGASPGEGTG
ATMSDDEDNPVDSESNMFDGNDVSDGMGFGMLTEGERSLVERVRQELKHE
LKQGYREKLVDIREEILRKRRAGKLPGDTASTLKAWWQAHAKWPYPTEED
KARLVQETGLQLKQINNWFINQRKRNWHSNPTSSSSDKSKRKRNNAGEGN
AEQSW
```

Example 20—Transgenic Wheat Having Altered Expression of LRD7

To test this hypothesis, we characterized wheat transgenic events with altered expression of the wheat allele, LRD7Ta. Six-day-old seedlings from wild type CBO37, three RNAi and three overexpression events (OE) from T3 generation were grown in WW and LW conditions. The RNAi plants did not show a significant change in lateral root number and lateral root density in LW (FIG. 11a). In contrast, the lateral root density and lateral root number of CBO37 and the OE plants in LW decreased by nearly 40% of the WW controls. No significant differences were observed in primary and seminal root lengths and shoot length for all three genotypes (FIG. 16). Thus, constitutive suppression of wheat LRD7 mirrors the Agropyron translocation by maintaining lateral root production during drought, thereby supporting our hypothesis.

(RNAi to wheat LRD)
SEQ ID NO: 5
```
GCTGGGAGCTCGAGCAAACTCTGCAGAGTCTTACAGGGGCATCTCCTGGT
GAAGGCACCGGGGCAACTATGTCCGATGACGAAGACAATCCGGTCGACAG
TGAGAGCAACATGTTTGACGGGAACGATGTGTCAGATGGCATGGGCTTCG
GAATGCTAACCGAGGGTGAGAGATCCTTGGTCGAGCGCGTGAGGCAAGAG
CTGAAGCATGAGCTTAAACAGGGGTATAGAGAAAAGCTTGTGGACATCAG
GGAGGAGATACTGCGGAAGCGAAGAGCCGGAAAGCTCCCAGGGGACACGG
CGTCTACCCTGAAAGCTTGGTGGCAAGCCCACGCCAAATGGCCGTACCCA
ACTGAGGAGGACAAGGCGC
```

Morphological and physiological measurements also were recorded for plants exposed to longer (20 d) LW treatment, initiated 7 d post germination (FIG. 11). RNAi plants had longer roots and higher root biomass in LW compared to CBO37 and the OE events (FIG. 11b, 11d). The LRD7 RNAi events at pre-tillering stage had higher shoot biomass relative to CBO37 in both WW and LW conditions (FIG. 17). The 50% decline in stomatal conductance in CBO37 and OE was not observed in the RNAi events in LW (FIG. 11e). Decline in photosynthetic rate (Pn) was greater in CBO37 and the OE events compared to the RNAi events (FIG. 11f). Collectively, these data suggest that wheat LRD7 negatively regulates root biomass, and its suppression during drought is necessary for continued growth in limited water conditions.

Surprisingly, we observed an increase in seed size, 1000-grain weight and number of seeds per plant in LRD7 RNAi events grown to maturity under well-watered greenhouse conditions, while number of tillers was unchanged (FIGS. 12 and 18). In contrast, the LRD7 OE plants had smaller seeds and reduced seed number relative to CBO37. These results suggest that in optimal water conditions, LRD7 negatively regulates reproductive sink capacity and yield components. In this context, it is noteworthy that LRD7Ta is expressed during early seed development and its transcript abundance peaks at 48 h after pollination ("hap"), which corresponds to the developmental window when wheat seeds exhibit rapid increase in size (FIG. 19). To further test the impact of LRD7 suppression on grain yield, we planted the RNAi and OE events and CBO37 in field conditions and observed a 14.0% increase in the 1000-grain weight for the RNAi events relative to CBO37 (FIG. 20).

Example 21—Gibberellic Acid and LRD7

Transcriptomic comparison of the TL line and P76 indicated the differential regulation of several gibberellic acid associated genes (GSE42214; Table 8). Therefore, we tested the role of GA in lateral root regulation by treating TL and P76 seedlings with 104 GA3 in WW and LW conditions. GA treatment in LW restored lateral root number and density to WW levels in P76 (Table 1). Notably, GA treatment increased the TL lateral root number and density under LW to above the untreated values for both LW and WW conditions, suggesting higher GA sensitivity (Table 7). In contrast, GA treatment had no effect on roots of either genotype under WW conditions. Consistent with the lateral root promoting effect of GA in wheat, GA biosynthesis inhibitor specifically suppressed lateral root formation in both P76 and TL (Table 9). Given the positive impact of exogenous GA on lateral roots, we measured the endogenous GA level in 6 d seedling roots. GA1 decreased in P76 in LW compared to WW (FIG. 13a). However, GA1 did not differ significantly in TL in response to LW. This suggests that exogenously applied GA compensates for reduced GA in P76 during water stress, thereby stimulating lateral root formation. Higher GA levels in TL than P76 in LW is likely associated with its ability to maintain lateral root growth in LW. Auxin, which promotes lateral root growth, was not deficient in P76 relative to TL in LW, further supporting a GA-dependent mechanism for maintaining lateral root growth in TL (FIG. 21) (Orman-Ligeza et al., 2013, Trends Plant Sci., 18:459-67; Lavenus et al, 2013, Trends Plant Sci., 18:450-8).

TABLE 7

The Effect of Gibberellin A3 (GA3) on lateral root density

| Treatments | Primary Root Length (cm) | Lateral Root (PR) | Lateral Root Density (cm$^{-1}$) |
|---|---|---|---|
| P76, WW | 25.9 ± 2.6 | 20 ± 5 | 0.86 ± 0.2 |
| P76, WW (+GA$_3$) | 25.5 ± 2.8 | 24 ± 4 | 0.96 ± 0.1 |
| TL, WW | 26.6 ± 2.3 | 23 ± 4 | 0.86 ± 0.1 |
| TL, WW (+GA$_3$) | 27 2 ± 2.2 | 24 ± 5 | 0.89 ± 0.2 |
| P76, LW | 18.8 ± 2.2$^a$ | 10 ± 3$^a$ | 0.53 ± 0.1$^a$ |
| P76, LW (+GA$_3$) | 23.9 ± 2.2$^b$ | 23 ± 3$^b$ | 0.96 ± 0.1$^b$ |
| TL, LW | 27.3 ± 2.7 | 28 ± 4 | 1.01 ± 0.1 |
| TL, LW (+GA$_3$) | 26.4 ± 2.4 | 38 ± 4$^b$ | 1.44 ± 0.1$^b$ |

$^a$represents significant difference between WW and LW treatments for a given genotype at $p < 0.05$ and
$^b$indicates significant difference between untreated control and GA$_3$ at $p < 0.05$ (mean ± s.d., _n = 30).
Number of replicates = 3.

TABLE 8

Gene involved in GA biosynthesis, signaling and response in roots of Agropyron translocation line (TL) in response to limited-water stress

| Wheat Gene ID | Rice Description | Log Fold Change | p-value |
|---|---|---|---|
| Traes_3B_7ABEA6AAD | Gibberellin 2-beta-dioxygenase | −2.40 | 1E−03 |
| Traes_7DL_06A129BOD | Gibberellin 20 oxidase2 | 2.68 | 2E−13 |
| Traes_5DS_BE4C8D436 | GID1L2 | −0.73 | 1E−03 |
| Traes_3B_6D7154F9 | DELLA | −0.71 | 3E−03 |

TABLE 9

Effect of GA biosynthesis inhibitor Paclobutrazol (PAC) on lateral root density

| Genotypes, Treatments | Primary Root Length (cm) | Number of Lateral Roots | Lateral Root Density (cm−1) |
|---|---|---|---|
| P76, WW | 25.2 ± 2.4 | 24 ± 3 | 0.93 ± 0.1 |
| P76, WW (+PAC) | 25.3 ± 3.0 | 11 ± 2$^b$ | 0.45 ± 0.1$^b$ |
| P76, LW | 20.3 ± 1.3$^a$ | 13 ± 3 | 0.55 ± 0.1$^a$ |
| P76, LW (+PAC) | 24.2 ± 2.9 | 5 ± 2$^b$ | 0.22 ± 0.1$^b$ |
| TL, WW | 26.9 ± 3.1 | 25 ± 5 | 0.91 ± 0.2 |
| TL, WW (+PAC) | 22.7 ± 2.4 | 11 ± 2$^b$ | 0.49 ± 0.1$^b$ |
| TL, LW | 26.0 ± 6.0 | 24 ± 7 | 0.87 ± 0.2 |
| TL, LW (+PAC) | 23.9 ± 2.6 | 10 ± 1$^b$ | 0.41 ± 0.1$^b$ |

Root measurements were done on 6 d old seedlings,
$^a$indicates a significant difference between WW and LW treatment for P76 at p < 0.05;
$^b$indicates a significant difference between non-PAC and PAC-treated roots of each genotype at p < 0.05.

Since lower LRD7 expression and higher GA levels correlated with maintaining lateral roots in LW, we tested for a mechanistic link between GA and LRD7. The root transcript abundance of LRD7Ag in GA pretreated TL seedlings in LW was repressed 5-fold relative to untreated WW control (FIG. 13b). GA pretreatment also decreased LRD7Ta expression in P76 roots compared to LW (no GA) roots, but its expression was similar to WW controls, in contrast to LRD7Ag (FIG. 13c). These data suggest that the LRD7Ag is more sensitive to GA inhibition than LRD7Ta. Further, root GA1 levels decreased in CBO37 and OE plants in LW but did not change in the LRD7 RNAi events, suggesting LRD7 may regulate GA homeostasis (FIG. 22).

To explore the underlying basis of GA level differences, we measured the transcript abundance of GA biosynthesis, catabolic and signaling genes (GA20ox, GA2ox, GID1, and SLR1) (FIGS. 13d, 13e, and 23). Notably, the expression of a GA catabolic gene, GA2ox, is strongly up-regulated in response to LW in P76, CBO37 and the OE, whereas it did not change in TL and RNAi roots (FIGS. 13d, 13e). This suggests that in water-stressed P76, CBO37 and OE plants, a GA catabolic gene is strongly induced and lowers GA levels. However, relatively stable GA1 levels in the TL and RNAi roots are associated with continued lateral root growth in LW. Knotted1, a KNOX gene in maize also positively regulates GA2ox1 and consequently lowers GA levels (Bolduc et al., 2008, Sci. Signal, 1:pe28). Transgenically suppressing LRD7 expression in wheat prevents increased GA2ox expression in LW, presumably contributing to maintenance of GA levels.

Example 22—The Effects of LRD in Rice

We next determined if LRD7 could influence grain yield in rice, the most important crop for food security. By repressing the rice homolog of LRD7, OsLRD7 (Os06g43860) via RNAi, we observed an increase in seed size, number of tillers and 1,000-grain weight compared to the wild type Kitaake in field conditions (FIG. 14). Rice LRD RNAi plants also have higher root biomass relative to wild type plants when grown to maturity in well-watered controlled conditions. These data suggest that rice OsLRD7 regulates grain yield in rice under well-watered paddy conditions via increased grain size and more grains per plant compared to the wild type control.

(rice LRD nucleic acid sequence)

SEQ ID NO: 3

ATGGCGTTCCACTACCAGGACCACGCGCTGGCGATGGACGCCGCGGCTGC
GGCGGCGGAGACGGGCGGCCACCACCACCCTGGGTTCGTCGGGGCGGGAG
GAGTTGTGGGGGGAGGAGGAGGAGGAGGGTGGGAGCGGGAGAAGGCCGCC
ATCGCGGCGCACCCGCTGTACGAGCGGCTGCTGGAGGCGCACGTCGCGTG
CCTCCGCGTCGCCACCCCCGTCGACCAGCTGCCCCGCATCGACGCGCAGA
TTGCGGCGCGCCCCCCGCCGCTGGCCGCCGCCACGGCCGCAGCGGCGGCC
GCGGCGGCCGGAGGGGCGCCGTCCGGCGGCGAGGAGCTCGACCTCTTCAT
GACCCATTATGTATTGCTCCTTTGTTCGTTCAAGGAACAACTACAGCAAC
ATGTGCGTGTTCATGCAATGGAAGCAGTAATGGCTTGCTGGGAACTTGAA
CAAACTTTACAGAGCCTTACAGGGGCATCTCCTCGTGAAGGTTCTGGAGC
AACTATGTCTGATGACGAAGACAATCAGGTTGATAGTGAGAGCAACATGT
TTGATGGAAATGATGGATCAGATGGTATGGGCTTTGGCCCCTTAATGCTG
ACGGAGGGCGAGAGATCATTAGTTGAGCGTGTACGGCAAGAGCTGAAACA
TGAGCTTAAACAGGGGTACAGAGAAAAGCTTGTGGACATTAGGGAAGAGA
TACTCCGAAAGCGAAGAGCTGGAAAACTCCCAGGAGATACAGCGTCTACT
TTGAAAGCATGGTGGCAGGCTCACTCTAAATGGCCATACCCAACTGAGGA
GGACAAGGCTCGCTTGGTGCAGGAAACAGGGTTGCAACTAAAACAGATCA
ATAATTGGTTTATCAACCAACGTAAACGGAACTGGCACAGCAATCCTGCT
TCATCCTCATCAGACAAAAGCAAGAGAAAAAGAAGCAATGCAGGTGATGG
CAAGGCCGAGCAATCTTGGTAG (rice LRD amino acid sequence)

SEQ ID NO: 4

MAFHYQDHALAMDAAAAAAETGGHHHPGFVGAGGVVGGGGGGWEREKAA
IAAHPLYERLLEAHVACLRVATPVDQLPRIDAQIAARPPPLAAATAAAAA
AAAGGAPSGGEELDLFMTHYVLLLCSFKEQLQQHVRVHAMEAVMACWELE
QTLQSLTGASPREGSGATMSDDEDNQVDSESNMFDGNDGSDGMGFGPLML
TEGERSLVERVRQELKHELKQGYREKLVDIREEILRKRRAGKLPGDTAST
LKAWWQAHSKWPYPTEEDKARLVQETGLQLKQINNWFINQRKRNWHSNPA
SSSSDKSKRKRSNAGDGKAEQSW (RNAi to rice LRD)

SEQ ID NO: 6

ATGGAAGCAGTAATGGCTTGCTGGGAACTTGAACAAACTTTACAGAGCCT
TACAGGGGCATCTCCTCGTGAAGGTTCTGGAGCAACTATGTCTGATGACG
AAGACAATCAGGTTGATAGTGAGAGCAACATGTTTGATGGAAATGATGGA
TCAGATGGTATGGGCTTTGGCCCCTTAATGCTGACGGAGGGCGAGAGATC
ATTAGTTGAGCGTGTACGGCAAGAGCTGAAACATGAGCTTAAACAGGGGT
ACAGAGAAAAGCTTGTGGACATTAGGGAAGAGATACTCCGAAAGCGAAGA
GCTGGAAAACTCCCAGGAGATACAGCGTCTACTTTGAAAGCATGGTGGCA
GGCTCACTCTAAATGGCCATACCCAACTGAGGAGGACAAGGCTCGCTTGG
TGCAGGAAACAGGGTTGCAACTAAAACAGATCAATAATTGGTTTATCAAC
CAACGTAAACGGAACTGGCAC

TABLE 10

Primer sequences used for qRT-PCR

| Wheat Gene ID | Gene Annotation | Left Primer (5' to 3') | Right Primer (5' to 3') | SEQ ID NOs | Product size (bp) |
|---|---|---|---|---|---|
| LRD7 | LRD7Ta | CCTTCAAGGAACAGCTCCAG | CTCTCACTGTCGACCGGATT | 54, 55 | 166 |
| LRD7 | LRD7 | GTTTGACGGGAACGATGT | ATACCCCTGTTTAAGCTC | 56, 57 | 114 |
| LRD7 | LRD7Ag | GTTCGATGGAAATGATGT | GTACCCCTGTTTAAGCTC | 58, 59 | 151 |
| Traes_3B_7ABEA6AAD | GA20x | GTTCAAGAGCGTGAAGCACA | GTACTCGCCCCATGTGAAGT | 60, 61 | 163 |
| Traes_7DL_06A129B0D | GA20ox | ACATCGACGACACCTTCTCC | ATCCAGGGTCCTCCAGTCAG | 62, 63 | 251 |
| Traes_5DS_BE4C8D436 | GID1 | CGGTGATCAAAGGAAGATGG | ATATTTCTCGGCGTCTCCAA | 64, 65 | 252 |
| Traes_3B_6D71543F9 | DELLA | GGTGAAGCAGATACCCTTGC | GGGCAGGACTCGTAGAAGTG | 66, 67 | 177 |
| | Internal Control | TGAGGTTGTCAAGCAACAGG | CATAAGACCAGCCCAAGCAT | 68, 69 | 152 |

TABLE 11

Primer pairs used for the construction of the LRD7 RNAi-89, RNAi-91, RNAi-92 lines in CB037 background

| Primer Name | Primer Sequence | Lower case bases | SEQ ID NO |
|---|---|---|---|
| PUbi-Int-F | 5' TTTTaagcttGGTGCAGCGTG 3' | HindIII site | 70 |
| Pubi-Sma-R | 5' TTTTcccgggTTCTCGAGCGACCTGCAGAAG 3' | SmaI site | 71 |
| T35S-SmaI-F | 5' TTTTcccgggTAGAGTCCGCAAAAATCACC 3' | SmaI site | 72 |
| T35S-EcoRI-R | 5' TTTTgaattcGCAGGTCACTGGATTTTGGTT 3' | EcoRI site | 73 |
| K369-BH1-F | 5' TTTTggatccGCTGGGAGCTCGAGCAAA 3' | BamHI site | 74 |
| K369-Xb1-R | 5' TTTTtctagaGCGCCTTGTCCTCCTCAGT 3' | XbaI site | 75 |
| K369-SmaI-R | 5' TTTTtctagacccgggGCGCCTTGTCCTCCTCAGT 3' | XbaI and SmaI sites | 76 |

Part C

Example 23—Rice Homolog of the E2F-Related Gene

We characterized the rice homolog (LOC_Os06g50310) of the wheat E2F-related gene. Over-expression of OsbZIP53 in rice driven by a maize ubiquitin promoter induces developmental defects. For example, seed size is dramatically increased by the over-expression of OsbZIP53 (FIGS. 26A and 26B). That is, the length, width and thickness of seeds were approximately 26%, 16%, and 16% higher, respectively, in the over-expression plants than those in wild type plants (FIG. 26C-26E). In contrast, the knock-down, RNAi lines of OsbZIP53 have reduced seed size. The seed width and thickness were 4% to 6% and 9% to 12% smaller, respectively, than those from wild type plants (FIGS. 26D and 26E). The decrease in seed size was consistent with the suppression of OsbZIP53.

(rice E2F-related nucleic acid sequence)
LOC_Os06g50310

SEQ ID NO: 9
ATGGATGACGGGGACCTCGATTTCTCCAACCCGGACACATTCCTCTGCCC
GGCCGTCGGTGGTGCTGACCCCGACGGCAGCTGCTCCATGGACAGCTATT
TCGACGACATCCTCAAGGATACGGAGCACCATGCATGCACCCACACCCAC
ACCTGCAACCCGCCTGTGCATGACCTCTCACACACCCACACCTGCGTCCA
TGTCCACACCAAGATCGTCTCCGCCCCATCCGACACTCCGTCGGATGCTG
CCGAGACCGCCGAGTCCCCGACGGAGAACAATGCCTCCAAGAAGCGGCCG
TCGGGTAACCGTGCCGCTGTGAGGAAGTACAGGGAGAAGAAGAAAGCTCA
CACTGCCTCGCTGGAGGAGGAGGTTGTTCATTTGAGGGCTCTAAACCAGC
AGCTCATGAAGAAGCTCCAGAACCATGCCACGCTCGAGGCAGAGGTATCC
AGGCTGCGGTGCCTGCTCGTTGATATTAGAGGAAGGATTGAAGGGGAGAT
TGGGGCTTTTCCTTATCAGAGGCCAGTGAAGAACATCGATTTGGTTTCTA
GTGTTGATCAGGGAAGTTATCTTGGTGGTGCCCAGGTTATGAACTCCTGT
GACTTTCGATGTGCCGACCAGATGTATTGCAGTCCAGGGATGCAGGTGAG
AACAATGGGCGAGGATGGCGCTGTGAGTGGTCAGGTGTTGGGGCAAGGTG
CCTGTGATATTGCCAGTATCCAATGCCAAGGTGCAAAATCTGGATCTGCA
AAGCTCCCAGTCTGTGGGGCTATGGGTACGATGCCTGTCGGCTGTATGCC
AAATTCTGAAAAGAAATGA (rice E2F-related amino acid sequence)
LOC_Os06g50310

SEQ ID NO: 10
MDDGDLDFSNPDTFLCPAVGGADPDGSCSMDSYFDDILKDTEHHACTHTH
TCNPPVHDLSHTHTCVHVHTKIVSAPSDTPSDAAETAESPTENNASKKRP
SGNRAAVRKYREKKKAHTASLEEEVVHLRALNQQLMKKLQNHATLEAEVS
RLRCLLVDIRGRIEGEIGAFPYQRPVKNIDLVSSVDQGSYLGGAQVMNSC
DFRCADQMYCSPGMQVRTMGEDGAVSGQVLGQGACDIASIQCQGAKSGSA
KLPVCGAMGTMPVGCMPNSEKK

-continued (wheat E2F-related nucleic acid sequence)
SEQ ID NO: 11
TCATTTTCACAAAATTACTTTAAATAGCACGATAATCCTACACACACACG
GACCCTTTACGAGCTTTTACGTGATTTTCTTCTAACTAATCTCTCTCCCG
CTGAAATTCAGCGGGGGTGGACCCCATCCTCCCCTCTTGTCCAATCCCAA
TCGCCCACGTCTGTTAGTCCGTGAACCCCGTAATCAATCCCTCCCTGAGT
CTAGCATTACTCTAAATAACAATTAGTACGATATTTTTGGTCCCAATTGA
CTTTTCTTTCCCGAGTTAGCATCCAATGTAACTATGCTTGAACGGAAATA
AAGCTAGCCAAGAAGGCTTTTCATACAAAAAAAGACGATAATGGCATAAA
ATTTATCTCAGAAGGCAACGTATCCAAAGTAAAATTCTGATGCTACTCTT
TTCTTTTACTAATGATGAAAACAAACAGGAGGCTGTTCACAGGTTCGTAC
GAAGCCACATGAGCTCATCATGACCGGGCCAGCAGAGCCCGGGCCGTCGC
CCTTGGCCGGTCGGCGCTGGTAAGGGAAGGCGCCGATCTCCCCTTCGATC
CTGCCCCTGACGTCGACGAGCAGGCAGCGCAGCCTGGCCGCCTCGGCCTC
GAGCGCGGCGTGGTCCTGGACCTTCTTGGTGAGCTGCTCGTTCATAGCCC
TGAGACGGGCCGCCTCCTCCTGCAGCACCGCCGTGTGCTCCTTCTTCTTC
TCGCGGTACTTGCGCACGGCCGCCCGGTTGCCTGACGGGCGGCGCTTCTT
GCTCCGGGAGGTGGCGTGGGCGTCCTCCGGCTCGGTGGGGGAGTCGGCGG
CGGCGGCGTCGGAGGAGGCGGAGGCGGCGAGCTTGGAGTGGACGTGGTGG
CAGGTGTGGCTGTGGGGGAGGTCGTGGGCGGGCGGGTTGCACGTGTGGGT
GTGGGTGCAGCACGCGAGGTGCTCCGCCGCGCCCCCGAGCACGTCGTCGA
AGTAGCTGCCCATGGACATGGAGGAGAAGTCCAGGTCCCCGTCGTCCATG
GCCGCGATCGATTTGCAGCGACCAGGAGACGCTTAATTAGCCTGTGCTCA
CGTGACGCTTGCATTTGTTTCTTA It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A plant variety, line, or cultivar comprising plants having a mutation in one or more endogenous nucleic acids having a sequence selected from the group consisting of SEQ ID NOs: 1 and 3, wherein the mutation results in reduced expression of the endogenous nucleic acid relative to corresponding plants lacking the mutation, wherein the plants exhibit an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant lacking the mutation under corresponding conditions.

2. Seed produced by the plant variety, line, or cultivar of claim 1, the seed comprising the mutation in one or more endogenous nucleic acids having a sequence selected from the group consisting of SEQ ID NOs: 1 and 3, wherein the mutation results in reduced expression of the endogenous nucleic acid in plants grown from the seed, relative to corresponding plants lacking the mutation, wherein plants grown from the seed exhibit an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a plant grown from corresponding seed lacking the mutation grown under corresponding conditions.

3. A method of making a plant, comprising the steps of:
inducing mutagenesis in plant cells to produce mutagenized cells;
obtaining one or more plants from the mutagenized cells;
identifying plants that comprises a mutation in one or more endogenous nucleic acids having a sequence selected from the group consisting of SEQ ID NOs: 1 and 3 and exhibit reduced expression of the endogenous nucleic acid relative to plants lacking the mutation; and
identifying plants that exhibits an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant lacking the mutation under corresponding conditions.

4. The method of claim 3, wherein mutagenesis is induced using a chemical mutagen or ionizing radiation.

5. The method of claim 4, wherein the chemical mutagen is selected from the group consisting of nitrous acid, sodium azide, acridine orange, ethidium bromide, and ethyl methane sulfonate (EMS).

6. The method of claim 4, wherein the ionizing radiation is selected from the group consisting of x-rays, gamma rays, fast neutron irradiation, and UV irradiation.

7. The method of claim 3, wherein mutagenesis is induced using TALEN technology, zinc-finger technology, or CRISPR technology.

8. A method for producing a plant, said method comprising the steps of:
crossing at least one plant of a first line with at least one plant of a second line, the plant of the first line having a mutation in one or more endogenous nucleic acids having a sequence selected from the group consisting of SEQ ID NOs: 1 and 3, wherein the mutation results in reduced expression of the endogenous nucleic acid relative to a corresponding plant lacking the mutation; and selecting for progeny plants that have the mutation and exhibit reduced expression of the endogenous nucleic acid relative to a corresponding plant lacking the mutation; and selecting for progeny plants exhibiting an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant lacking the mutation under corresponding conditions.

9. A food or feed product comprising plant material from the plant of claim 1.

10. The food or feed product of claim 9, wherein the food product is for human consumption.

11. The food or feed product of claim 9, wherein the feed product is for animal consumption.

12. A method of producing a food or feed product, the method comprising:
providing plant material from a plant having a mutation in one or more endogenous nucleic acids having a sequence selected from the group consisting of SEQ ID NOs: 1 and 3, wherein the mutation results in reduced expression of the endogenous nucleic acid relative to a plant lacking the mutation, wherein the plants exhibit an increase in the length of the primary root under limiting water conditions, an increase in the length of the seminal root under limiting water conditions, an increase in lateral root density under limiting water conditions, an increase in root biomass under limiting water conditions, an increase in the number of seeds per plant under water conditions that are not limiting, an increase in the average size of the seed under water conditions that are not limiting, and/or an increase in the average weight of the seed under water conditions that are not limiting relative to a corresponding plant lacking the mutation under corresponding conditions; and manufacturing a food or feed product using the plant material.

13. The method of claim 12, wherein the mutation is selected from the group consisting of a point mutation, an insertion, a deletion, and a substitution.

* * * * *

UNITED STATES PATENT AND TRADEMARK OFFICE
CERTIFICATE OF CORRECTION

PATENT NO. : 10,036,034 B2
APPLICATION NO. : 14/562182
DATED : July 31, 2018
INVENTOR(S) : Harkamal Walia, Dante Placido and Thomas E. Clemente Page 1 of 1

It is certified that error appears in the above-identified patent and that said Letters Patent is hereby corrected as shown below:

On the Title Page

In Column 2 (other publications), Line 7, please delete "KNOTTED1" and insert --KNOTTED 1--, therefor.

In Column 2 (other publications), Line 52, please delete "2013;" and insert --2003;--, therefor.

Signed and Sealed this
Ninth Day of October, 2018

Andrei Iancu
*Director of the United States Patent and Trademark Office*

SEQUENCE LISTING

<160> NUMBER OF SEQ ID NOS: 76

<210> SEQ ID NO 1
<211> LENGTH: 618
<212> TYPE: DNA
<213> ORGANISM: Triticum aestivum

<400> SEQUENCE: 1

| | | | | | |
|---|---|---|---|---|---|
| atgacacact | atgtgctgct | cctctgttcc | ttcaaggaac | agctccagca | gcatgtgcgc | 60 |
| gtccacgcca | tggaggcggt | gatggcctgc | tgggagctcg | agcaaacttt | gcagagtctt | 120 |
| acagggcat | ctcctggtga | aggcaccggg | gcaactatgt | ccgatgacga | agacaatccg | 180 |
| gtcgacagtg | agagcaacat | gtttgacggg | aacgatgtgt | cagatggcat | gggcttcgga | 240 |
| atgctaaccg | agggtgagag | atccttggtc | gagcgcgtga | ggcaagagct | gaagcatgag | 300 |
| cttaaacagg | ggtatagaga | aaagcttgtg | gacatcaggg | aggagatact | gcggaagcga | 360 |
| agagccggaa | agctcccagg | ggacacggcg | tctaccctga | aagcttggtg | gcaagcccac | 420 |
| gccaaatggc | cgtacccaac | tgaggaggac | aaggcgcggc | tggtgcagga | gacggggctg | 480 |
| cagctgaagc | agatcaacaa | ctggttcatc | aaccagcgca | agcggaactg | gcacagcaac | 540 |
| cctacctcgt | cctcgtcaga | caagagcaag | agaaaaagga | acaatgcagg | tgaaggcaac | 600 |
| gccgagcagt | cctggtag | | | | | 618 |

<210> SEQ ID NO 2
<211> LENGTH: 205
<212> TYPE: PRT
<213> ORGANISM: Triticum aestivum

<400> SEQUENCE: 2

Met Thr His Tyr Val Leu Leu Leu Cys Ser Phe Lys Glu Gln Leu Gln
1               5                   10                  15

Gln His Val Arg Val His Ala Met Glu Ala Val Met Ala Cys Trp Glu
            20                  25                  30

Leu Glu Gln Thr Leu Gln Ser Leu Thr Gly Ala Ser Pro Gly Glu Gly
        35                  40                  45

Thr Gly Ala Thr Met Ser Asp Asp Glu Asp Asn Pro Val Asp Ser Glu
    50                  55                  60

Ser Asn Met Phe Asp Gly Asn Asp Val Ser Asp Gly Met Gly Phe Gly
 65                  70                  75                  80

Met Leu Thr Glu Gly Glu Arg Ser Leu Val Glu Arg Val Arg Gln Glu
                 85                  90                  95

Leu Lys His Glu Leu Lys Gln Gly Tyr Arg Glu Lys Leu Val Asp Ile
             100                 105                 110

Arg Glu Glu Ile Leu Arg Lys Arg Ala Gly Lys Leu Pro Gly Asp
             115                 120                 125

Thr Ala Ser Thr Leu Lys Ala Trp Trp Gln Ala His Ala Lys Trp Pro
        130                 135                 140

Tyr Pro Thr Glu Glu Asp Lys Ala Arg Leu Val Gln Glu Thr Gly Leu
145                 150                 155                 160

Gln Leu Lys Gln Ile Asn Asn Trp Phe Ile Asn Gln Arg Lys Arg Asn
                165                 170                 175

Trp His Ser Asn Pro Thr Ser Ser Ser Asp Lys Ser Lys Arg Lys
            180                 185                 190

Arg Asn Asn Ala Gly Glu Gly Asn Ala Glu Gln Ser Trp
        195                 200                 205

<210> SEQ ID NO 3
<211> LENGTH: 972
<212> TYPE: DNA
<213> ORGANISM: Oryza sativa

<400> SEQUENCE: 3
atggcgttcc actaccagga ccacgcgctg gcgatggacg ccgcggctgc ggcggcggag     60
acgggcggcc accaccaccc tgggttcgtc ggggcgggag gagttgtggg gggaggagga    120
ggaggagggt gggagcggga gaaggccgcc atcgcggcgc acccgctgta cgagcggctg    180
ctggaggcgc acgtcgcgtg cctccgcgtc gccaccccg tcgaccagct gccccgcatc    240
gacgcgcaga ttgcggcgcg cccccccgcc ctggccgccg ccacggccgc agcggcggcc    300
gcggcggccg gaggggcgcc gtccggcggc gaggagctcg acctcttcat gacccattat    360
gtattgctcc tttgttcgtt caaggaacaa ctacagcaac atgtgcgtgt tcatgcaatg    420
gaagcagtaa tggcttgctg ggaacttgaa caaactttac agagccttac aggggcatct    480
cctcgtgaag ttctggagc aactatgtct gatgacgaag acaatcaggt tgatagtgag    540
agcaacatgt ttgatggaaa tgatggatca gatggtatgg gctttggccc cttaatgctg    600
acggagggcg agagatcatt agttgagcgt gtacggcaag agctgaaaca tgagcttaaa    660 cagggggtaca gagaaaagct tgtggacatt agggaagaga tactccgaaa gcgaagagct    720
ggaaaactcc caggagatac agcgtctact ttgaaagcat ggtggcaggc tcactctaaa    780
tggccatacc caactgagga ggacaaggct cgcttggtgc aggaaacagg ttgcaactaa   840
aaacagatca ataattggtt tatcaaccaa cgtaaacgga actggcacag caatcctgct   900
tcatcctcat cagacaaaag caagagaaaa agaagcaatg caggtgatgg caaggccgag   960
caatcttggt ag                                                       972

<210> SEQ ID NO 4
<211> LENGTH: 323
<212> TYPE: PRT
<213> ORGANISM: Oryza sativa

<400> SEQUENCE: 4

Met Ala Phe His Tyr Gln Asp His Ala Leu Ala Met Asp Ala Ala Ala
1               5                   10                  15

Ala Ala Ala Glu Thr Gly Gly His His Pro Gly Phe Val Gly Ala
            20                  25                  30

Gly Gly Val Val Gly Gly Gly Gly Gly Trp Glu Arg Glu Lys
        35                  40                  45

Ala Ala Ile Ala Ala His Pro Leu Tyr Glu Arg Leu Leu Glu Ala His
50                      55                  60

Val Ala Cys Leu Arg Val Ala Thr Pro Val Asp Gln Leu Pro Arg Ile
65                  70                  75                  80

Asp Ala Gln Ile Ala Ala Arg Pro Pro Leu Ala Ala Thr Ala
                85                  90                  95

Ala Ala Ala Ala Ala Ala Gly Gly Ala Pro Ser Gly Gly Glu Glu
            100                 105                 110

Leu Asp Leu Phe Met Thr His Tyr Val Leu Leu Cys Ser Phe Lys
            115                 120                 125

Glu Gln Leu Gln Gln His Val Arg Val His Ala Met Glu Ala Val Met
130                 135                 140

Ala Cys Trp Glu Leu Glu Gln Thr Leu Gln Ser Leu Thr Gly Ala Ser
145                 150                 155                 160

Pro Arg Glu Gly Ser Gly Ala Thr Met Ser Asp Asp Glu Asp Asn Gln
                165                 170                 175

Val Asp Ser Glu Ser Asn Met Phe Asp Gly Asn Asp Gly Ser Asp Gly
            180                 185                 190

Met Gly Phe Gly Pro Leu Met Leu Thr Glu Gly Glu Arg Ser Leu Val
        195                 200                 205

Glu Arg Val Arg Gln Glu Leu Lys His Glu Leu Lys Gln Gly Tyr Arg
210                 215                 220

Glu Lys Leu Val Asp Ile Arg Glu Glu Ile Leu Arg Lys Arg Arg Ala
225                 230                 235                 240

Gly Lys Leu Pro Gly Asp Thr Ala Ser Thr Leu Lys Ala Trp Trp Gln
                245                 250                 255

Ala His Ser Lys Trp Pro Tyr Pro Thr Glu Glu Asp Lys Ala Arg Leu
            260                 265                 270

Val Gln Glu Thr Gly Leu Gln Leu Lys Gln Ile Asn Asn Trp Phe Ile
        275                 280                 285

Asn Gln Arg Lys Arg Asn Trp His Ser Asn Pro Ala Ser Ser Ser Ser
290                 295                 300

Asp Lys Ser Lys Arg Lys Arg Ser Asn Ala Gly Asp Gly Lys Ala Glu
305                 310                 315                 320

Gln Ser Trp

<210> SEQ ID NO 5
<211> LENGTH: 369
<212> TYPE: DNA
<213> ORGANISM: Artificial Sequence
<220> FEATURE:
<223> OTHER INFORMATION: synthetic oligonucleotide

<400> SEQUENCE: 5
gctgggagct cgagcaaact ctgcagagtc ttacaggggc atctcctggt gaaggcaccg     60
gggcaactat gtccgatgac gaagacaatc cggtcgacag tgagagcaac atgtttgacg    120
ggaacgatgt gtcagatggc atgggcttcg gaatgctaac cgagggtgag agatccttgg    180

```
tcgagcgcgt gaggcaagag ctgaagcatg agcttaaaca ggggtataga gaaaagcttg      240
tggacatcag ggaggagata ctgcggaagc gaagagccgg aaagctccca ggggacacgg      300
cgtctaccct gaaagcttgg tggcaagccc acgccaaatg gccgtaccca actgaggagg      360
acaaggcgc                                                             369

<210> SEQ ID NO 6
<211> LENGTH: 471
<212> TYPE: DNA
<213> ORGANISM: Artificial Sequence
<220> FEATURE:
<223> OTHER INFORMATION: synthetic oligonucleotide

<400> SEQUENCE: 6
atggaagcag taatggcttg ctgggaactt gaacaaactt tacagagcct tacaggggca       60
tctcctcgtg aaggttctgg agcaactatg tctgatgacg aagacaatca ggttgatagt      120
gagagcaaca tgtttgatgg aaatgatgga tcagatggta tgggctttgg ccccttaatg      180
ctgacggagg gcgagagatc attagttgag cgtgtacggc aagagctgaa acatgagctt      240
aaacaggggt acagagaaaa gcttgtggac attaggaaag atactccg aaagcgaaga       300 gctggaaaac tcccaggaga tacagcgtct actttgaaag catggtggca ggctcactct      360
aaatggccat acccaactga ggaggacaag gctcgcttgg tgcaggaaac agggttgcaa      420
ctaaaacaga tcaataattg gtttatcaac caacgtaaac ggaactggca c              471

<210> SEQ ID NO 7
<211> LENGTH: 1296
<212> TYPE: DNA
<213> ORGANISM: Arabidopsis thaliana

<400> SEQUENCE: 7
atggcgtttc atcacaatca tctctcacaa gacctctcct tcaatcattt caccgaccaa       60
caccaacctc cacctccgca accgcctcct cctcctccgc aacagcaaca acatttccaa      120
gaagcaccgc ctcctaattg gttaaacaca gcgcttcttc gttcctcaga taacaacaat      180
aacttcctca acctccacac agccaccgct aacaccacaa ccgcaagcag ctccgattct      240
ccttcctccg ccgccgccgc cgccgctgct aaccagtggc tatctcgctc ctcctctttc      300
ctccaacgaa acaacaacaa caacgcttcc atagtcggag atgggatcga tgatgtcacc      360
ggaggagcag acactatgat tcagggagag atgaaaaccg gcggtggaga aaacaaaaac      420
gacggcggag gagctacggc ggcggatgga gtagtgagct ggcagaatgc gagacacaag      480
gcggagatcc tttcgcatcc tctttacgag cagcttttgt cggcgcacgt tgcttgtttg      540
agaatcgcga ctccggttga tcagcttccg agaatcgatg ctcagcttgc tcagtctcaa      600
cacgtcgtcg ctaaatactc agctttaggc gccgccgctc aaggtctcgt cggcgacgat      660
aaagaacttg accagttcat gacacattat gtgttgctac tgtgttcatt taaagagcaa      720
ttgcaacaac atgtgcgtgt tcatgcaatg gaagctgtga tggcttgttg ggagattgag      780
cagtctcttc aaagcttaac aggagtgtct cctggagaag ggatgggagc aacaatgtct      840
gacgatgaag atgaacaagt agagagtgat gctaatatgt tcgatggggg attagatgtg      900
ttgggttttg gtcctttgat tcctactgag agtgagaggt cgttgatgga aagagttaga      960
caagaactta acatgaact caaacagggt tacaaggaga gatagtaga cataagagag     1020 gagatattaa ggaagagaag agctgggaag ttaccaggag ataccacctc tgttctcaaa     1080
```

```
gcttggtggc aatctcattc caaatggcct taccctactg aggaagataa ggcgaggttg   1140
gtgcaagaga caggtttgca gctaaaacag ataaacaatt ggttcatcaa tcagagaaag   1200
aggaactggc atagcaatcc atcttcttcc actgtattga agaacaaacg caaaagcaat   1260
gcaggtgaca atagcggaag agagcggttc gcgtag                             1296
```

<210> SEQ ID NO 8
<211> LENGTH: 431
<212> TYPE: PRT
<213> ORGANISM: Arabidopsis thaliana

<400> SEQUENCE: 8

```
Met Ala Phe His His Asn His Leu Ser Gln Asp Leu Ser Phe Asn His
1               5                   10                  15

Phe Thr Asp Gln His Gln Pro Pro Pro Gln Pro Pro Pro Pro Pro Pro
            20                  25                  30

Pro Gln Gln Gln Gln His Phe Gln Glu Ala Pro Pro Asn Trp Leu
        35                  40                  45

Asn Thr Ala Leu Leu Arg Ser Ser Asp Asn Asn Asn Phe Leu Asn
    50                  55                  60

Leu His Thr Ala Thr Ala Asn Thr Thr Thr Ala Ser Ser Ser Asp Ser
65                  70                  75                  80

Pro Ser Ser Ala Ala Ala Ala Ala Ala Asn Gln Trp Leu Ser Arg
                85                  90                  95

Ser Ser Ser Phe Leu Gln Arg Asn Asn Asn Asn Asn Ala Ser Ile Val
            100                 105                 110

Gly Asp Gly Ile Asp Asp Val Thr Gly Gly Ala Asp Thr Met Ile Gln
        115                 120                 125

Gly Glu Met Lys Thr Gly Gly Glu Asn Lys Asn Asp Gly Gly Gly
    130                 135                 140

Ala Thr Ala Ala Asp Gly Val Val Ser Trp Gln Asn Ala Arg His Lys
145                 150                 155                 160

Ala Glu Ile Leu Ser His Pro Leu Tyr Glu Gln Leu Leu Ser Ala His
                165                 170                 175

Val Ala Cys Leu Arg Ile Ala Thr Pro Val Asp Gln Leu Pro Arg Ile
            180                 185                 190

Asp Ala Gln Leu Ala Gln Ser Gln His Val Val Ala Lys Tyr Ser Ala
        195                 200                 205

Leu Gly Ala Ala Ala Gln Gly Leu Val Gly Asp Asp Lys Glu Leu Asp
    210                 215                 220

Gln Phe Met Thr His Tyr Val Leu Leu Leu Cys Ser Phe Lys Glu Gln
225                 230                 235                 240

Leu Gln Gln His Val Arg Val His Ala Met Glu Ala Val Met Ala Cys
                245                 250                 255

Trp Glu Ile Glu Gln Ser Leu Gln Ser Leu Thr Gly Val Ser Pro Gly
            260                 265                 270

Glu Gly Met Gly Ala Thr Met Ser Asp Asp Glu Asp Glu Gln Val Glu
        275                 280                 285

Ser Asp Ala Asn Met Phe Asp Gly Gly Leu Asp Val Leu Gly Phe Gly
    290                 295                 300

Pro Leu Ile Pro Thr Glu Ser Glu Arg Ser Leu Met Glu Arg Val Arg
305                 310                 315                 320

Gln Glu Leu Lys His Glu Leu Lys Gln Gly Tyr Lys Glu Lys Ile Val
                325                 330                 335
```

```
Asp Ile Arg Glu Glu Ile Leu Arg Lys Arg Ala Gly Lys Leu Pro
            340                 345                 350

Gly Asp Thr Thr Ser Val Leu Lys Ala Trp Trp Gln Ser His Ser Lys
        355                 360                 365

Trp Pro Tyr Pro Thr Glu Glu Asp Lys Ala Arg Leu Val Gln Glu Thr
    370                 375                 380

Gly Leu Gln Leu Lys Gln Ile Asn Asn Trp Phe Ile Asn Gln Arg Lys
385                 390                 395                 400

Arg Asn Trp His Ser Asn Pro Ser Ser Thr Val Leu Lys Asn Lys
                405                 410                 415

Arg Lys Ser Asn Ala Gly Asp Asn Ser Gly Arg Glu Arg Phe Ala
            420                 425                 430

<210> SEQ ID NO 9
<211> LENGTH: 819
<212> TYPE: DNA
<213> ORGANISM: Oryza sativa

<400> SEQUENCE: 9
atggatgacg gggacctcga tttctccaac ccggacacat tcctctgccc ggccgtcggt      60
ggtgctgacc ccgacggcag ctgctccatg gacagctatt tcgacgacat cctcaaggat    120
acggagcacc atgcatgcac ccacacccac acctgcaacc cgcctgtgca tgacctctca    180
cacacccaca cctgcgtcca tgtccacacc aagatcgtct ccgccccatc cgacactccg    240
tcggatgctg ccgagaccgc cgagtccccg acggagaaca atgcctccaa gaagcggccg    300
tcgggtaacc gtgccgctgt gaggaagtac agggagaaga gaaagctcca cactgcctcg    360
ctggaggagg aggttgttca tttgagggct ctaaaccagc agctcatgaa gaagctccag    420
aaccatgcca cgctcgaggc agaggtatcc aggctgcggt gcctgctcgt tgatattaga    480
ggaaggattg aagggagat tggggctttt ccttatcaga ggccagtgaa gaacatcgat     540
ttggtttcta gtgttgatca gggaagttat cttggtggtg cccaggttat gaactcctgt    600
gactttcgat gtgccgacca gatgtattgc agtccaggga tgcaggtgag aacaatgggc    660
gaggatggcg ctgtgagtgg tcaggtgttg gggcaaggtg cctgtgatat tgccagtatc    720
caatgccaag gtgcaaaatc tggatctgca agctcccag tctgtgggc tatgggtacg     780 atgcctgtcg gctgtatgcc aaattctgaa agaaatga                            819

<210> SEQ ID NO 10
<211> LENGTH: 272
<212> TYPE: PRT
<213> ORGANISM: Oryza sativa

<400> SEQUENCE: 10

Met Asp Asp Gly Asp Leu Asp Phe Ser Asn Pro Asp Thr Phe Leu Cys
1               5                   10                  15

Pro Ala Val Gly Gly Ala Asp Pro Asp Gly Ser Cys Ser Met Asp Ser
            20                  25                  30

Tyr Phe Asp Asp Ile Leu Lys Asp Thr Glu His His Ala Cys Thr His
        35                  40                  45

Thr His Thr Cys Asn Pro Pro Val His Asp Leu Ser Thr His Thr
    50                  55                  60

Cys Val His Val His Thr Lys Ile Val Ser Ala Pro Ser Asp Thr Pro
65                  70                  75                  80

Ser Asp Ala Ala Glu Thr Ala Glu Ser Pro Thr Glu Asn Asn Ala Ser
                85                  90                  95
```

Lys Lys Arg Pro Ser Gly Asn Arg Ala Ala Val Arg Lys Tyr Arg Glu
            100                 105                 110

Lys Lys Lys Ala His Thr Ala Ser Leu Glu Glu Val Val His Leu
            115                 120                 125

Arg Ala Leu Asn Gln Gln Leu Met Lys Lys Leu Gln Asn His Ala Thr
130                 135                 140

Leu Glu Ala Glu Val Ser Arg Leu Arg Cys Leu Leu Val Asp Ile Arg
145                 150                 155                 160

Gly Arg Ile Glu Gly Glu Ile Gly Ala Phe Pro Tyr Gln Arg Pro Val
                165                 170                 175

Lys Asn Ile Asp Leu Val Ser Ser Val Asp Gln Gly Ser Tyr Leu Gly
            180                 185                 190

Gly Ala Gln Val Met Asn Ser Cys Asp Phe Arg Cys Ala Asp Gln Met
            195                 200                 205

Tyr Cys Ser Pro Gly Met Gln Val Arg Thr Met Gly Glu Asp Gly Ala
            210                 215                 220

Val Ser Gly Gln Val Leu Gly Gln Gly Ala Cys Asp Ile Ala Ser Ile
225                 230                 235                 240

Gln Cys Gln Gly Ala Lys Ser Gly Ser Ala Lys Leu Pro Val Cys Gly
                245                 250                 255

Ala Met Gly Thr Met Pro Val Gly Cys Met Pro Asn Ser Glu Lys Lys
            260                 265                 270

<210> SEQ ID NO 11
<211> LENGTH: 1074
<212> TYPE: DNA
<213> ORGANISM: Triticum aestivum

<400> SEQUENCE: 11
tcattttcac aaaattactt taaatagcac gataatccta cacacacacg gacccttta c      60
gagcttttac gtgattttct tctaactaat ctctctcccg ctgaaattca gcggggtgg      120
accccatcct ccctcttgt ccaatcccaa tcgcccacgt ctgttagtcc gtgaaccccg      180
taatcaatcc ctccctgagt ctagcattac tctaaataac aattagtacg atattttgg      240
tcccaattga cttttctttc ccgagttagc atccaatgta actatgcttg aacggaaata      300
aagctagcca agaaggcttt tcatacaaaa aaagacgata atggcataaa atttatctca      360
gaaggcaacg tatccaaagt aaaattctga tgctactctt ttcttttact aatgatgaaa      420
acaaacagga ggctgttcac aggttcgtac gaagccacat gagctcatca tgaccgggcc      480
agcagagccc gggccgtcgc ccttggccgg tcggcgctgg taagggaagg cgccgatctc      540
cccttcgatc ctgcccctga cgtcgacgag caggcagcgc agcctggccg cctcggcctc      600
gagcgcggcg tggtcctgga ccttcttggt gagctgctcg ttcatagccc tgagacgggc      660
cgcctcctcc tgcagcaccg ccgtgtgctc cttcttcttc tcgcggtact gcgcacggc       720
cgcccggttg cctgacgggc ggcgcttctt gctccgggag gtggcgtggg cgtcctccgg      780
ctcggtgggg gagtcggcgg cggcggcgtc ggaggaggcg gaggcggcga gcttggagtg      840
gacgtggtgg caggtgtggc tgtggggag gtcgtgggcg ggcggggttgc acgtgtgggt     900
gtgggtgcag cacgcgaggt gctccgccgc gccccgagc acgtcgtcga agtagctgcc      960
catggacatg gaggagaagt ccaggtcccc gtcgtccatg gccgcgatcg atttgcagcg     1020
accaggagac gcttaattag cctgtgctca cgtgacgctt gcatttgttt ctta           1074

<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 12
cctcctgaga ttggcacatt                                        20

<210> SEQ ID NO 13
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 13
gcattgtgcc actgaacttg                                        20

<210> SEQ ID NO 14
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 14
ccttcaagga acagctccag                                        20

<210> SEQ ID NO 15
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 15
ctctcactgt cgaccggatt                                        20

<210> SEQ ID NO 16
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 16
gtcatgagtg gccaggtttt                                        20

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
gccaatagtc tctcgcaagg                                        20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

```
<400> SEQUENCE: 18
ttgtgctgcg attgattgtt                                              20

<210> SEQ ID NO 19
<211> LENGTH: 20
<212> TYPE: PRT
<213> ORGANISM: Artificial Sequence
<220> FEATURE:
<223> OTHER INFORMATION: synthetic oligonucleotide

<400> SEQUENCE: 19

Thr Ala Ala Gly Thr Cys Thr Cys Cys Cys Gly Gly Thr Thr Gly Ala
1               5                   10                  15

Thr Thr Gly Gly
            20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
tgttcaagcc tcaacagacg                                              20

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
ttgccaacaa gaaacaacca                                              20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
ggtggaattc tctgcagcat                                              20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
agcttcattg ggttgtcacc                                              20

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
gcattcatgg tgtggatcag                                              20
```

```
<210> SEQ ID NO 25
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 25
atggggttcg atcaattcaa                                                 20

<210> SEQ ID NO 26
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 26
accagaccat caccgacttc                                                 20

<210> SEQ ID NO 27
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 27
gccgtatcca catgaggtct                                                 20

<210> SEQ ID NO 28
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 28
caagctctca tgtcgtggaa                                                 20

<210> SEQ ID NO 29
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 29
acacagcttc ctggacgagt                                                 20

<210> SEQ ID NO 30
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 30
tgctagcagg aggttggatt                                                 20

<210> SEQ ID NO 31
<211> LENGTH: 20
<212> TYPE: DNA
<213> ORGANISM: Artificial Sequence
<220> FEATURE:
```

<223> OTHER INFORMATION: synthetic oligonucleotide

<400> SEQUENCE: 31
tccctgtttc ttggtccttg        20

<210> SEQ ID NO 32
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 32
cactgctaat tcgctcacca        20

<210> SEQ ID NO 33
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 33
cagcatggtc tcggaatttt        20

<210> SEQ ID NO 34
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 34
cagaaggccg acgtctacag        20

<210> SEQ ID NO 35
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 35
accatctcct cctccacgtt        20

<210> SEQ ID NO 36
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 36
ccctggtttg agcaagtcat        20

<210> SEQ ID NO 37
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 37
agtcgtgact gaaggggttg        20

```
<210> SEQ ID NO 38
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 38
tgaggttgtc aagcaacagg                                                   20

<210> SEQ ID NO 39
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 39
cataagacca gcccaagcat                                                   20

<210> SEQ ID NO 40
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 40
cgtctaccct gaaagcttgg                                                   20

<210> SEQ ID NO 41
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 41
cctcacctgc attgttcctt                                                   20

<210> SEQ ID NO 42
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 42
gacggcttca ccgtcatatt                                                   20

<210> SEQ ID NO 43
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 43
agcagctacg gcatcagaat                                                   20

<210> SEQ ID NO 44
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 44
aatcgtacaa ccacccaagc                                               20

<210> SEQ ID NO 45
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 45
attgtagcac ttggcgtcag                                               20

<210> SEQ ID NO 46
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 46
gtcaacacaa ggttggctca                                               20

<210> SEQ ID NO 47
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 47
agccttgaga tccttggtga                                               20

<210> SEQ ID NO 48
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 48
agtatctgca tccacctcga c                                             21

<210> SEQ ID NO 49
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 49
ctggcatcca ccttcttctt                                               20

<210> SEQ ID NO 50
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 50
cgttaatgag accgctttcc                                               20

<210> SEQ ID NO 51
<211> LENGTH: 20

```
<212> TYPE: DNA
<213> ORGANISM: Artificial Sequence
<220> FEATURE:
<223> OTHER INFORMATION: synthetic oligonucleotide

<400> SEQUENCE: 51
gatcagcaat ccagcattca                                          20

<210> SEQ ID NO 52
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 52
cagatggttc gttcggtgat                                          20

<210> SEQ ID NO 53
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 53
agcagagagc aacggaaaac                                          20

<210> SEQ ID NO 54
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 54
ccttcaagga acagctccag                                          20

<210> SEQ ID NO 55
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 55
ctctcactgt cgaccggatt                                          20

<210> SEQ ID NO 56
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 56
gtttgacggg aacgatgt                                            18

<210> SEQ ID NO 57
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 57
```

```
ataccoctgt ttaagctc                                                 18

<210> SEQ ID NO 58
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 58
gttcgatgga aatgatgt                                                 18

<210> SEQ ID NO 59
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 59 gtaccoctgt ttaagctc                                                 18

<210> SEQ ID NO 60
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 60
gttcaagagc gtgaagcaca                                               20

<210> SEQ ID NO 61
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 61
gtactcgccc catgtgaagt                                               20

<210> SEQ ID NO 62
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 62
acatcgacga caccttctcc                                               20

<210> SEQ ID NO 63
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 63
atccagggtc ctccagtcag                                               20

<210> SEQ ID NO 64
<211> LENGTH: 20
<212> TYPE: DNA
<213> ORGANISM: Artificial Sequence
```

<220> FEATURE:
<223> OTHER INFORMATION: synthetic oligonucleotide

<400> SEQUENCE: 64
cggtgatcaa aggaagatgg                                              20

<210> SEQ ID NO 65
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 65
atatttctcg gcgtctccaa                                              20

<210> SEQ ID NO 66
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 66
ggtgaagcag ataccctttgc                                             20

<210> SEQ ID NO 67
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 67
gggcaggact cgtagaagtg                                              20

<210> SEQ ID NO 68
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 68
tgaggttgtc aagcaacagg                                              20

<210> SEQ ID NO 69
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 69
cataagacca gcccaagcat                                              20

<210> SEQ ID NO 70
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 70
ttttaagctt ggtgcagcgt g                                            21

```
<210> SEQ ID NO 71
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 71
ttttcccggg ttctcgagcg acctgcagaa g                                          31

<210> SEQ ID NO 72
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 72
ttttcccggg tagagtccgc aaaaatcacc                                            30

<210> SEQ ID NO 73
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 73
ttttgaattc gcaggtcact ggattttggt t                                          31

<210> SEQ ID NO 74
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 74
ttttggatcc gctgggagct cgagcaaa                                              28

<210> SEQ ID NO 75
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 75
ttttctagag cgccttgtcc tcctcagt                                              28

<210> SEQ ID NO 76
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 76
tttttctaga cccggggcgc cttgtcctcc tcagt                                      35
```